(12) United States Patent
Fukui et al.

(10) Patent No.: US 8,076,111 B2
(45) Date of Patent: Dec. 13, 2011

(54) METHOD FOR PRODUCING AN ORGANIC ACID

(75) Inventors: Keita Fukui, Kawasaki (JP); Yoshinori Tajima, Kawasaki (JP); Kazue Kawamura, Kawasaki (JP); Yoshihiro Usuda, Kawasaki (JP); Kazuhiko Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 90 days.

(21) Appl. No.: 12/579,594

(22) Filed: Oct. 15, 2009

(65) Prior Publication Data

US 2010/0081180 A1    Apr. 1, 2010

Related U.S. Application Data

(63) Continuation of application No. PCT/JP2008/057397, filed on Apr. 16, 2008.

(30) Foreign Application Priority Data

Apr. 16, 2007  (JP) .................................. 2007-106909
Sep. 19, 2007  (JP) .................................. 2007-242866

(51) Int. Cl.
| | |
|---|---|
| C12P 7/46 | (2006.01) |
| C12P 1/04 | (2006.01) |
| C12P 21/06 | (2006.01) |
| C12P 19/34 | (2006.01) |
| C12N 1/20 | (2006.01) |
| C12N 9/00 | (2006.01) |
| C07H 21/02 | (2006.01) |
| C07H 21/04 | (2006.01) |
| C07K 1/00 | (2006.01) |

(52) U.S. Cl. ...... 435/145; 435/170; 435/69.1; 435/91.1; 435/252.3; 435/252.8; 435/183; 536/23.1; 536/23.2; 536/23.7; 530/350

(58) Field of Classification Search .................. 435/145, 435/170, 69.1, 91.1, 252.3, 252.8, 183; 536/23.1, 536/23.2, 23.7; 530/350
See application file for complete search history.

(56) References Cited

U.S. PATENT DOCUMENTS

| | | | |
|---|---|---|---|
| 5,142,834 A | 9/1992 | Laclave et al. |
| 5,504,004 A | 4/1996 | Guettler et al. |
| 6,911,332 B2 | 6/2005 | Usuda et al. |
| 7,026,149 B2 | 4/2006 | Usuda et al. |
| 7,029,893 B2 | 4/2006 | Usuda et al. |
| 7,060,475 B2 | 6/2006 | Usuda et al. |
| 7,090,998 B2 | 8/2006 | Ishikawa et al. |
| 7,192,748 B2 | 3/2007 | Usuda et al. |
| 7,220,570 B2 | 5/2007 | Usuda et al. |
| 7,306,933 B2 | 12/2007 | Van Dien et al. |
| 7,468,262 B2 | 12/2008 | Usuda et al. |
| 2002/0115159 A1 | 8/2002 | Farwick et al. |
| 2002/0142404 A1 | 10/2002 | Farwick et al. |
| 2002/0155556 A1 | 10/2002 | Imaizumi et al. |
| 2004/0265956 A1 | 12/2004 | Takikawa et al. |
| 2005/0170482 A1 | 8/2005 | San et al. |
| 2005/0196846 A1 | 9/2005 | Hara et al. |
| 2005/0233308 A1 | 10/2005 | Nishio et al. |
| 2006/0003424 A1 | 1/2006 | Asakura et al. |
| 2006/0234356 A1 | 10/2006 | Usuda et al. |
| 2006/0234357 A1 | 10/2006 | Usuda et al. |
| 2007/0249017 A1 | 10/2007 | Usuda et al. |
| 2007/0254345 A1 | 11/2007 | Fukui et al. |
| 2009/0068712 A1 | 3/2009 | Terashita et al. |
| 2009/0093029 A1 | 4/2009 | Usuda et al. |
| 2009/0104659 A1 | 4/2009 | Smirnov et al. |
| 2009/0148915 A1 | 6/2009 | Van Dien et al. |
| 2009/0203090 A1 | 8/2009 | Ptitsyn et al. |
| 2009/0239269 A1 | 9/2009 | Tajima et al. |
| 2009/0246835 A1 | 10/2009 | Iwatani et al. |

FOREIGN PATENT DOCUMENTS

| | | |
|---|---|---|
| JP | 11-113588 | 4/1999 |
| JP | 11-196887 | 7/1999 |
| JP | 11-196888 | 7/1999 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol.,2001, vol. 183 (8): 2405-2410.*
Wishart et al., A single mutation converts a novel phosphotyrosine binding domain into a dual-specificity phosphatase. J. Biol. Chem., 1995, vol. 270(45): 26782-26785.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Database UnitProt [online] Apr. 13, 2004 UniProtKB Entry: P60872, putative transport protein yidE.
Hayashi, K., et al., "Highly accurate genome sequences of *Escherichia coli* K-12 strains MG1655 and W3110," Mol. Systems Biol. 2006, vol. 2, Article No. 2006.0007, pp. 1-5.
International Search Report for PCT Patent App. No. PCT/JP2008/057397 (Jun. 24, 2008).
Guettler, M. V., et al., "*Actinobacillus succinogenes* sp. nov., a novel succinic-acid-producing strain from the bovine rumen," Int. J. Systemic Bacteriol. 1999;49:207-216.

(Continued)

*Primary Examiner* — Ganapathirama Raghu
(74) *Attorney, Agent, or Firm* — Shelly Guest Cermak; Cermak Nakajima LLP

(57) ABSTRACT

An organic acid is produced by allowing a bacterium which has an ability to produce an organic acid and has been modified so that expression of yidE gene is enhanced, or a product obtained by processing the bacterium, to act on an organic raw material in a reaction mixture containing carbonate ions, bicarbonate ions, or carbon dioxide gas to produce the organic acid, and collecting the organic acid.

9 Claims, 3 Drawing Sheets

OTHER PUBLICATIONS

Riley, M., et al., "*Escherichia coli* K-12: a cooperatively developed annotation snapshot—2005," Nuc. Acids Res. 2006;34(1):1-9.

Torres, A. G., et al., "Differential Binding of *Escherichia coil* O157:H7 to Alfalfa, Human Epithelial Cells, and Plastic is Mediated by a Variety of Structures," Applied Environmen. Microbiol. 2005; 71(12):8008-8015.

Vemuri, G. N., et al., "Succinate production in dual-phase *Escherichia coil* fermentations depends on the time of transition from aerobic to anaerobic conditions," J. Ind. Microbiol. Biotechnol, 2002;28:325-332.

International Report on Patentability for PCT Patent App. No. PCT/JP2008/057397, Jun. 8, 2008.

* cited by examiner

METHOD FOR PRODUCING AN ORGANIC ACID

This application is a continuation under 35 U.S.C. §120 of PCT Patent Application No. PCT/JP2008/057397, filed Apr. 16, 2008, which claims priority under 35 U.S.C. §119 to Japanese Patent Application No. 2007-106909, filed on Apr. 16, 2007, and Japanese Patent Application No. 2007-242866, filed on Sep. 19, 2007, which are incorporated in their entireties by reference. The Sequence Listing in electronic format filed herewith is also hereby incorporated by reference in its entirety (File Name: US-411_Seq_List; File Size: 179 KB; Date Created: Oct. 15, 2009).

BACKGROUND OF THE INVENTION

1. Technical Field

The present invention relates to a method for producing an organic acid such as succinic acid using a bacterium.

2. Background Art

For the production of non-amino organic acids, including succinic acid, by fermentation, anaerobic bacteria are typically used, including bacteria belonging to the genus *Anaerobiospirillum* or *Actinobacillus* (U.S. Pat. Nos. 5,142,834 and 5,504,004, International Journal of Systematic Bacteriology (1999), 49, 207-216). Although such anaerobic bacteria provide high yields of products, many nutrients are required for their proliferation, and therefore it is necessary to add large amounts of organic nitrogen sources such as corn steep liquor (CSL) into the culture medium. The addition of large amounts of sources of organic nitrogen results in not only an increase in cost for the culture medium, but also an increase in the purification costs for isolating the product, and therefore it is not economical.

In addition, methods are known in which aerobic bacteria such as coryneform bacteria are cultured once under aerobic conditions to proliferate the bacterial cells, then the cells are harvested, washed, and allowed to rest so that a non-amino organic acid is produced without having to supply oxygen (Japanese Patent Laid-open (KOKAI) Nos. 11-113588 and 11-196888). These methods are economical, since organic nitrogen can be added in a smaller amount for proliferation of the bacterial cells, and the bacteria can sufficiently grow in a simple culture medium. However, there is still a room for improvement in terms of production amounts, concentration, and production rate per cell of the target organic acids as well as simplification of the production process, and the like. Furthermore, production of a non-amino organic acid by fermentation using a bacterium in which phosphoenolpyruvate carboxylase activity is enhanced (for example, Japanese Patent Laid-open No. 11-196887), and the like, has also been reported.

Furthermore, in the facultative anaerobic gram negative bacterium *Escherichia coli*, methods are known for producing a non-amino organic acid by culturing it once under aerobic conditions to allow for the growth of cells, and then culturing the resting cells without supplying oxygen to anaerobically produce the non-amino organic acid (Journal of Industrial Microbiology and Biotechnology (2002), 28 (6), 325-332), which is similar to the methods using coryneform bacteria. Also, the *Escherichia coli* bacteria can be aerobically cultured to aerobically produce the non-amino organic acid (U.S. Patent Published Application No. 20050170482). However, since *Escherichia coli* is a gram negative bacterium, it is vulnerable to osmotic pressure, and there remains room for improvement in productivity per cell etc.

The entire genome sequence of *Escherichia coli*, which belongs to the Enterobacteriaceae family, has been reported, and functions of putative protein-coding sequences have been predicted. The yidE gene is one of these putative protein-coding sequences, and although it is thought to code for a transporter, the actual function of this gene has not been clarified. Finally, the role of this gene in organic acid production has not been previously reported Nucleic Acid Research (2006), 34 (1), 1-9; Applied and Environmental Microbiology (2005), 71 (12), 8008-8015).

SUMMARY OF THE INVENTION

An aspect of the present invention is to provide a more efficient method for producing an organic acid using a bacterium, wherein higher yields are obtained.

It has been found that when using a bacterium which has been modified to enhance expression of the yidE gene, or a product obtained by processing the bacterium, the consumption rate of an organic raw material, generation rate of organic acid, or yield of organic acid increases.

It is an aspect of the present invention to provide a method for producing an organic acid comprising A) allowing a substance to act on an organic raw material in a reaction mixture containing carbonate ions, bicarbonate ions, or carbon dioxide gas, wherein the substance is selected from the group consisting of: i) a bacterium which has an ability to produce an organic acid and has been modified to have enhanced expression of the yidE gene is enhanced, ii) a product obtained by processing the bacterium of i), and iii) combinations thereof, and B) collecting the organic acid.

It is a further aspect of the present invention to provide the method as described above, wherein the enhanced expression is obtained by a method selected from the group consisting of: i) increasing the copy number of the yidE gene, ii) modifying an expression control sequence of the yidE gene, and iii) combinations thereof.

It is a further aspect of the present invention to provide the method as described above, wherein the yidE gene is selected from the group consisting of:

(a) a DNA comprising a nucleotide sequence selected from the group consisting of SEQ ID NO: 13, 15, 25, 27, 30 and 46, and (b) a DNA which hybridizes with a nucleotide sequence complementary to a nucleotide sequence selected from the group consisting of SEQ ID NO: 13, 15, 25, 27, 30 and 46 under stringent conditions, and said DNA improves the ability of the bacterium to produce an organic acid when expression of the DNA is enhanced in the bacterium.

It is a further aspect of the present invention to provide the method as described above, wherein the yidE gene codes for a protein selected from the group consisting of: A) a protein comprising an amino acid sequence selected from the group consisting of SEQ ID NO: 14, 16, 24, 26, 28, 29, 31, 47, 71 and 72, and B) a protein comprising an amino acid sequence selected from the group consisting of SEQ ID NO: 14, 16, 26, 28, 31 and 47, but which includes one or more substitutions, deletions, insertions or additions of one or several amino acid residues.

It is a further aspect of the present invention to provide the method as described above, wherein the bacterium belongs to the family Enterobacteriaceae.

It is a further aspect of the present invention to provide the method as described above, wherein the bacterium belongs to a genus selected from the group consisting of *Escherichia, Enterobacter, Raoultella, Klebsiella*, and *Pantoea*.

It is a further aspect of the present invention to provide the method as described above, wherein the bacterium is a rumen bacterium.

It is a further aspect of the present invention to provide the method as described above, wherein the bacterium is *Mannheimia succiniciproducens*.

It is a further aspect of the present invention to provide the method as described above, wherein the bacterium has been further modified to decrease an enzymatic activity selected from the group consisting of lactate dehydrogenase activity, alcohol dehydrogenase activity, pyruvate formate lyase activity, and combinations thereof.

It is a further aspect of the present invention to provide the method as described above, wherein the bacterium has been further modified so that pyruvate carboxylase activity is enhanced.

It is a further aspect of the present invention to provide the method as described above, wherein the organic acid is succinic acid.

It is an aspect of the present invention to provide a method for producing a succinic acid-containing polymer comprising A) producing succinic acid by a method as described above, and B) polymerizing the obtained succinic acid.

DETAILED DESCRIPTION OF THE PREFERRED EMBODIMENTS

Figure 1:
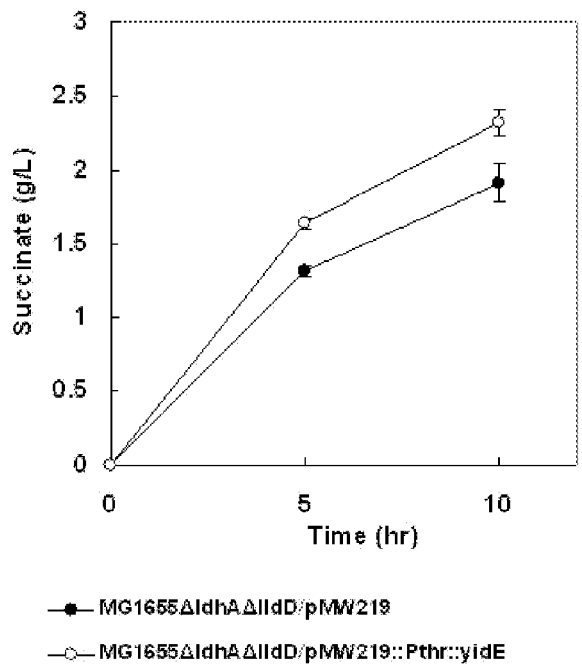
FIG. 1 shows the effect of yidE amplification in *Escherichia* bacterium MG1655ΔldhAΔlldD (change of succinic acid accumulation over time).

Hereinafter, embodiments of the presently disclosed subject matter will be explained in detail.

<1> Bacterium

The bacterium used in the method of the presently disclosed subject matter can be a bacterium which has an ability to produce an organic acid and has been modified so that expression of the yidE gene is enhanced. The term "organic acid-producing ability" can mean an ability of the bacterium to produce and accumulate an organic acid in a reaction mixture or in the cells of the bacterium to such a degree that the organic acid can be collected from the reaction mixture or cells when the bacterium is cultured in the reaction mixture. For example, the bacterium can accumulate a target organic acid in a medium or a reaction mixture in an amount of, for example, 0.5 g/L or more, or 1.0 g/L or more in another example. Such a bacterium can be obtained by modifying a parent bacterial strain that has an organic acid-producing ability to enhance expression of the yidE gene. When the parent strain does not have a native ability to produce an organic acid, the ability to produce an organic acid can be imparted to the parent strain and then modified so that expression of the yidE gene is enhanced. Furthermore, the ability to produce an organic acid can be imparted to a strain which has already been modified to enhance expression of the yidE gene. The organic acid-producing ability can be native to the chosen bacterium, or can be obtained by modifying the bacterium, such as those mentioned below, using mutation techniques or recombinant DNA techniques.

The organic acid can be a metabolic intermediate of the TCA cycle, and examples include, for example, succinic acid, malic acid, fumaric acid, citric acid, isocitric acid, cis-aconitic acid, and the like.

Although the parent strain of the bacterium which can be used to derive the bacterium as described in the presently disclosed subject matter is not particularly limited, bacteria belonging to the family Enterobacteriaceae, bacteria classified as rumen bacteria, and coryneform bacteria are examples.

The family Enterobacteriaceae encompasses bacteria belonging to the genera *Escherichia, Enterobacter, Erwinia, Klebsiella, Pantoea, Photorhabdus, Providencia, Raoultella, Salmonella, Serratia, Shigella, Morganella, Yersinia*, and the like. In particular, bacteria classified into the family Enterobacteriaceae according to the taxonomy used by the NCBI (National Center for Biotechnology Information) database (www.ncbi.nlm.nih.gov/Taxonomy/Browser/wwwtax.cgi?id=91347) are examples.

A "bacterium belonging to the genus *Escherichia*" can mean that the bacterium is classified into the genus *Escherichia* according to the classification known to a person skilled in the art of microbiology, although the bacterium is not particularly limited. Examples of the bacterium belonging to the genus *Escherichia* include but are not limited to, *Escherichia coli* (*E. coli*).

The bacterium belonging to the genus *Escherichia* is not particularly limited. However, examples include, for example, the bacteria of the phyletic groups described in the work of Neidhardt et al. (Neidhardt F. C. Ed., 1996, *Escherichia coli* and *Salmonella*: Cellular and Molecular Biology/Second Edition, pp. 2477-2483, Table 1, American Society for Microbiology Press, Washington, D.C.). Specific examples include *Escherichia coli* W3110 (ATCC 27325), *Escherichia coli* MG1655 (ATCC 47076) and the like, and others derived from the prototype wild-type strain, K12 strain.

These strains are available from, for example, the American Type Culture Collection (Address: 12301 10801 University Boulevard, Manassas, Va. 20108, United States of America). That is, registration numbers are given to each of the strains, and the strains can be ordered by using these numbers. The registration numbers of the strains are listed in the catalogue of the American Type Culture Collection.

*Pantoea* bacteria, *Erwinia* bacteria, and *Enterobacter* bacteria are classified as γ-proteobacteria, and they are taxonomically very close to one another (J. Gen. Appl. Microbiol., 1997, 43, 355-361; Int. J. Syst. Bacteriol., 1997, 43, 1061-1067). In recent years, some bacteria belonging to the genus *Enterobacter* were reclassified as *Pantoea agglomerans, Pantoea dispersa*, or the like, on the basis of DNA-DNA hybridization experiments etc. (Int. J. Syst. Bacteriol., 1989, 39:337-345). Furthermore, some bacteria belonging to the genus *Erwinia* were reclassified as *Pantoea ananas* or *Pantoea stewartii* (Int. J. Syst. Bacteriol., 1993, 43:162-173).

Examples of the *Enterobacter* bacteria include *Enterobacter agglomerans, Enterobacter aerogenes*, and the like. Specifically, the strains exemplified in European Patent Application Laid-open No. 952221 can be used. Typical strains of the genus *Enterobacter* include *Enterobacter agglomerans* ATCC 12287, *Enterobacter aerogenes* ATCC 13048, *Enterobacter aerogenes* NBRC 12010 (Biotechnol Bioeng., 2007, Mar. 27; 98(2):340-348), *Enterobacter aerogenes* AJ110637 (FERM ABP-10955), and the like. The AJ110637 strain was obtained from soil of seashore at Susuki Kaigan, Makinohara-shi, Shizuoka-ken on March, 2006 by cumulative liquid culture using glycerol as the carbon source.

The full length 16S rDNA sequence was then determined, and was found to be 99.9% homologousto that of the *Enterobacter aerogenes* NCTC 10006. Moreover, also in a physiological test using an API kit, this strain gave results similar to the prototype species of *Enterobacter aerogenes*, and therefore was identified as *Enterobacter aerogenes*. This strain was deposited at International Patent Organism Depository, Agency of Industrial Science and Technology (Central 6, 1-1, Higashi 1-Chome, Tsukuba-shi, Ibaraki-ken, 305-8566, Japan) on Aug. 22, 2007, and assigned an accession number of FERM P-21348. Then, the deposit was converted to an international deposit based on the Budapest Treaty on Mar. 13, 2008, and assigned a receipt number of FERM ABP-10955.

Typical strains of the *Pantoea* bacteria include *Pantoea ananatis, Pantoea stewartii, Pantoea agglomerans*, and *Pantoea citrea*. Specific examples include the following strains:

*Pantoea ananatis* AJ13355 (FERM BP-6614, European Patent Laid-open No. 0952221)

*Pantoea ananatis* AJ13356 (FERM BP-6615, European Patent Laid-open No. 0952221)

Although these strains are described as *Enterobacter agglomerans* in European Patent Laid-open No. 0952221, they are currently classified as *Pantoea ananatis* on the basis of nucleotide sequence analysis of the 16S rRNA etc., as described above.

Examples of the *Erwinia* bacteria include *Erwinia amylovora* and *Erwinia carotovora*, examples of the *Klebsiella* bacteria include *Klebsiella planticola*, and examples of the *Raoultella* bacteria include *Raoultella planticola*. Specific examples include the following strains:

*Erwinia amylovora* ATCC 15580 strain

*Erwinia carotovora* ATCC 15713 strain

*Klebsiella planticola* AJ13399 strain (FERM BP-6600, European Patent Laid-open No. 955368)

*Klebsiella planticola* AJ13410 strain (FERM BP-6617, European Patent Laid-open No. 955368).

*Raoultella planticola* ATCC 33531 strain

Although the AJ13399 strain and the AJ13410 strain were classified as *Klebsiella planticola* at the time of the deposit, *Klebsiella planticola* is currently classified into *Raoultella planticola* (Drancourt, M., 2001, Int. J. Syst. Evol. Microbiol, 51:925-32).

Examples of rumen bacteria can include *Mannheimia* bacteria, *Actinobacillus* bacteria, *Anaerobiospirillum* bacteria, *Pyrobacterium* bacteria, and *Selenomonas* bacteria. Bacteria including *Mannheimia succiniciproducens, Actinobacillus succinogenes, Selenomonas ruminantium, Veillonella parvula, Wolnella succinogenes*, and the like can be used. Specific strains of *Mannheimia succiniciproducens* can include *Mannheimia* sp. 55E strain (KCTC0769BP strain, U.S. Patent Published Application No. 20030113885, International Patent Publication WO2005/052135).

<1-1> Impartation of Organic Acid-Producing Ability

Hereinafter, methods for imparting an organic acid-producing ability to bacteria or methods for enhancing an organic acid-producing ability of bacteria are described.

To impart an ability to produce an organic acid, methods conventionally employed in the breeding of bacteria for producing substances by fermentation (see "Amino Acid Fermentation", Japan Scientific Societies Press, 1st Edition, published May 30, 1986, pp. 77-100) can be applied. Such methods include the acquisition of an auxotrophic mutant, an analogue-resistant strain, or a metabolic regulation mutant, or construction of a recombinant strain having enhanced expression of an enzyme involved in the biosynthesis of an organic acid. When breeding bacteria that produce an organic acid, one or more properties, such as an auxotrophic mutation, analogue resistance, or metabolic regulation mutation, can be imparted. The expression of one or more enzymes involved in the biosynthesis of an organic acid can be enhanced. Furthermore, imparting properties such as auxotrophy, analogue resistance, or metabolic regulation can be combined with the enhancing biosynthetic enzymes.

An auxotrophic mutant strain, a strain resistant to an organic acid analogue, or a metabolic regulation mutant strain which is able to produce an organic acid can be obtained by subjecting a parent or wild-type strain to a conventional mutagenesis, such as exposure to X-rays or UV irradiation, or a treatment with a mutagen such as N-methyl-N'-nitro-N-nitrosoguanidine, and then selecting the bacteria which exhibit an auxotrophy, analogue resistance, or metabolic regulation mutation and which also have the ability to produce an organic acid.

Methods for imparting the ability to produce succinic acid to bacteria, and succinic acid-producing bacteria, will be specifically exemplified below.

Succinic Acid-Producing Bacteria

As succinic acid-producing bacteria, strains that are unable to form acetic acid, lactic acid, ethanol and formic acid can be used, and specific examples include the *Escherichia coli* SS373 strain (International Patent Publication WO99/06532).

Strains that are unable to form acetic acid, lactic acid, ethanol and formic acid can be obtained by obtaining a strain that cannot assimilate acetic acid and lactic acid in a minimal medium, or by decreasing the activities of the lactic acid biosynthesis enzymes and acetic acid biosynthesis enzymes mentioned below (International Patent Publication WO2005/052135).

Moreover, such strains as described above can also be obtained by imparting resistance to monofluoroacetic acid (U.S. Pat. No. 5,521,075).

The ability to produce succinic acid can also be improved by imparting a glucose-assimilating ability under anaerobic conditions to a strain that is unable to produce both formic acid and lactic acid (International Patent Publication WO97/16528).

The ability to produce succinic acid can also be imparted by amplifying a gene which encodes an enzyme which is involved in the succinic acid biosynthesis system, or deleting a gene which encodes an enzyme which catalyzes a reaction which branches off from the succinic acid biosynthesis system to produce another compound.

The ability to produce succinic acid can also be imparted by modifying a bacterium to decrease the enzymatic activity of lactate dehydrogenase (LDH), which is a lactic acid biosynthesis system enzyme (International Patent Publications WO2005/052135, WO2005/116227, U.S. Pat. No. 5,770,435, U.S. Patent Published Application No. 20070054387, International Patent Publication WO99/53035, Alam, K. Y. and Clark, D. P., 1989, J. Bacteriol., 171:6213-6217). Some bacteria can have L-lactate dehydrogenase and D-lactate dehydrogenase, and such bacteria can be modified to decrease the activity of either one, or both, of the enzymes.

The ability to produce succinic acid can also be imparted by modifying a bacterium to decrease the enzymatic activity of the formic acid biosynthesis system enzyme, pyruvate-formate lyase (PFL) (U.S. Patent Published Application No. 20070054387, International Patent Publications WO2005/116227, WO2005/52135, Donnelly, M. I., Millard, C. S., Clark, D. P., Chen, M. J., Rathke, J. W., 1998, Appl. Biochem. Biotechnol., 70-72, 187-198.).

The ability to produce succinic acid can also be imparted by modifying a bacterium to decrease the enzymatic activities of phosphate acetyltransferase (PTA), acetate kinase (ACK), pyruvate oxidase (PDXB), acetyl-CoA synthetase (ACS) and acetyl-CoA hydrolase (ACH), which are acetic acid biosynthesis system enzymes (U.S. Patent Published Application No. 20070054387, International Patent Publications WO2005/052135, WO99/53035, WO2006/031424, WO2005/113745, and WO2005/113744).

The ability to produce succinic acid can also be enhanced by modifying a bacterium to decrease the enzymatic activity of alcohol dehydrogenase (ADH), which is an ethanol biosynthesis system enzyme (refer to International Patent Publication WO2006/031424).

The ability to produce succinic acid can also be enhanced by decreasing the activities of pyruvate kinase, glucose PTS (ptsG), ArcA protein, IclR protein (iclR), glutamate dehydrogenase (gdh) and/or glutamine synthetase (glnA), and glutamate synthase (gltBD) (International Patent Publication WO2006/107127, U.S. Patent Published Application No. 2007007933, Japanese Patent Laid-open No. 2005-168401). The gene abbreviations are in the parentheses following the enzyme names.

The ability to produce succinic acid can also be imparted by enhancing a biosynthesis system enzyme involved in succinic acid production.

The ability to produce succinic acid can also be enhanced by enhancing enzymatic activities of pyruvate carboxylase, malic enzyme, phosphoenolpyruvate carboxylase, fumarase, fumarate reductase, malate dehydrogenase and phosphoenolpyruvate carboxykinase (Japanese Patent Laid-open No. 11-196888, International Patent Publication WO99/53035, Hong, S. H., and S. Y. Lee, 2001, Biotechnol. Bioeng., 74:89-95, Millard, C. S. et al., 1996, Appl. Environ. Microbiol., 62:1808-1810, International Patent Publication WO2005/021770, Japanese Patent Laid-open No. 2006-320208, Kim, P. et al., 2004, Appl. Environ. Microbiol., 70:1238-1241). Enhancing the enzymatic activities of these target enzymes can be performed by referring to the methods for enhancing expression of the yidE gene described later.

Specific examples of succinic acid-producing bacteria belonging to the family Enterobacteriaceae include the following strains:

*Escherichia coli* S S373 strain (International Patent Publication WO99/06532)

*Escherichia coli* AFP111 strain (International Patent Publication WO97/16528)

*Escherichia coli* NZN111 strain (U.S. Pat. No. 6,159,738)

*Escherichia coli* AFP184 strain (International Patent Publication WO2005/116227)

*Escherichia coli* SBS100MG strain, SBS110MG strain, SBS440MG strain, SBS550MG strain, and SBS660MG strain (International Patent Publication WO2006/031424)

Examples of succinic acid-producing bacteria belonging to coryneform bacteria include the following strains:

*Brevibacterium flavum* AB-41 strain (Japanese Patent Laid-open No. 11-113588)

*Brevibacterium flavum* AB-41 strain (PC-amplified strain, Japanese Patent Laid-open No. 11-196888)

*Corynebacterium glutamicum* AJ110655 strain (FERM BP-10951)

*Brevibacterium flavum* MJ233Δldh strain (International Patent Publication WO2005/021770)

*Brevibacterium lactofermentum* (*Corynebacterium glutamicum*) 2256Δ(ldh, ach, pta, ack) (International Patent Publication WO2005/021770)

*Brevibacterium lactofermentum* 2256Δ(ldh, pta, ack, poxB) (International Patent Publication WO2005/113745)

*Corynebacterium glutamicum* Rldh-/pCRB-1 PC strain (International Patent Publication WO2005/010182)

Examples of succinic acid-producing bacteria belonging to rumen bacteria include the following strains:

*Mannheimia succiniciproducens* LPK, LPK7 and LPK4 (International Patent Publication WO2005/052135)

*Actinobacillus* succinogenes 130Z (U.S. Pat. No. 5,504,004)

*Anaerobiospirillum succiniciproducens* FZ10 (U.S. Pat. No. 5,521,075)

*Anaerobiospirillum succiniciproducens* FZ53 (U.S. Pat. No. 5,573,931)

<1-2> Enhancing Expression of the yidE Gene

The bacterium in accordance with the presently disclosed subject matter can be obtained by modifying a bacterium having an organic acid-producing ability such as those described above so that expression of the yidE gene is enhanced. However, the modification to enhance expression of the yidE gene is performed first, and then the ability to produce an organic acid can be imparted.

The yidE gene is thought to encode a kind of transporter (Riley, M. et al., 2006, Nucleic Acid Res., 34(1):1-9; Torres A. G. et al., 2005, Applied and Environmental Microbiology, 71 (12):8008-8015), and in addition, this gene codes for a protein which enhances an organic acid-producing ability of a bacterium when expression of this gene is enhanced. The degree of the enhancement of an organic acid-producing ability is not particularly limited, so long as productivity of the organic acid is improved as compared to an unmodified strain. However, the organic acid-producing ability is improved, for example, by 10% or more, 20% or more in another example, or 30% or more in another example, as compared to an unmodified strain.

The increase in expression of the yidE gene as compared to that of, for example, a wild-type or unmodified strain can be confirmed by comparing the amount of mRNA of yidE with that of the wild-type or unmodified strain.

To confirm the expression, exemplary methods include Northern hybridization and reverse transcriptase PCR(RT-PCR, Sambrook, J., and Russell, D. W., Molecular Cloning A Laboratory Manual/Third Edition, New York: Cold Spring Harbor Laboratory Press (2001)). The expression level of yidE can be increased to any level so long as the level is increased as compared to that of a wild-type or unmodified strain, and for example, it can be increased, for example, not less than 1.5 times, not less than 2 times in another example, or not less than 3 times in another example, as compared to that of, for example, a wild-type or an unmodified strain. Moreover, the increase in expression can also be confirmed on the basis of an increase in the amount of the target protein as compared to that in an unmodified or a wild-type strain, and it can be detected by, for example, Western blotting using an antibody (Sambrook, J., and Russell, D. W., Molecular Cloning A Laboratory Manual/Third Edition, New York: Cold Spring Harbor Laboratory Press (2001)).

Examples of the yidE gene can include yidE genes derived from enterobacteria, yidE genes derived from rumen bacteria, and homologues of these yidE genes. Examples can include yidE genes derived from *Escherichia* bacteria, yidE genes derived from *Enterobacter* bacteria, yidE genes derived from *Salmonella* bacteria, and the MS0288 or MS0289 gene derived from *Mannheimia* bacteria. Specific examples can also include the yidE gene derived from *Escherichia coli* MG1655 (SEQ ID NO: 13), the yidE gene derived from *Salmonella typhimurium* LT2 (SEQ ID NO: 15), the yidE gene derived from *Shigella flexneri* (SEQ ID NO: 25), the yidE gene derived from *Yersinia pestis* (SEQ ID NO: 27), the MS0288 gene derived from *Mannheimia succiniciproducens* (SEQ ID NO: 30), and the yidE gene derived from *Enterobacter aerogenes* AJ110637 (SEQ ID NO: 46). The yidE gene derived from *Enterobacter aerogenes* AJ110637 (SEQ ID NO: 46) and its encoded amino acid sequence (SEQ ID NO: 47) are novel sequences which have not been previously reported.

The yidE gene of *Escherichia coli* MG1655 is registered as b3685 in the genome sequence registered as GenBank Accession No. NC_000913 (amino acid sequence is GenBank Accession No. NP_418140). The yidE gene of *Salmonella typhimurium* LT2 is registered as STM3807 in the genome sequence registered as GenBank Accession No. NC_003197 (amino acid sequence is GenBank Accession No. NP_462707), and the yidE gene of *Mannheimia succiniciproducens* MBEL55E is registered as MS0288 or MS0289 in the genome sequence registered as GenBank Accession No. NC_006300 (amino acid sequence is GenBank Accession No. YP087480 (MS0288) or YP087481 (MS0289)). The yidE gene of the *Shigella flexneri* 8401 is registered as SFV3826 in the genome sequence registered as GenBank Accession No. NC_008258 (amino acid sequence is GenBank Accession No. YP_691142). The yidE gene of *Yersinia pestis* C092 is registered as YPO4083 in the genome sequence registered as GenBank Accession No. NC_003143 (amino acid sequence is GenBank Accession No. YP_407507).

A yidE gene homologue is a gene that can be derived from another microorganism, shows high homology to the yidE gene of *Escherichia coli*, and improves the ability to produce an organic acid when it is introduced into a host. The conserved sequence of the yidE proteins derived from *Salmonella typhimurium* and *Escherichia coli* is shown in SEQ ID NO: 24, and the conserved sequence of the yidE proteins derived from *Salmonella typhimurium*, *Escherichia coli*, and *Enterobacter aerogenes* AJ110637 is shown in SEQ ID NO: 71. The conserved sequence of the yidE proteins derived from *Escherichia coli*, *Yersinia pestis*, and *Shigella flexneri* is shown in SEQ ID NO: 29, and the conserved sequence of the yidE proteins derived from *Salmonella typhimurium*, *Escherichia coli*, *Yersinia pestis*, *Shigella flexneri*, and *Enterobacter aerogene* AJ110637 is shown in SEQ ID NO: 72. Examples of yidE gene homologues include genes coding for a protein having the amino acid sequence of SEQ ID NO: 24, 29, 71 or 72, or a protein having a homology of, for example, 80% or more, 90% or more in another example, 95% or more in another example, 98% or more in another example, or 99% or more in a another example, to the amino acid sequence of SEQ ID NO: 14, 16, 26, 28, 31 or 47, and which improves the ability to produce an organic acid of a host when it is introduced into the host. The yidE gene homologues coding for a protein having a homology of, for example, 80% or more, 90% or more in another example, 95% or more in another example, 98% or more in another example, or 99% or more in a another example, to the amino acid sequence of SEQ ID NO: 14, 16, 26, 28, 31 or 47 can have the consensus sequence of SEQ ID NOS: 24, 29, 71 or 72. Homology of amino acid sequences and nucleotide sequences can be determined by using, for example, the algorithm BLAST of Karlin and Altschul (Pro. Natl. Acad. Sci. USA, 90, 5873 (1993)) or FASTA (Methods Enzymol., 183, 63 (1990)). Programs called BLASTN and BLASTX have been developed on the basis of this algorithm BLAST (refer to www.ncbi.nlm.nih.gov). In this specification, the term "homology" can also refer to "identity".

Since sequences of the yidE gene from several different sources have already been reported as described above, the gene can be obtained by PCR using primers prepared on the basis of those nucleotide sequences. For example, a region including the yidE gene of *Escherichia coli* and a flanking region thereof, including a control region, can be obtained by PCR (polymerase chain reaction, see White, T. J. et al., Trends Genet., 5, 185 (1989)) using the primers shown in SEQ ID NOS: 9 and 10 and chromosomal DNA of *Escherichia coli* as the template. Homologues of yidE from other microorganisms can also be obtained in a similar manner.

Since the nucleotide sequence of the yidE gene can differ depending on the species or strains of enterobacteria, the yidE gene is not limited to a gene coding for the amino acid sequence of SEQ ID NO: 14, 16, 24, 26, 28, 29, 31, 47, 71 or 72, and it can be a mutant or artificially modified gene that codes for a protein having a sequence of SEQ ID NO: 14, 16, 26, 28, 31, 47 or 72, but which includes a conservative mutation, specifically, substitutions, deletions, insertions, additions, etc. of one or several amino acid residues at one or more positions so long as the ability to improve organic acid-producing ability of a bacterium when expression of the gene is enhanced is maintained. Although number meant by the term "one or several" can differ depending on positions in the three-dimensional structure of the protein or types of amino acid residues, it can be 1 to 20, 1 to 10 in another example, or 1 to 5 in another example. The substitutions, deletions, insertions, additions, inversions or the like of amino acid residues described above can also include those caused by naturally occurring mutations based on individual differences, differences in species of microorganisms that contain the yidE gene (mutant or variant), or the like.

The aforementioned substitution can be a conservative substitution that is a neutral substitution, that is, not resulting in a functional change. The conservative mutation is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of substitutions considered to be conservative substitutions can include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val.

Furthermore, as the yidE gene, a sequence encoding a protein having a homology not less than 80% in one example, 90% in another example, not less than 95% in another example, not less than 98% in another example, or not less than 99% in a another example, to the total amino acid sequence of SEQ ID NO: 14, 16, 26, 28, 31 or 47 and coding for a protein which improves organic acid-producing ability of a bacterium when expression is enhanced in the bacterium can be used. Furthermore, the degree of degeneracy of a gene varies depending on the hosts into which the gene is introduced, and therefore codons can be replaced with those which are favorable for the chosen host of the yidE gene. Moreover, the yidE gene can encode for a protein with an elongated or deleted N- or C-terminal sequence, so long as the gene improves the organic acid-producing ability of a bacterium when expression is enhanced in the bacterium. The length of the amino acid sequence to be elongated or deleted can be 50 or less, 20 or less in another example, 10 or less in another example, or 5 or less in a another example, in terms of number of amino acid residues. More specifically, the yidE gene can be a gene coding for a protein having the amino acid sequence of SEQ ID NO: 14, 16, 26, 28, 31 or 47 with elongation or deletion of 5 to 50 amino acid residues on the N-terminal or C-terminal side. For example, the products of the MS0288 and MS0289 genes derived from *Mannheimia* bacteria have 278 and 297 amino acid residues, respectively, and they are both quite a bit shorter than the yidE product of *Escherichia coli*, which has 554 amino acid residues. However, the MS0288 gene product has 74% homology to the C-terminal sequence of the yidE gene product derived from *Escherichia coli*, and the MS0289 gene product has 58% homology to the N-terminal sequence of the yidE gene product derived from *Escherichia coli*.

Genes homologous to the yidE gene as described above can be obtained by modifying a gene coding for the amino acid sequence of SEQ ID NO: 14, 16, 26, 28, 31 or 47 so that the protein encoded by the gene includes substitutions, deletions, insertions, or additions of amino acid residues at a specific site(s) by, for example, site-specific mutagenesis. Furthermore, homologous genes can also be obtained by conventionally known mutation treatments, such as those described below. Examples of the mutation treatments include treating the yidE gene with hydroxylamine or the like in vitro, and treating a microorganism, for example, a coryneform bacterium, containing the gene with ultraviolet ray irradiation or a mutagen typically used for mutation such as N-methyl-N'-nitro-N-nitrosoguanidine (NTG) or ethyl methanesulfonate (EMS). Furthermore, a mutation can be artificially introduced into the yidE gene by gene recombination using error-prone PCR (Cadwell, R. C., PCR Meth. Appl., 2, 28 (1992)), DNA shuffling (Stemmer, W. P., Nature, 370, 389 (1994)), or StEP-PCR (Zhao, H., Nature Biotechnol., 16, 258 (1998)) to obtain a highly active yidE gene.

Whether such homologous yidE genes code for a protein which improves organic acid-producing ability when expression is enhanced can be confirmed by, for example, introducing these genes into a wild-type strain of *Escherichia coli* or the like, and determining whether the organic acid-producing ability of the bacterium is improved or not. For example, by adding a reducing substance such as glucose and an organic acid such as malic acid to the medium, and comparing the amount of succinic acid or fumaric acid which is converted from the organic acid utilizing the reducing power which occurs when glucose is assimilated, the effect can be more clearly verified.

Examples of the yidE gene also include a DNA that hybridizes with a nucleotide sequence complementary to the sequence of SEQ ID NO: 13, 15, 25, 27, 30 or 46, or a probe that can be prepared from the sequences under stringent conditions, and codes for a protein which improves organic acid-producing ability of a bacterium when expression of the gene is enhanced in the bacterium. The "stringent conditions" are conditions under which a so-called specific hybrid is formed, and non-specific hybrid is not formed. Examples include, for example, conditions under which DNAs showing high homology to each other, for example, DNAs showing a homology of, for example, not less than 80%, not less than 90% in another example, not less than 95% in another example, or not less than 97% in a another example, hybridize with each other, and DNAs having homology lower than the above level do not hybridize with each other. Other examples include typical washing conditions in ordinary Southern hybridization, i.e., washing once, or twice or three times, at salt concentrations and temperatures of 1×SSC, 0.1% SDS at 60° C., 0.1×SSC, 0.1% SDS at 60° C. in another example, 0.1×SSC, 0.1% SDS at 65° C. in another example, or 0.1× SSC, 0.1% SDS at 68° C. in another example.

A partial sequence of a nucleotide sequence complementary to the sequence of SEQ ID NO: 13, 15, 25, 27, 30 or 46 can also be used as the probe. Such a probe can be prepared by PCR using oligonucleotides prepared on the basis of any one of these nucleotide sequences as primers and a DNA fragment containing any one of the sequences as the template. When a DNA fragment having a length of about 300 by is used as the probe, the washing conditions after hybridization under the aforementioned conditions can be exemplified by 2×SSC, 0.1% SDS at 50° C.

The aforementioned descriptions concerning gene homologues and conservative mutations can be similarly applied to the other enzyme genes described in this specification.

A bacterium can be modified so that the expression of the homologous yidE genes as described above is enhanced.

The expression "modified so that expression of yidE gene is enhanced" or "modified to enhance express of the yidE gene" can mean that the number of YidE protein molecules per cell is increased, or that the activity per YidE protein molecule is increased, etc., as compared to a parent strain or a wild-type strain. Examples of the wild-type strain that can be used for comparison include *Escherichia coli* strains MG1655, W3110, etc., which are derived from *Escherichia coli* K12, and *Enterobacter aerogenes* strains AJ110637, NBRC 12010, etc.

Expression of the yidE gene can be enhanced by increasing the copy number of the yidE gene. For example, the copy number of the gene can be increased by ligating a fragment containing the yidE gene to a vector that functions in the chosen bacterium, for example, a multi copy vector, to prepare a recombinant DNA, and transforming the bacterium which has an organic acid-producing ability as described above with the DNA. Alternatively, after such a recombinant DNA as described above is introduced into a wild-type strain of a bacterium, an organic acid-producing ability can be imparted to the transformed bacterium. The copy number of the gene can also be increased by transferring a single copy or multiple copies of the yidE gene to the bacterial chromosome. Transfer of the gene to the chromosome can be confirmed by Southern hybridization using a part of the yidE gene as a probe.

Expression of the yidE gene can also be enhanced by modifying an expression control sequence of the yidE gene. For example, the enhancement can be achieved by replacing a promoter sequence of the yidE gene with a stronger promoter, or by making a promoter sequence closer to a consensus sequence (WO00/18935).

Methods for constructing a bacterium having an organic acid-producing ability and modified so that expression of the yidE gene is enhanced are explained below. These methods can be performed as described in a manual such as Molecular Cloning (Cold Spring Harbor Laboratory Press, Cold Spring Harbor (USA), 2001).

Expression of the yidE gene can be enhanced by increasing the copy number by amplifying the yidE gene using a plasmid such as those described below. First, the yidE gene is cloned from the chromosome of *Escherichia coli* or the like by, for example, PCR. Chromosomal DNA can be prepared from a bacterium by, for example, the method of Saito and Miura (see H. Saito and K. Miura, Biochem. Biophys. Acta, 72, 619 (1963); Text for Bioengineering Experiments, Edited by the Society for Bioscience and Bioengineering, Japan, p 97-98, Baifukan Co., Ltd., 1992) or the like. Oligonucleotides for use in PCR can be synthesized on the basis of the aforementioned known information, for example, the synthetic oligonucleotides shown in SEQ ID NOS: 9 and 10 can be used to amplify the yidE gene.

A gene fragment including the yidE gene amplified by PCR can itself be amplified by inserting the fragment into a vector having a replication origin that enables autonomous replication in the chosen bacterium, then transform the bacterium with the vector. Examples of vectors which can be used to transform Enterobacteriaceae bacteria include pUC19, pUC18, pHSG299, pHSG399, pHSG398, RSF1010, pBR322, pACYC184, pMW219, and the like. When transforming coryneform bacteria, examples of plasmids that are autonomously replicable in coryneform bacteria include plasmid pCRY30 (Japanese Patent Laid-open No. 3-210184); plasmids pCRY21, pCRY2KE, pCRY2KX, pCRY31, pCRY3KE, and pCRY3KX (Japanese Patent Laid-open No. 2-72876 and U.S. Pat. No. 5,185,262); plasmids pCRY2 and pCRY3 (Japanese Patent Laid-open No. 1-191686); pAM330 (Japanese Patent Laid-open No. 58-67679); pHM1519 (Japanese Patent Laid-open No. 58-77895); pAJ655, pAJ611, and pAJ1844 (Japanese Patent Laid-open No. 58-192900); pCG1 (Japanese Patent Laid-open No. 57-134500); pCG2 (Japanese Patent Laid-open No. 58-35197); pCG4, pCG11, etc. (Japanese Patent Laid-open No. 57-183799); and pVK7 (Japanese Patent Laid-open No. 10-215883).

To prepare a recombinant DNA by ligating the yidE gene to a vector that functions in the chosen bacterium, the vector is digested with a restriction enzyme suitable for the ends of the yidE gene. Such a restriction enzyme site can be introduced in advance into the synthetic oligonucleotide which is used to amplify the yidE gene. Ligation is usually performed by using a ligase such as T4 DNA ligase.

In order to introduce a recombinant plasmid prepared as described above into a bacterium, any known transformation method reported to date be employed. For example, recipient cells can be treated with calcium chloride so as to increase permeability for the DNA, which has been reported for *Escherichia coli* K-12 (Mandel, M. and Higa, A., J. Mol. Biol., 53, 159 (1970)). Also, competent cells can be prepared from growing cells and DNA can be introduced into these cells, which has been reported for *Bacillus subtilis* (Duncan, C. H., Wilson, G. A. and Young, F. E., Gene, 1, 153 (1977)). Another method is to make DNA recipient cells into protoplasts or spheroplasts which easily take up a recombinant DNA, and a recombinant DNA can be introduced into these cells, which are known for *Bacillus subtilis*, actinomycetes, and yeasts (Chang, S, and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75, 1929 (1978)). In addition, transformation of bacteria can also be performed by the electric pulse method (Japanese Patent Laid-open No. 2-207791) or by the conjugal transfer method (Biotechnology (NY). 1991 January; 9(1):84-7).

The copy number of the yidE can also be increased by integrating multiple copies of the yidE gene into the chromosomal DNA of a bacterium, which can be accomplished by homologous recombination. This technique is performed by targeting a sequence which is present in multiple copies on the chromosomal DNA. Sequences present on the chromosomal DNA in multiple copies include a repetitive DNA or inverted repeats present at the end of a transposable element. Alternatively, as disclosed in Japanese Patent Laid-open No. 2-109985, multiple copies of the yidE gene can be introduced into a chromosomal DNA by incorporating them into a transposon and transferring it (Japanese Patent Laid-open Nos. 2-109985, 7-107976, Mol. Gen. Genet., 245, 397-405 (1994); Plasmid, 2000 November; 44(3): 285-91).

Expression of the yidE gene can also be enhanced by replacing a native expression control sequence, such as a promoter, of the yidE gene on the chromosomal DNA or a plasmid with a stronger promoter. Other methods include modifying a factor involved in expression control of the yidE gene such as operator or repressor, or ligating a strong terminator (Hamilton et al., Journal of Bacteriology 171:4617-4622; WO98/004715). For example, the lac promoter, trp promoter, trc promoter, tac promoter, PR promoter derived from λ-phage, lacUV promoter, and the like are known as strong promoters. Methods for evaluating the strength of promoters and examples of strong promoters are described in the paper of Goldstein et al. (Goldstein, M. A. and Doi, R. H., 1995, Biotechnol. Annu. Rev., 1, 105-128), and the like. Furthermore, as disclosed in WO00/18935, the strength of a promoter can be increased by making several nucleotide substitutions in the promoter region of a target gene so as to make the sequence closer to a consensus sequence. For example, the −35 region can be replaced with TTGACA or TTGCCA, and the −10 region can be replaced with TATAAT or TATAAC. In addition, it is known that the translation efficiency of mRNA is significantly affected by the substitution of several nucleotides in the spacer sequence between the ribosome-binding site (RBS) and the translation initiation codon, in particular, the sequence immediately upstream of the initiation codon, and therefore, such a sequence can be modified.

Expression of a gene can also be enhanced by extending the survival time of mRNA or by preventing degradation of the encoded protein in the cells. An expression control sequence such as a promoter which is upstream of the yidE gene can also be identified by using a promoter search vector or gene analysis software such as GENETYX. Expression of the yidE gene can be enhanced by such promoter substitution or modification.

Modifying a expression control sequence can be combined with increasing the copy number of the yidE gene.

A bacterial strain that is modified to decrease the activity of one or more enzymes such as lactate dehydrogenase (LDH), alcohol dehydrogenase (ADH), and pyruvate formate lyase (PFL), in addition to increasing the expression of the yidE gene, can be more effective. The expression "modified so that lactate dehydrogenase activity is decreased" can mean that the lactate dehydrogenase activity is decreased as compared to that of a strain in which lactate dehydrogenase is unmodified. The lactate dehydrogenase activity per cell can be decreased to 10% or lower as compared to that of a strain in which lactate dehydrogenase is unmodified. The lactate dehydrogenase activity can also be completely deleted. Decrease of the lactate dehydrogenase activity can be confirmed by measuring the lactate dehydrogenase activity by a known method (Kanarek, L. and Hill, R. L., 1964, J. Biol. Chem., 239:4202). Specific examples of a method for producing a mutant strain of *Escherichia coli* in which the lactate dehydrogenase activity is decreased include the method described in Alam, K.Y., and Clark, D. P., 1989, J. Bacteriol., 171:6213-6217, and the like. The bacterium in which lactate dehydrogenase activity is decreased and expression of the yidE gene is enhanced can be obtained by, for example, preparing a bacterium with a disrupted LDH gene, and transforming this bacterium with a recombinant vector containing the yidE gene, as described in Example 1. However, either the modification to decrease the LDH activity or the modification to enhance expression of the yidE gene can be performed first. In *Escherichia coli*, LDH is encoded by the ldhA and lldD genes. The DNA sequence of the ldhA gene is shown in SEQ ID NO: 20, and the encoded amino acid sequence is shown in SEQ ID NO: 21, the DNA sequence of the lldD gene is shown in SEQ ID NO: 22, and the encoded amino acid sequence is shown in SEQ ID NO: 23.

In order to decrease or delete the activity of LDH, a mutation can be introduced into the LDH gene on the chromosome by a typical mutagenesis method. For example, the gene coding for LDH on the chromosome can be deleted, or an expression control sequence such as a promoter and/or the Shine-Dalgarno (SD) sequence can be modified by gene recombination. Furthermore, a mutation which results in an amino acid substitution (missense mutation), a stop codon (nonsense mutation), or a frame shift mutation that adds or deletes one or two nucleotides into the LDH coding region on the chromosome can be introduced, or a part of the gene, or the entire gene can be deleted (Qiu Z. and Goodman M. F., 1997, J. Biol. Chem., 272:8611-8617). Furthermore, the LDH activity can also be decreased or deleted by gene disruption, for example, by mutating or deleting the coding region of the LDH gene, and replacing the normal or native LDH gene on the chromosome with the mutant LDH gene by homologous recombination or the like. Alternatively, a transposon or IS factor can be introduced into the gene.

In order to introduce a mutation that reduces or deletes the LDH activity by genetic recombination, for example, the following methods can be used. The LDH gene on the chromosome can be replaced with a mutant gene by preparing a mutant LDH gene in which a partial sequence of the LDH gene is modified so that it does not produce a functional LDH enzyme, and transforming a bacterium with a DNA containing the mutant gene to cause homologous recombination between the mutant gene and the gene on the chromosome. Such site-specific mutagenesis based on gene substitution utilizing homologous recombination has been already reported, and includes the methods of Red driven integration developed by Datsenko and Wanner (Proc. Natl. Acad. Sci. USA, 2000, vol. 97, No. 12, pp. 6640-6645), using a linear DNA in the Red driven integration in combination with an excision system derived from λ phage (Cho, E. H., Gumport, R. I., Gardner, J. F., J. Bacteriol., 184: 5200-5203 (2002)) (refer to WO2005/010175), using a plasmid containing a temperature sensitive replication origin (U.S. Pat. No. 6,303,383, Japanese Patent Laid-open No. 05-007491, WO2005/010175), and the like. Such site-specific mutagenesis based on gene substitution using homologous recombination as described above can also be performed with a plasmid that is unable to replicate in the chosen host.

The expression "modified so that alcohol dehydrogenase activity is decreased" can mean that the alcohol dehydrogenase activity is decreased as compared to that of a strain in which the alcohol dehydrogenase is unmodified. The alcohol dehydrogenase activity per cell can be reduced to 10% or lower as compared to that of a strain in which the alcohol dehydrogenase is unmodified. The alcohol dehydrogenase activity can also be completely deleted. Reduction of the alcohol dehydrogenase activity can be confirmed by measuring the alcohol dehydrogenase activity by a known method (Lutstorf, U. M., Schurch, P. M. & von Wartburg, J. P., Eur. J. Biochem., 17, 497-508 (1970)). Specific examples of the method for producing a mutant strain of *Escherichia coli* in which the alcohol dehydrogenase activity is decreased include the method described in Sanchez A. M. et al., 2005, Biotechnol. Prog., 21:358-365, and the like. A bacterium in which the alcohol dehydrogenase activity is decreased and expression of the yidE gene is enhanced can be obtained by, for example, preparing a bacterium in which the gene coding for alcohol dehydrogenase (ADH) is disrupted, and transforming this bacterium with a recombinant vector containing the yidE gene. However, either the modification for decreasing the ADH activity or the modification for enhancing expression of the yidE gene can be performed first. The alcohol dehydrogenase activity can be decreased by a method similar to the method for decreasing the lactate dehydrogenase activity described above. A partial nucleotide sequence of the ADH gene from the *Enterobacter aerogenes* AJ110637 strain (FERM ABP-10955) is shown in SEQ ID NO: 34. The entire nucleotide sequence of this gene can be determined by, for example, isolating the ADH gene (adhE) from the chromosomal DNA of *Enterobacter aerogenes* on the basis of the reported partial sequence.

The expression "modified so that pyruvate formate lyase activity is decreased" can mean that the pyruvate formate lyase activity is decreased as compared to that of a a strain in which the pyruvate formate lyase is unmodified. The pyruvate formate lyase activity per cell can be decreased to 10% or lower as compared to that of a a strain in which the pyruvate formate lyase is unmodified. The pyruvate formate lyase activity can also be completely deleted. The decrease of the pyruvate formate lyase activity can be confirmed by measuring the pyruvate formate lyase activity by a known method (Knappe, J. and Blaschkowski, H. P., 1975, Meth. Enzymol., 41:508-518). The bacterium in which pyruvate formate lyase activity is decreased and expression of the yidE gene is enhanced can be obtained by, for example, preparing a bacterium in which PFL gene is disrupted, and transforming this microorganism with a recombinant vector containing the yidE gene. However, either the modification for decreasing the PFL activity or the modification for enhancing expression of yidE can be performed first. The pyruvate formate lyase activity can be decreased by a method similar to the method for decreasing the lactate dehydrogenase activity described above.

A bacterium modified so that the pyruvate carboxylase (PC) activity is enhanced, in addition to the enhanced expression of the yidE gene can also be used. Enhancing the pyruvate carboxylase activity can be combined with decreasing the lactate dehydrogenase activity, alcohol dehydrogenase activity, and/or pyruvate formate lyase activity. The expression "modified so that pyruvate carboxylase activity is enhanced" can mean that the pyruvate carboxylase activity is increased as compared to that of an unmodified strain such as a wild-type strain or parent strain. The pyruvate carboxylase activity can be measured by, for example, by measuring the decrease in NADH.

As the PC gene, a gene for which the nucleotide sequence is already determined, or a gene obtained by isolating a DNA fragment encoding a protein having the PC activity from a chromosome of a microorganism, animal, plant, or the like and determining the nucleotide sequence, can be used. After the nucleotide sequence is determined, a gene synthesized on the basis of that sequence can also be used.

As the PC gene (pyc), for example, a PC gene derived from or native to a coryneform bacterium such as *Corynebacterium glutamicum* or *Brevibacterium flavum* (Peters-Wendisch, P. G. et al., 1998, Microbiology, vol. 144:915-927) (SEQ ID NO: 17) can be used.

PC genes from bacteria other than *Corynebacterium glutamicum*, as well as from other microorganisms, animals and plants, can also be used. In particular, the reported sequences of PC genes derived from microorganisms, animals and plants are described below (citations are indicated in brackets), and they can be obtained by hybridization or amplification of the ORF regions by PCR in the same manner as described above.

Human [Biochem. Biophys. Res. Comm., 202, 1009-1014, (1994)]

Mouse [Proc. Natl. Acad. Sci. USA., 90, 1766-1779, (1993)]

Rat [GENE, 165, 331-332, (1995)]

Yeast: *Saccharomyces cerevisiae* [Mol. Gen. Genet., 229, 307-315, (1991)],

*Schizosaccharomyces pombe* [DDBJ Accession No.; D78170]

*Bacillus stearothermophilus* [GENE, 191, 47-50, (1997)]

*Rhizobium etli* [J. Bacteriol., 178, 5960-5970, (1996)]

The PC gene can be enhanced in the same manner as those used for enhancing expression of the yidE gene as described above.

<2> Production method

An organic acid can be produced by using a bacterium that is able to produce an organic acid, and has been modified so that expression of the yidE gene is enhanced as described above. Specifically, an organic acid can be produced by allowing the bacterium, or a product obtained by processing the bacterium, to act on an organic raw material in a reaction mixture containing carbonate ions, bicarbonate ions, or carbon dioxide gas to produce the organic acid, and collecting the organic acid.

In one example of the method, by culturing the microorganism in a reaction mixture containing carbonate ions, bicarbonate ions, or carbon dioxide gas, and an organic raw material, proliferation of the microorganism and production of the organic acid occur simultaneously. In this example, a medium can be the reaction mixture. Proliferation of the microorganism and production of the organic acid can be simultaneously attained, or there can be a period during the culture when proliferation of the microorganism mainly occurs, and a period in which production of the organic acid mainly occurs.

In another example, by allowing cells to proliferate in a medium in the presence of carbonate ions, bicarbonate ions, or carbon dioxide gas, and an organic raw material, and thereby allowing the cells to act on the organic raw material in the medium or reaction mixture, an organic acid can be produced. In this example, a product obtained by processing the cells of the bacterium can also be used. Examples of a product obtained by processing the cells include, for example, immobilized cells which can be obtained with acrylamide, carragheenan, or the like, disrupted cells, centrifugation supernatant of the disrupted product, fraction obtained by partial purification of the supernatant by ammonium sulfate treatment or the like.

Although the bacteria can be cultured on a solid medium such as agar medium by slant culture, bacteria previously cultured in a liquid medium (seed culture) are other examples.

As the medium used for the culture, a typical microorganism culture medium can be used. For example, a typical medium obtained by adding natural nutrients such as meat extract, yeast extract and peptone, to a composition including inorganic salts such as ammonium sulfate, potassium phosphate and magnesium sulfate can be used.

In the aforementioned first example, the carbon source that is added to the medium also serves as the organic raw material for the production of the organic acid.

In the aforementioned second example, after the culture, the cells are collected by centrifugation, membrane separation, or the like, and used for the organic acid production reaction.

The organic raw material is not particularly limited so long as a carbon source, which the chosen microorganism can assimilate to produce succinic acid, is used. However, fermentable carbohydrates including carbohydrates such as galactose, lactose, glucose, fructose, glycerol, sucrose, saccharose, starch and cellulose, polyalcohols such as glycerin, mannitol, xylitol and ribitol, and the like are usually used. When the organic acid is succinic acid, fumaric acid or the like can be added in order to efficiently produce succinic acid as described in Japanese Patent Laid-open No. 5-68576, and malic acid can be added instead of fumaric acid.

Furthermore, a saccharified starch solution, molasses, or the like containing the fermentable carbohydrates can also be used. The fermentable carbohydrates can be used independently or in combination. Although the concentration of the aforementioned organic raw material is not particularly limited, it is more advantageous when the concentration is as high as possible within such a range that the production of the organic acid is not inhibited. In the aforementioned first example, concentration of the organic raw material in the medium is generally in the range of 5 to 30% (w/v), or 10 to 20% (w/v) in another example. Furthermore, in the aforementioned second example, the concentration of the organic raw material in the reaction mixture is generally in the range of 5 to 30% (w/v), or 10 to 20% (w/v) in another example. Furthermore, additional organic raw material can be added as its concentration decreases with progress of the reaction.

The aforementioned reaction mixture containing carbonate ions, bicarbonate ions, or carbon dioxide gas and the organic raw material is not particularly limited, and it can be, for example, a medium for culturing bacteria, or it can be a buffer such as phosphate buffer. The reaction mixture can be an aqueous solution containing a nitrogen source, inorganic salts, and the like. The nitrogen source is not particularly limited so long as it is a nitrogen source which the chosen bacterium can assimilate to produce an organic acid, and specific examples include various organic or inorganic nitrogen compounds such as ammonium salts, nitrates, urea, soybean hydrolysate, casein degradation products, peptone, yeast extract, meat extract, and corn steep liquor. Examples of the inorganic salts include various phosphates, sulfates, and metallic salts such as those of magnesium, potassium, manganese, iron, and zinc. If necessary, growth-promoting factors including vitamins such as biotin, pantothenic acid, inositol, and nicotinic acid, nucleotides, amino acids and the like can be added. In order to suppress foaming at the time of the reaction, an appropriate amount of commercially available antifoam can be added to the medium.

pH of the reaction mixture can be adjusted by adding sodium carbonate, sodium bicarbonate, potassium carbonate, potassium bicarbonate, magnesium carbonate, sodium hydroxide, calcium hydroxide, magnesium hydroxide, or the like. Since the pH for the reaction is usually 5 to 10, or 6 to 9.5 in another example, the pH of the reaction mixture is adjusted to be within the aforementioned range with an alkaline substance, carbonate, urea, or the like even during the reaction, if needed.

As the reaction mixture, water, buffer, medium or the like can be used, but a medium is particular example. The medium can contain, for example, the aforementioned organic raw material, and carbonate ions, bicarbonate ions, or carbon dioxide gas, and the reaction can be performed under anaerobic conditions. The carbonate or bicarbonate ions can be supplied from magnesium carbonate, sodium carbonate, sodium bicarbonate, potassium carbonate, or potassium bicarbonate, which can also be used as a neutralizing agent. However, if necessary, carbonate or bicarbonate ions can also be supplied from carbonic acid or bicarbonic acid or salts thereof or carbon dioxide gas. Specific examples of the salts of carbonic acid or bicarbonic acid include, for example, magnesium carbonate, ammonium carbonate, sodium carbonate, potassium carbonate, ammonium bicarbonate, sodium bicarbonate, potassium bicarbonate, and the like. Carbonate ions or bicarbonate ions can be added at a concentration of 0.001 to 5 M, 0.1 to 3 M in another example, or 1 to 2 M in another example. When carbon dioxide gas is present, it can be present in an amount of 50 mg to 25 g, 100 mg to 15 g in another example, or 150 mg to 10 g in another example, per liter of the solution.

The optimal growth temperature of the bacterium is generally in the range of 25 to 40° C. The reaction temperature is generally in the range of 25 to 40° C., or in the range of 30 to 37° C. in another example. The amount of bacterial cells in the reaction mixture can be, although it is not particularly limited, 1 to 700 g/L, 10 to 500 g/L in another example, or 20 to 400 g/L in another example. The reaction time can be 1 to 168 hours, or 3 to 72 hours in another example. The reaction can be performed batch-wise or on a column.

The bacterial culture can be performed under aerobic conditions. Alternatively, the organic acid production reaction can be performed under aerobic conditions, microaerobic conditions or anaerobic conditions. For the reaction under microaerobic conditions or anaerobic conditions, the reaction can be performed in a sealed reaction vessel without aeration, by supplying an inert gas such as nitrogen gas to the reaction mixture, by supplying an inert gas containing carbon dioxide gas to the reaction mixture, and the like.

The organic acid that accumulates in the reaction mixture (culture medium) can be separated and purified from the reaction mixture in a conventional manner. Specifically, solids such as bacterial cells can be removed by centrifugation, filtration, or the like, and then the resulting solution can be desalted with an ion exchange resin or the like. The organic acid can be separated and purified from the solution by crystallization or column chromatography.

Furthermore, when the target organic acid is succinic acid, after the succinic acid is produced, a polymerization reaction can be carried out by using the succinic acid as a raw material to produce a polymer containing succinic acid. In recent years, with the increase of environmentally friendly industrial products, polymers prepared from raw materials of plant origin have been attracting attention. Succinic acid can be converted into polymers such as polyesters and polyamides and used (Japanese Patent Laid-open No. 4-189822). Specific examples of succinic acid-containing polymers include succinic acid polyesters obtainable by polymerizing a diol such as butanediol, ethylene glycol, and succinic acid, succinic acid polyamides obtainable by polymerizing a diamine such as hexamethylenediamine and succinic acid, and the like. In addition, succinic acid and succinic acid-containing polymers and compositions containing these can be used for food additives, pharmaceutical agents, cosmetics, and the like.

EXAMPLES

Hereinafter, the present invention will be explained more specifically with reference to the following non-limiting examples.

Reference Example 1

Construction of L-, D-Lactate Dehydrogenase Gene-Deficient *Escherichia coli* Strain This gene was deleted by using the method called "Red-driven integration" developed by Datsenko and Wanner (Datsenko, K. A. and Wanner, B. L., 2000, Proc. Natl. Acad. Sci. USA, vol. 97, No. 12, pp. 6640-6645), and the λ phage excision system (Cho, E. H., Gumport, R. I., and Gardner, J. F., 2002, J. Bacteriol., 184 (18):5200-5203). According to this method, it is possible to construct a gene-disrupted strain in a single step by using a PCR product obtained with synthetic oligonucleotide primers in which a part of the target gene is present in the 5' end sequence and a part of an antibiotic resistance gene is present in the 3' end sequence. Furthermore, by using the λ phage excision system in combination, the antibiotic resistance gene which is integrated into the gene-disrupted strain can be removed.

<1-1> Construction of Strain Deficient in ldhA Gene Coding for D-Lactate Dehydrogenase According to the description of WO2005/010175, PCR was performed by using synthetic oligonucleotides having sequences corresponding to parts of the ldhA gene in the 5' end sequences and sequences corresponding to both ends of attL and attR of λ phage at the 3' end sequences as primers and plasmid pMW118-attL-Cm-attR as the template. pMW118-attL-Cm-attR is a plasmid obtained by inserting the attL and attR genes, which are the attachment sites of λ phage, and the cat gene, which is a chloramphenicol resistance gene, into pMW118 (Takara Bio), and the genes are inserted in the order of attL-cat-attR. The sequences of the synthetic oligonucleotides used as the primers are shown in SEQ ID NOS: 1 and 2. The amplified PCR product was purified on an agarose gel and introduced into *Escherichia coli* MG1655 strain containing the plasmid pKD46, which is capable of temperature-sensitive replication by electroporation. Then, an ampicillin-sensitive strain not harboring pKD46 was obtained, and deletion of the ldhA gene was confirmed by PCR. PCR was performed by using the synthetic oligonucleotides shown in SEQ ID NOS: 3 and 4 as primers. Whereas the PCR product obtained for the parent strain had a size of about 1.2 kb, the deficient strain showed a band with a size of about 1.9 kb.

To eliminate the att-cat gene introduced into the ldhA gene, the strain was transformed with the helper plasmid pMW-intxis-ts, and an ampicillin resistant strain was selected. The pMW-intxis-ts contains the λ phage integrase (Int) gene and excisionase (Xis) gene and shows temperature-sensitive replication. Then, the strain in which att-cat and pMW-intxis-ts were eliminated was confirmed by PCR on the basis of ampicillin sensitivity and chloramphenicol sensitivity. PCR was performed by using the synthetic oligonucleotides shown in SEQ ID NOS: 3 and 4 as primers. Whereas the PCR product obtained for the strain in which att-cat remained had a size of about 1.9 kb, a band of about 0.3 kb was observed for the strain in which att-cat was eliminated. The ldhA deficient strain obtained as described above was designated as MG1655ΔldhA strain.

<1-2> Construction of Strain Deficient in lldD Gene Coding for L-Lactate Dehydrogenase A strain was constructed in the same manner as that of the construction of the ldhA gene-deficient strain. PCR was performed by using synthetic oligonucleotides having sequences corresponding to parts of the lldD gene in the 5' end sequences and sequences corresponding to both ends of attL and attR of λ phage in the 3' end sequences as primers and plasmid pMW118-attL-Cm-attR as the template. The sequences of the synthetic oligonucleotides used as the primers are shown in SEQ ID Nos. 5 and 6. The amplified PCR product was purified on an agarose gel and introduced into the *Escherichia coli* MG1655ΔldhA strain containing plasmid pKD46, which is capable of temperature-sensitive replication by electroporation. Then, an ampicillin-sensitive strain not harboring pKD46 was obtained, and the deletion of the lldD gene was confirmed by PCR. PCR was performed by using the synthetic oligonucleotides shown in SEQ ID NOS: 7 and 8 as primers. Whereas the PCR product obtained for the parent strain had a size of about 1.4 kb, a band of about 1.9 kb should be observed for the deficient strain.

To eliminate the att-cat gene introduced into the lldD gene, the strain was transformed with the helper plasmid pMW-intxis-ts, and an ampicillin resistant strain was selected. Then, the strain in which att-cat and pMW-intxis-ts were eliminated was obtained on the basis of ampicillin sensitivity and chloramphenicol sensitivity, and confirmed by PCR. PCR was performed by using the synthetic oligonucleotides shown in SEQ ID NOS: 7 and 8 as primers. Whereas the PCR product obtained for the strain in which att-cat remained had a size of about 1.9 kb, a band of about 0.3 kb was observed for the strain in which att-cat was eliminated. The lldD deficient strain obtained as described above was designated as MG1655ΔldhAΔlldD strain.

Example 1

Construction of yidE Gene-Enhanced Strain of Succinic Acid-Producing Bacterium

<1-1> Construction of a Plasmid for Gene Amplification

In order to amplify the yidE gene, plasmid pMW219::Pthr was used. This plasmid corresponds to the vector pMW219 (Nippon Gene) which has the promoter region of the threonine operon (thrLABC) from the genome of the *Escherichia coli* shown in SEQ ID NO: 11 at the HindIII site and BamHI site, and enables amplification of a gene by cloning the gene at a position in the plasmid downstream from that promoter.

<1-2> Construction of a Plasmid for Enhancing yidE Gene Derived from *Escherichia coli*

PCR was performed by using the synthetic oligonucleotide having a BamHI site shown in SEQ ID NO: 12 as a 5' primer, the synthetic oligonucleotide having a BamHI site shown in SEQ ID NO: 19 as a 3' primer. These primers were prepared on the basis of the nucleotide sequence of the yidE gene in the genome sequence of *Escherichia coli* (GenBank Accession No. U00096 b3685). The genomic DNA of *Escherichia coli* MG1655 strain was used as the template, and PCR product was treated with the restriction enzyme BamHI to obtain a gene fragment containing the yidE gene. The fragment was purified and ligated with the vector pMW219::Pthr which had been previously treated with BamHI to construct plasmid pMW219::Pthr::yidE for yidE amplification.

<1-3> Production of yidE-Amplified Strain pMW219::Pthr::yidE obtained in <1-2> described above and pMW219 were used to transform the *Escherichia coli* MG1655ΔldhAΔlldD strain by the electric pulse method, and the transformants were applied to the LB agar medium containing 25 μg/ml of kanamycin, and cultured at 37° C. for about 18 hours. The colonies which appeared were purified, and plasmids were extracted from them in a conventional manner to confirm introduction of the target plasmid. The obtained strains were designated as MG1655ΔldhAΔlldD/pMW219::Pthr::yidE and MG1655ΔldhAΔlldD/pMW219, respectively. The *Enterobacter aerogenes* AJ110637 strain was also transformed with pMW219::Pthr::yidE and pMW219 by the electric pulse method, and the transformants were applied to the LB agar medium containing 50 μg/ml of kanamycin, and cultured at 37° C. for about 18 hours. The colonies which appeared were purified, and plasmids were extracted from them in a conventional manner to confirm introduction of the target plasmid. The obtained strains were designated as AJ110637/pMW219::Pthr::yidE and AJ110637/pMW219, respectively.

Example 2

Effect of yidE Amplification

<2-1> Effect of yidE Amplification in Succinic Acid-Producing Strain of *Escherichia bacterium*

MG1655ΔldhAΔlldD/pMW219::Pthr::yidE and MG1655ΔldhAΔlldD/pMW219 were each uniformly applied to an LB plate containing 25 μg/ml of kanamycin, and cultured at 37° C. for 16 hours. Then, each plate was incubated at 37° C. for 16 hours under anaerobic conditions by using Anaeropack (Mitsubishi Gas Chemical). The obtained cells on the plate were washed with 0.8% brine, and then diluted 51 times, and thereby a cell suspension having OD=1.0 (600 nm) was prepared. This cell suspension in a volume of 100 μl and a production medium (10 g/l of glucose, 10 g/l 2Na malate, 45.88 g/l of TES, 6 g/l of $Na_2HPO_4$, 3 g/l of $KH_2PO_4$, 1 g/l of $NH_4Cl$, adjusted to pH 7.3 with KOH and filtrated) in a volume of 1.3 ml in which dissolved gases in the medium were replaced with nitrogen gas by bubbling nitrogen gas beforehand were put into 1.5-ml volume micro tubes, and the cells were cultured at 31.5° C. for 10 hours by using a stirrer for micro tubes. After the culture, the amount of succinic acid which accumulated in the medium was analyzed by liquid chromatography. Two of Shim-pack SCR-102H (Shimadzu) connected in series were used as the column, and a sample was eluted at 50° C. with 5 mM p-toluenesulfonic acid. The eluate was neutralized with 20 mM Bis-Tris aqueous solution containing 5 mM p-toluenesulfonic acid and 100 μM EDTA, and succinic acid was quantified by measuring electric conductivity with CDD-10AD (Shimadzu).

The amounts of succinic acid which accumulated after 10 hours are shown in Table 1, and change of succinic acid accumulation with time is shown in FIG. 1.

TABLE 1

| Effect of yidE amplification in succinic acid-producing strain, MG1655ΔldhAΔlldD | |
|---|---|
| Strain | Succinate (g/L) |
| MG1655ΔldhAΔlldD/pMW219 | 1.91 (±0.13) |
| MG1655ΔldhAΔlldD/pMW219::Pthr::yidE | 2.32 (±0.09) |

Succinic acid accumulation was markedly increased in the yidE gene-amplified strain MG1655ΔldhAΔlldD/pMW219::Pthr::yidE as compared to the control MG1655ΔldhAΔlldD/pMW219, and on the basis of this result, the effect of enhancement of yidE expression on succinic acid production was confirmed.

<2-2> Effect of yidE Amplification in *Enterobacter* Bacterium

AJ110637/pMW219::Pthr::yidE and AJ110637/pMW219 were each uniformly applied to an LB plate containing 50 μg/ml of kanamycin, and cultured at 37° C. for 16 hours. Then, each plate was incubated at 37° C. for 16 hours under anaerobic conditions by using Anaeropack (Mitsubishi Gas Chemical). The obtained cells on the plate were washed with 0.8% brine, and then diluted 51 times, and thereby a cell suspension having OD=1.0 (600 nm) was prepared. This cell suspension in a volume of 100 μl and a production medium (10 g/l of glucose, 10 g/l 2Na malate, 45.88 g/l of TES, 6 g/l of $Na_2HPO_4$, 3 g/l of $KH_2PO_4$, 1 g/l of $NH_4Cl$, adjusted to pH 7.3 with KOH and filtrated) in a volume of 1.3 ml in which dissolved gases in the medium were replaced with nitrogen gas by bubbling nitrogen gas beforehand were put into 1.5-ml volume micro tubes, and the cells were cultured at 31.5° C. for 6 hours by using a stirrer for micro tubes. After the culture, the amount of succinic acid which accumulated in the medium was analyzed by liquid chromatography. Two Shim-pack SCR-102H (Shimadzu) connected in series were used as the column, and a sample was eluted at 50° C. with 5 mM p-toluenesulfonic acid. The eluate was neutralized with 20 mM Bis-Tris aqueous solution containing 5 mM p-toluenesulfonic acid and 100 μM EDTA, and succinic acid was quantified by measuring electric conductivity with CDD-10AD (Shimadzu).

Figure 2:
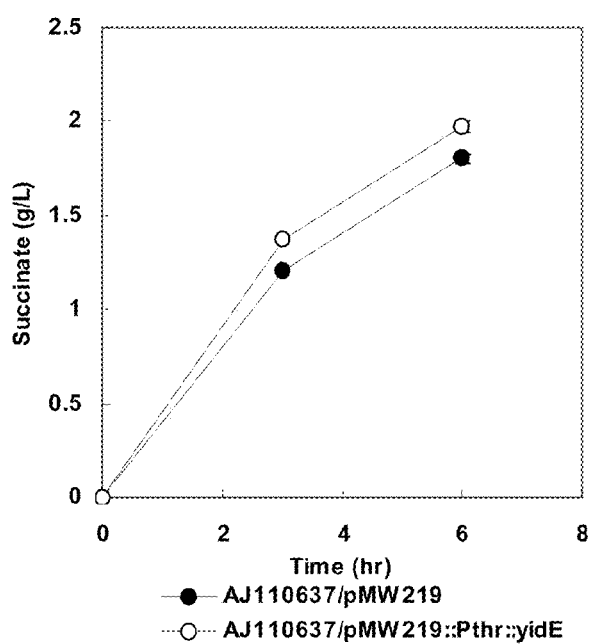
FIG. 2 shows the effect of yidE amplification in *Enterobacter* bacterium AJ110637 strain (change of succinic acid accumulation over time).

The amounts of succinic acid which accumulated after 6 hours are shown in Table 2, and the change of succinic acid accumulation with time is shown in FIG. 2.

Succinic acid accumulation was markedly increased in the yidE gene-amplified strain AJ110637/pMW219::Pthr::yidE as compared to AJ110637/pMW219 as the control.

TABLE 2

Effect of yidE amplification in AJ110637 strain

| Strain | Succinate (g/L) |
|---|---|
| AJ110637/pMW219 | 1.81 (±0.04) |
| AJ110637/pMW219::Pthr::yidE | 1.98 (±0.05) |

Example 3

<3-1> Construction of adhE-Deficient Strain of *Enterobacter aerogenes* AJ110637

When *Enterobacter aerogenes* AJ110637 is grown in a medium containing a sugar source under anaerobic conditions, it produces a marked amount of ethanol. Therefore, adhE coding for alcohol dehydrogenase was deleted to suppress generation of ethanol.

A gene fragment for deletion of adhE was prepared by PCR using the plasmid pMW-attL-Tc-attR described in WO2005/010175 as the template and oligonucleotides of SEQ ID NOS: 32 and 33 as primers. pMW118-attL-Tc-attR is a plasmid obtained by inserting the attL and attR genes, which are the attachment sites of λ phage, and the Tc gene, which is a tetracycline resistance gene, into pMW118 (Takara Bio), and the genes are inserted in the order of attL-Tc-attR (see Reference Example 3). By PCR described above, a gene fragment containing a tetracycline resistance gene, attL and attR site of λ phage at the both ends of tetracycline gene, and 60 by upstream sequence and 59 by downstream sequence of the adhE gene added to the outer ends of the λ phage sequences was amplified. This fragment was purified by using Wizard PCR Prep DNA Purification System (Promega).

Figure 3:
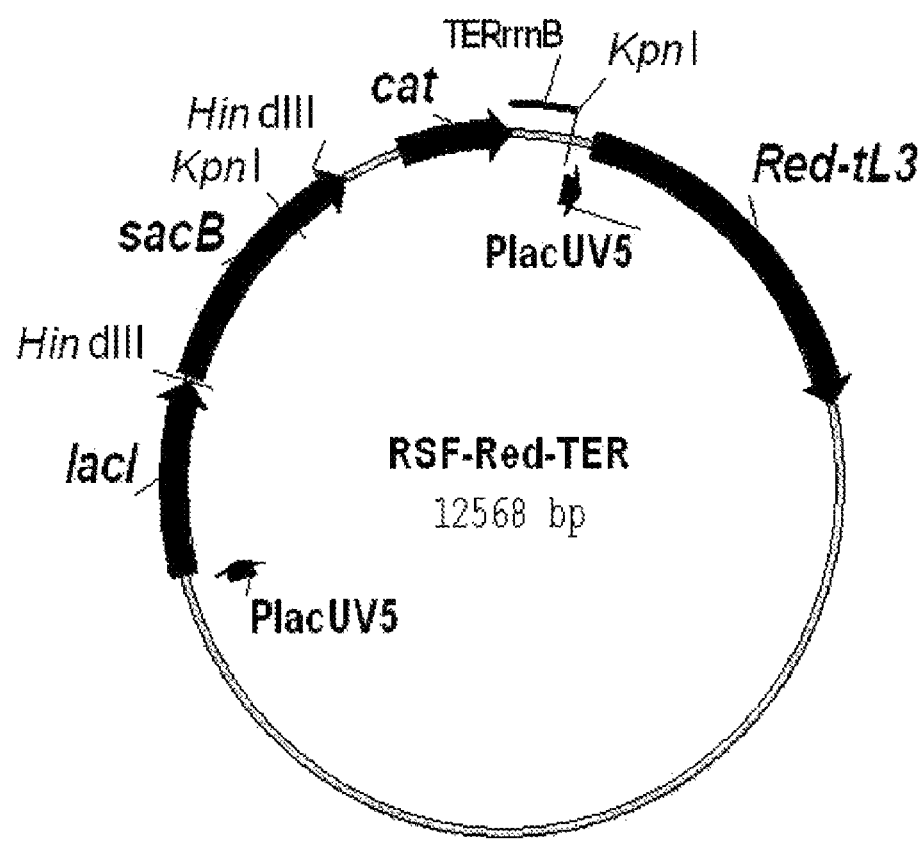
FIG. 3 shows the structure of RSF-Red-TER.

Then, the *Enterobacter aerogenes* AJ110637 strain was transformed with RSF-Red-TER (see FIG. 3, Reference Example 2) to obtain *Enterobacter aerogenes* AJ110637/RSF-Red-TER strain. This strain was cultured overnight in the LB medium containing 40 μg/mL of chloramphenicol, the culture medium was inoculated in a 1/100 volume to 50 mL of the LB medium containing 40 μg/mL of chloramphenicol and 0.4 mM isopropyl-β-D-thiogalactopyranoside, and culture was performed at 31° C. for 4 hours. The cells were collected, washed three times with ice-cooled 10% glycerol, and finally suspended in 0.5 mL of 10% glycerol. The suspended cells were used as competent cells, and the PCR fragment prepared in the above section was introduced into the cells by using GENE PULSER II (BioRad) under the conditions of a field strength of 20 kV/cm, capacitor capacity of 25 μF and resistance of 200Ω. Ice-cooled LB medium was added to the cell suspension, and culture was performed at 31° C. for 2 hours with shaking. Then, the culture was applied to LB plate containing 25 μg/mL of tetracycline. The colonies that appeared were purified with the same plate, and then it was confirmed by PCR that the adhE gene was replaced with the tetracycline resistance gene.

<3-2> Construction of Pyruvate Carboxylase Gene-Enhanced Strain of AJ110637ΔadhE Strain An ability to produce succinic acid was imparted to the *Enterobacter aerogenes* AJ110637ΔadhE strain by amplifying pyc coding for pyruvate carboxylase derived from *Corynebacterium glutamicum* in that strain.

In order to express pyc derived from *Corynebacterium glutamicum* in the AJ110637ΔadhE strain, it was attempted to obtain a threonine operon promoter fragment from the *Escherichia coli* MG1655 strain. The entire genomic nucleotide sequence of *Escherichia coli* (*Escherichia coli* K-12 strain) has already been reported (Genbank Accession No. U00096, Science, 277, 1453-1474 (1997)). On the basis of this sequence, PCR amplification of the promoter region of the threonine operon (thrLABC) was performed. PCR was performed by using the synthetic oligonucleotide having an SacI site shown in SEQ ID NO: 35 as a 5' primer, the synthetic oligonucleotide shown in SEQ ID NO: 36 as a 3' primer, and the genomic DNA of *Escherichia coli* MG1655 strain (ATCC 47076, ATCC 700926) as the template to obtain a threonine operon promoter fragment (A) (SEQ ID NO: 37).

Furthermore, a pyc gene fragment derived from the *Corynebacterium glutamicum* 2256 strain (ATCC 13869) was obtained. PCR was performed by using the synthetic oligonucleotide shown in SEQ ID NO: 38 as a 5' primer, the synthetic oligonucleotide having a SacI site shown in SEQ ID NO: 39 as a 3' primer, and the genomic DNA of the *Corynebacterium glutamicum* 2256 strain (ATCC 13869) as the template to obtain a pyc gene fragment (B) (SEQ ID NO: 40).

PCR was performed by using the fragments (A) and (B) as templates, the primers of SEQ ID NOS: 35 and 39 to obtain a gene fragment (C) consisting of the fragments (A) and (B) ligated to each other. This gene fragment (C) was treated with the restriction enzyme SacI, and purified, and the product was ligated with the plasmid vector pSTV28 (Takara Bio) digested with the restriction enzyme SacI to construct a plasmid pSTV28::Pthr::pyc for pyc amplification.

The plasmid pSTV28::Pthr::pyc for pyc amplification was introduced into the aforementioned *Enterobacter aerogenes* AJ110637ΔadhE strain by electroporation to obtain a transformant exhibiting tetracycline and chloramphenicol resistance. This pyc-amplified strain of *Enterobacter aerogenes* AJ110637ΔadhE was designated as AJ110637ΔadhE/pSTV28::Pthr::pyc.

<3-3> Construction of *Enterobacter aerogenes* yidE Gene-Enhanced Strain of AJ110637ΔadhE/pSTV28::Pthr::pyc In the same manner as that described above, PCR amplification of the promoter region of the threonine operon (thrLABC) of *Escherichia coli* (*Escherichia coli* K-12 strain) was performed. PCR was performed by using the synthetic oligonucleotide shown in SEQ ID NO: 41 as a 5' primer, the synthetic oligonucleotide shown in SEQ ID NO: 42 as a 3' primer, and the genomic DNA of *Escherichia coli* MG1655 strain (ATCC 47076, ATCC 700926) as the template to obtain a threonine operon promoter fragment (A) (SEQ ID NO: 43).

Furthermore, in order to clone the yidE gene of the *Enterobacter aerogenes* AJ110637 strain, PCR was performed by using the synthetic oligonucleotide shown in SEQ ID NO: 44 as a 5' primer, the synthetic oligonucleotide shown in SEQ ID NO: 45 as a 3' primer, and the genomic DNA of the *Enterobacter aerogenes* AJ110637 strain as the template to obtain a yidE gene fragment (B) (SEQ ID NO: 46).

PCR was performed by using the fragments (A) and (B) as templates, and the primers of SEQ ID NOS: 41 and 45 to obtain a gene fragment (C) consisting of the fragments (A) and (B) ligated to each other. This gene fragment (C) was blunt-ended by using TaKaRa BKL Kit (Takara Bio), and the 5' end was phosphorylated. Then, the fragment was digested with the restriction enzyme SmaI, and the product was ligated with the plasmid vector pMW218 dephosphorylated with alkaline phosphatase to construct a plasmid pMW218::Pthr::Ent-yidE for yidE amplification.

The aforementioned vector pMW218::Pthr::Ent-yidE for amplification of the yidE gene derived from the *Enterobacter aerogenes* AJ110637 strain, and the control plasmid pMW218 were each introduced into the *Enterobacter aerogenes* AJ110637ΔadhE/pSTV28::Pthr::pyc strain by electroporation to obtain transformants exhibiting tetracycline, chloramphenicol and kanamycin resistance. The yidE-amplified strain derived from the *Enterobacter aerogenes* AJ110637ΔadhE/pSTV28::Pthr::pyc strain was designated as AJ110637ΔadhE/pSTV28::Pthr::pyc/pMW218::Pthr::Ent-yidE, and the pMW218-introduced strain as a control was designated as AJ110637ΔadhE/pSTV28::Pthr::pyc/pMW218.

<3-4> Effect of Amplification of yidE Derived from *Enterobacter aerogenes* in *Enterobacter* Bacterium AJ110637ΔadhE/pSTV28::Pthr::pyc/pMW218::Pthr::Ent-yidE, and AJ110637ΔadhE/pSTV28::Pthr::pyc/pMW218 were each uniformly applied to a LB plate containing 50 μg/ml of kanamycin, 25 μg/ml of tetracycline, and 40 μg/ml of chloramphenicol, and cultured at 31.5° C. for 16 hours. Then, the cells were inoculated into 3 ml of a seed medium (20 g/l of Bacto tryptone, 10 g/l of yeast extract, 20 g/L of NaCl) contained in a test tube, and cultured at 31.5° C. for 16 hours with shaking. A succinic acid production medium (100 g/l of glucose, 50 g/L of calcium carbonate subjected to hot air sterilization for 3 hours or more) in a volume of 3 ml was added to the medium obtained above, then the tube was sealed with a silicone stopper, and culture was performed at 31.5° C. for 24 hours with shaking. After the culture, the amount of succinic acid which accumulated in the medium was analyzed by liquid chromatography. Two Shimpack SCR-102H (Shimadzu) connected in series were used as the column, and a sample was eluted at 50° C. with 5 mM p-toluenesulfonic acid. The eluate was neutralized with 20 mM Bis-Tris aqueous solution containing 5 mM p-toluenesulfonic acid and 100 μM EDTA, and succinic acid was quantified by measuring electric conductivity with CDD-10AD (Shimadzu).

The amounts of succinic acid which accumulated after 24 hours are shown in Table 3.

Succinic acid accumulation markedly increased in the yidE gene-amplified strain AJ110637ΔadhE/pSTV28::Pthr::pyc/pMW218::Pthr::Ent-yidE as compared to AJ110637ΔadhE/pSTV28::Pthr::pyc/pMW218 as the control.

TABLE 3

|  | AJ110637ΔadhE/ pSTV28::Pthr::pyc/ pMW218 | AJ110637ΔadhE/ pSTV28::Pthr::pyc/ pMW218::Pthr::Ent-yidE |
|---|---|---|
| Consumed glucose amount (g/L) | 9.53 (±1.85) | 9.23 (±1.46) |
| OD (600 nm) | 8.90 (±0.18) | 8.57 (±0.56) |
| Succinic acid accumulation (g/L) | 3.40 (±0.56) | 5.12 (±1.56) |
| Succinic acid yield based on consumed glucose (%) | 35.80 (±1.82) | 54.80 (±12.81) |

Reference Example 2

Construction of Helper Plasmid RSF-Red-TER

Figure 4:
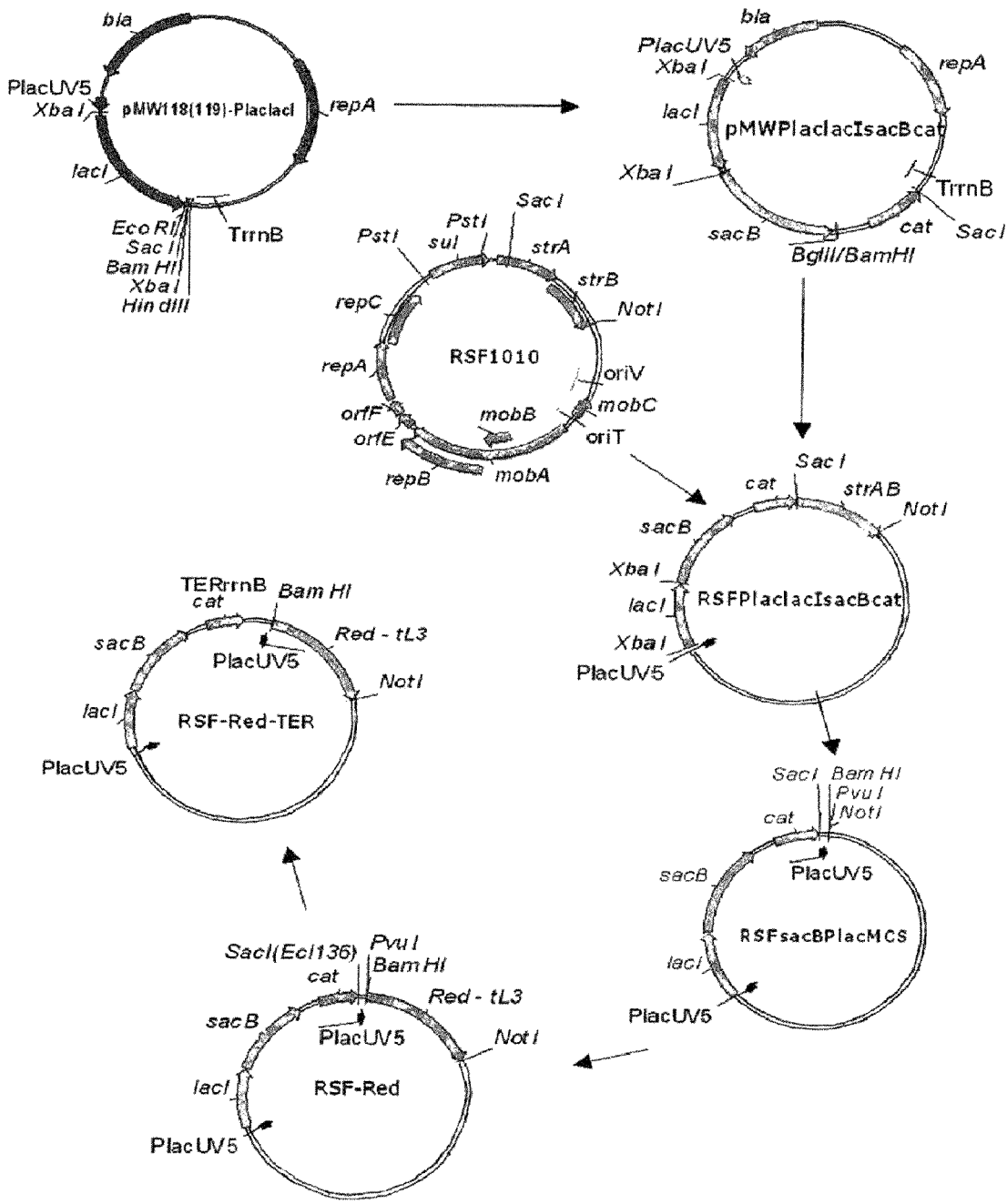
FIG. 4 shows the construction scheme of RSF-Red-TER.

The scheme for constructing the helper plasmid RSF-Red-TER is shown in FIG. 4.

As the first step of the construction, an RSFsacBPlacMCS vector was designed. For this purpose, DNA fragments containing the cat gene of the pACYC184 plasmid and the structural region of the sacB gene of *Bacillus subtilis* were amplified by PCR using the oligonucleotides of SEQ ID NOS: 48 and 49, and 50 and 51, respectively. These oligonucleotides contained BglII, SadI, XbaI and BamHI restriction enzyme sites, which are required and convenient for further cloning, in the 5' end regions, respectively. The obtained sacB fragment of 1.5 kb was cloned into the previously obtained pMW119-P$_{lac}$lacI vector at the XbaI-BamHI site. This vector was constructed in the same manner as that described for the pMW118-P$_{lac}$lacI vector (Skorokhodova, A. Y. et al, 2004, Biotekhnologiya (Rus), 5:3-21). However, this vector contained a polylinker moiety derived from pMW219 instead of the pMW218 plasmid.

Then, the aforementioned cat fragment of 1.0 kb was treated with BglII and SadI, and cloned into the RSF-P$_{lac}$lacIsacB plasmid obtained in the previous step at the BamHI-SacI site. The obtained plasmid pMW-P$_{lac}$lacIsacBcat contained the PlacUV5-lacI-sacB-cat fragment. In order to subclone this fragment into the RSF1010 vector, pMW-P$_{lac}$lacIsacBcat was digested with BglII, blunt-ended with DNA polymerase I Klenow fragment, and successively digested with SacI. A 3.8 kb BglII-SacI fragment of the pMWP$_{lac}$lacIsacBcat plasmid was eluted from a 1% agarose gel, and ligated with the RSF1010 vector which had been previously treated with PstI and SadI. *Escherichia coli* TG1 was transformed with the ligation mixture, and plated on the LB medium containing chloramphenicol (50 mg/L). The plasmids isolated from the grown clones were analyzed with restriction enzymes to obtain an RSFsacB plasmid. In order to construct an RSFsacBP$_{lac}$MCS vector, a DNA fragment containing the P$_{lacUV5}$ promoter was amplified by PCR using the oligonucleotides of SEQ ID NOS: 52 and 53 as primers and the pMW119-P$_{lac}$lacI plasmid as the template. The obtained fragment of 146 by was digested with SadI and NodI, and ligated with the SadI-NodI large fragment of the RSFsacB plasmid. Then, by PCR using the oligonucleotides of SEQ ID NOS: 54 and 55 as primers, and the pKD46 plasmid (Datsenko, K. A., Wanner, B. L., 2000, Proc. Natl. Acad. Sci. USA, 97, 6640-6645) as the template, a DNA fragment of 2.3 kb containing the λRedαβγ genes and the transcription terminator tL3 was amplified. The obtained fragment was cloned into the RSFsacBP$_{lac}$MCS vector at the PvuI-NotI site. In this way, the RSFRed plasmid was designed.

In order to eliminate read-through transcription of the Red genes, a ρ-dependent transcription terminator of the rrnB operon of *Escherichia coli* was inserted at a position between the cat gene and the P$_{lacUV5}$ promoter. For this purpose, a DNA fragment containing the P$_{lacUV5}$ promoter and the TrrnB terminator was amplified by PCR using the oligonucleotides of SEQ ID NOS: 56 and 53 as primers and the chromosome of *Escherichia coli* BW3350 as the template. These obtained fragments were treated with KpnI and ligated. Then, the 0.5 kb fragment containing both P$_{lacUV5}$ and TrrnB was amplified by PCR using the oligonucleotides of SEQ ID NOS: 53 and 57 as primers. The obtained DNA fragment was digested with EcoRI, blunt-ended by a treatment with DNA polymerase I Klenow fragment, digested with BamHI, and ligated with the Ecl136II-BamHI large fragment of the RSF-sacBPlacMCS vector. The obtained plasmid was designated RSF-Red-TER.

Reference Example 3

Construction of pMW118-attL-Tc-attR Plasmid

The pMW118-attL-Tc-attR plasmid was obtained by ligation of the following four fragments.

1) The BglII-EcoRI fragment (114 bp) including attL (SEQ ID NO: 60) which was obtained by PCR amplification of the region corresponding to attL of the *Escherichia coli* W3350 (containing λ prophage) chromosome using the primers P1 and P2 (SEQ ID NOS: 58 and 59) (these primers contained the subsidiary recognition sites for BglII and EcoRI).

2) The PstI-HindIII fragment (182 bp) including attR (SEQ ID NO: 63) which was obtained by PCR amplification of the region corresponding to attR of the *Escherichia coli* W3350 (containing λ prophage) chromosome using the primers P3 and P4 (SEQ ID NOS: 61 and 62) (these primers contained the subsidiary recognition sites for PstI and HindIII).

3) The BglII-HindIII large fragment (3916 bp) of pMW118-ter_rrnB. The plasmid pMW118-ter_rrnB was obtained by ligation of the following three DNA fragments:

The large DNA fragment (2359 bp) including the AatII-EcoRI fragment of pMW118 that was obtained by digesting pMW118 with EcoRI, treated with DNA polymerase I Klenow fragment, and then digesting with AatII;

The small AatII-BglII fragment (1194 bp) of pUC19 including the bla gene for ampicillin resistance (Ap$^R$), which was obtained by PCR amplification of the corresponding region of the pUC19 plasmid using the primers P5 and P6 (SEQ ID NOS: 64 and 65) (these primers contained the subsidiary recognition sites for PstI, AatII and BglII);

The small BglII-PstI fragment (363 bp) of the transcription terminator ter_rrnB, which was obtained by PCR amplification of the corresponding region of the *Escherichia coli* MG1655 chromosome using the primers P7 and P8 (SEQ ID NOS: 66 and 67) (these primers contained the subsidiary recognition sites for PstI, BglII and PstI).

4) The small EcoRI-PstI fragment (1388 bp) (SEQ ID NO: 68) of pML-Tc-ter_thrL including the tetracycline resistance gene and the ter_thrL transcription terminator; the pML-Tc-ter_thrL plasmid was obtained by the following two steps:

the pML-ter_thrL plasmid was obtained by digesting the pML-MCS plasmid (Mashko, S. V. et al., 2001, Biotekhnologiya (in Russian), no. 5, 3-20) with XbaI and BamHI, followed by ligation of the large fragment (3342 bp) with the XbaI-BamHI fragment (68 bp) carrying ter_thrL terminator obtained by PCR amplification of the corresponding region of the *Escherichia coli* MG1655 chromosome using the primers P9 and P10 (SEQ ID NOS: 69 and 70) (these primers contained the subsidiary recognition sites for PstI, XbaI and BamHI);

the pML-Tc-ter_thrL plasmid was obtained by digesting the pML-ter_thrL plasmid with KpnI and XbaI followed by treatment with Klenow fragment of DNA polymerase I and ligation with the small EcoRI-Van91I fragment (1317 bp) of pBR322 including the tetracycline resistance gene (pBR322 was digested with EcoRI and Van91I and then treated with DNA polymerase I Klenow fragment).

Explanation of Sequence Listing

SEQ ID NO: 1: Primer for deletion of ldhA
SEQ ID NO: 2: Primer for deletion of ldhA
SEQ ID NO: 3: Primer for confirming deletion of ldhA
SEQ ID NO: 4: Primer for confirming deletion of ldhA
SEQ ID NO: 5: Primer for deletion of lldD
SEQ ID NO: 6: Primer for deletion of lldD
SEQ ID NO: 7: Primer for confirming deletion of lldD
SEQ ID NO: 8: Primer for confirming deletion of lldD
SEQ ID NO: 9: Primer for amplification of yidE
SEQ ID NO: 10: Primer for amplification of yidE
SEQ ID NO: 11: Threonine promoter sequence
SEQ ID NO: 12: Primer for amplification of yidE
SEQ ID NO: 13: Nucleotide sequence of yidE of *Escherichia coli*
SEQ ID NO: 14: Amino acid sequence of YidE of *Escherichia coli*
SEQ ID NO: 15: Nucleotide sequence of yidE of *Salmonella typhimurium*
SEQ ID NO: 16: Amino acid sequence of YidE of *Salmonella typhimurium*
SEQ ID NO: 17: Nucleotide sequence of PC gene coding for pyruvate arboxylase of *Brevibacterium flavum*
SEQ ID NO: 18: Amino acid sequence of pyruvate carboxylase of *Brevibacterium flavum*
SEQ ID NO: 19: Primer for amplification of yidE
SEQ ID NO: 20: Nucleotide sequence of ldhA of *Escherichia coli*
SEQ ID NO: 21: Amino acid sequence of LdhA of *Escherichia coli*
SEQ ID NO: 22: Nucleotide sequence of lldD of *Escherichia coli*
SEQ ID NO: 23: Amino acid sequence of LldD of *Escherichia coli*
SEQ ID NO: 24: Consensus sequence of YidE of *Escherichia* and *Salmonella*
SEQ ID NO: 25: Nucleotide sequence of yidE of *Shigella flexneri*
SEQ ID NO: 26: Amino acid sequence of YidE of *Shigella flexneri*
SEQ ID NO: 27: Nucleotide sequence of yidE of *Yersinia pestis*
SEQ ID NO: 28: Amino acid sequence of YidE of *Yersinia pestis*
SEQ ID NO: 29: Consensus sequence of YidE of *Escherichia, Salmonella, Shigella,* and *Yersinia*
SEQ ID NO: 30: Nucleotide sequence of yidE of *Mannheimia succiniciproducens*
SEQ ID NO: 31: Amino acid sequence of YidE of *Mannheimia succiniciproducens*
SEQ ID NO: 32: Nucleotide sequence of primer for deletion of adhE
SEQ ID NO: 33: Nucleotide sequence of primer for deletion of adhE SEQ ID NO: 34: Nucleotide sequence of adhE of *Enterobacter aerogenes* AJ110637 (partial sequence)
SEQ ID NO: 35: Primer for amplification of threonine promoter
SEQ ID NO: 36: Primer for amplification of threonine promoter
SEQ ID NO: 37: Threonine promoter gene fragment
SEQ ID NO: 38: Primer for amplification of pyruvate carboxylase
SEQ ID NO: 39: Primer for amplification of pyruvate carboxylase
SEQ ID NO: 40: Pyruvate carboxylase gene fragment
SEQ ID NO: 41: Primer for amplification of threonine promoter
SEQ ID NO: 42: Primer for amplification of threonine promoter
SEQ ID NO: 43: Threonine promoter gene fragment
SEQ ID NO: 44: Nucleotide sequence of primer for amplification of yidE of *Enterobacter aerogenes* AJ110637
SEQ ID NO: 45: Nucleotide sequence of primer for amplification of yidE of *Enterobacter aerogenes* AJ110637
SEQ ID NO: 46: Nucleotide sequence of yidE of *Enterobacter aerogenes* AJ110637
SEQ ID NO: 47: Amino acid sequence of YidE of *Enterobacter aerogenes* AJ110637
SEQ ID NO: 48: Primer for amplification of cat gene
SEQ ID NO: 49: Primer for amplification of cat gene
SEQ ID NO: 50: Primer for amplification of sacB gene
SEQ ID NO: 51: Primer for amplification of sacB gene
SEQ ID NO: 52: Primer for amplification of DNA fragment containing $P_{lacUV5}$ promoter
SEQ ID NO: 53: Primer for amplification of DNA fragment containing $P_{lacUV5}$ promoter
SEQ ID NO: 54: Primer for amplification of DNA fragment containing λRedαβγ gene and tL3
SEQ ID NO: 55: Primer for amplification of DNA fragment containing λRedαβγ gene and tL3
SEQ ID NO: 56: Primer for amplification of DNA fragment containing $P_{lacUV5}$ promoter and TrrnB
SEQ ID NO: 57: Primer for amplification of DNA fragment containing $P_{lacUV5}$ promoter and TrrnB
SEQ ID NO: 58: Primer for amplification of attL
SEQ ID NO: 59: Primer for amplification of attL
SEQ ID NO: 60: Nucleotide sequence of attL
SEQ ID NO: 61: Primer for amplification of attR
SEQ ID NO: 62: Primer for amplification of attR
SEQ ID NO: 63: Nucleotide sequence of attR
SEQ ID NO: 64: Primer for amplification of DNA fragment containing bla gene
SEQ ID NO: 65: Primer for amplification of DNA fragment containing bla gene
SEQ ID NO: 66: Primer for amplification of DNA fragment containing ter_rrnB
SEQ ID NO: 67: Primer for amplification of DNA fragment containing ter_rrnB
SEQ ID NO: 68: Nucleotide sequence of the DNA fragment containing ter_thrL terminator
SEQ ID NO: 69: Primer for amplification of DNA fragment containing ter_thrL terminator
SEQ ID NO: 70: Primer for amplification of DNA fragment containing ter_thrL terminator
SEQ ID NO: 71: Consensus sequence of YidE of *Escherichia, Salmonella*, and *Enterobacter*
SEQ ID NO: 72: Consensus sequence of YidE of *Escherichia, Salmonella, Shigella, Yersinia*, and *Enterobacter*

INDUSTRIAL APPLICABILITY

According to the production method of the present invention, an organic acid can be quickly and highly efficiently produced. When the organic acid is succinic acid, the obtained succinic acid can be used for food additives, pharmaceuticals, cosmetics, and the like. Moreover, succinic acid-containing polymers can also be produced by performing a polymerization reaction using the obtained succinic acid as a raw material.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

---

The invention claimed is:

1. A method for producing succinic acid comprising:
   A) allowing a substance to act on an organic raw material in a reaction mixture containing carbonate ions, bicarbonate ions, or carbon dioxide gas, wherein the substance is selected from the group consisting of:
      i) a bacterium which has an ability to produce an organic acid and has been modified to have enhanced expression of the yidE gene,
      ii) a product obtained by processing the bacterium of i),
      iii) combinations thereof, and
   B) collecting the succinic acid:
   wherein the yidE gene is selected from the group consisting of:
      (a) a DNA comprising the nucleotide sequence of SEQ ID NO: 46, and
      (b) a DNA which hybridizes with a DNA comprising a nucleotide sequence complementary to the entire nucleotide sequence of SEQ ID NO: 46 under stringent conditions comprising washing with 1×SSC, 0.1% SDS at 60° C., and said DNA improves the ability of the bacterium to produce an organic acid when expression of the DNA is enhanced in the bacterium;
   wherein the enhanced expression is obtained by a method selected from the group consisting of:
      i) increasing the copy number of the yidE gene,
      ii) replacing a promoter sequence of the yidE gene with a stronger promoter, and
      iii) combinations thereof.

2. The method according to claim 1, wherein the bacterium belongs to the family Enterobacteriaceae.

3. The method according to claim 2, wherein the bacterium belongs to a genus selected from the group consisting *Escherichia, Enterobacter, Raoultella, Klebsiella*, and *Pantoea*.

4. The method according to claim 1, wherein the bacterium is a rumen bacterium.

5. The method according to claim 4, wherein the bacterium is *Mannheimia succiniciproducens*.

6. The method according to claim 1, wherein the bacterium has been further modified to decrease an enzymatic activity selected from the group consisting of lactate dehydrogenase activity, alcohol dehydrogenase activity, pyruvate formate lyase activity, and combinations thereof.

7. The method according to claim 1, wherein the bacterium has been further modified to have enhanced expression of a gene encoding a protein with pyruvate carboxylase activity.

8. A method for producing a succinic acid-containing polymer comprising:
   A) producing succinic acid by the method according to claim 1, and
   B) polymerizing the succinic acid.

9. The method according to claim 1, wherein the yidE gene codes for a protein selected from the group consisting of:
   A) a protein comprising the amino acid sequence of SEQ ID NO: 47, and
   B) a protein comprising an amino acid sequence having a homology of not less than 95% to the entire amino acid sequence of SEQ ID NO: 47, and said protein has an activity of enhancing the yield of the succinic acid.

* * * * *

UNITED STATES PATENT AND TRADEMARK OFFICE
CERTIFICATE OF CORRECTION

PATENT NO. : 8,076,111 B2
APPLICATION NO. : 12/579594
DATED : December 13, 2011
INVENTOR(S) : Fukui et al.

Page 1 of 2

It is certified that error appears in the above-identified patent and that said Letters Patent is hereby corrected as shown below:

IN THE CLAIMS:
Column 153, Line 12, Claim 1, should read:
1. A method for producing succinic acid comprising:
  A) allowing a substance to act on an organic raw material in a reaction mixture containing carbonate ions, bicarbonate ions, or carbon dioxide gas, wherein the substance is selected from the group consisting of:
    i) a bacterium which has an ability to produce an organic acid and has been modified to have enhanced expression of the *yidE* gene,
    ii) a product obtained by processing the bacterium of i),
    iii) combinations thereof, and
  B) collecting the succinic acid;
wherein the *yidE* gene is selected from the group consisting of:
  (a) a DNA comprising the nucleotide sequence of SEQ ID NO: 46, and
  (b) a DNA which hybridizes with a DNA comprising a nucleotide sequence complementary to the entire nucleotide sequence of SEQ ID NO: 46 under stringent conditions comprising washing with 1 × SSC, 0.1% SDS at 60°C, and said DNA improves the ability of the bacterium to produce an organic acid when expression of the DNA is enhanced in the bacterium;
wherein the enhanced expression is obtained by a method selected from the group consisting of:
  i) increasing the copy number of the *yidE* gene,
  ii) replacing a promoter sequence of the *yidE* gene with a stronger promoter, and
  iii) combinations thereof.

Column 153, Line 40, Claim 2, should read:
2. The method according to claim 1, wherein the bacterium belongs to the family *Enterobacteriaceae*.

Column 154, Line 32, Claim 9, should read:
9. The method according to claim 1, wherein the *yidE* gene codes for a protein selected from the group consisting of:

Signed and Sealed this
Third Day of April, 2012

David J. Kappos
*Director of the United States Patent and Trademark Office*

A) a protein comprising the amino acid sequence of SEQ ID NO: 47, and

B) a protein comprising an amino acid sequence having a homology of not less than 95% to the entire amino acid sequence of SEQ ID NO: 47, and said protein has an activity of enhancing the yield of the succinic acid.

SEQUENCE LISTING

```
<160> NUMBER OF SEQ ID NOS: 72

<210> SEQ ID NO 1
<211> LENGTH: 55
<212> TYPE: DNA
<213> ORGANISM: Artificial Sequence
<220> FEATURE:
<223> OTHER INFORMATION: primer for deleting ldhA

<400> SEQUENCE: 1
gtgattcaac atcactggag aaagtcttat gaaactctga agcctgcttt tttat          55

<210> SEQ ID NO 2
<211> LENGTH: 55
<212> TYPE: DNA
<213> ORGANISM: Artificial Sequence
<220> FEATURE:
<223> OTHER INFORMATION: primer for deleting ldhA

<400> SEQUENCE: 2
cctggaatgc aggggagcgg caagattaaa ccagttccgc tcaagttagt ataaa          55
```

<210> SEQ ID NO 3
<211> LENGTH: 22
<212> TYPE: DNA
<213> ORGANISM: Artificial Sequence
<220> FEATURE:
<223> OTHER INFORMATION: primer for confirming deletion of ldhA

<400> SEQUENCE: 3
gcgcctacac taagcatagt tg                                             22

<210> SEQ ID NO 4
<211> LENGTH: 22
<212> TYPE: DNA
<213> ORGANISM: Artificial Sequence
<220> FEATURE:
<223> OTHER INFORMATION: primer for confirming deletion of ldhA

<400> SEQUENCE: 4
ccatcagcag gcttagcgca ac                                             22

<210> SEQ ID NO 5
<211> LENGTH: 55
<212> TYPE: DNA
<213> ORGANISM: Artificial Sequence
<220> FEATURE:
<223> OTHER INFORMATION: primer for deleting lldD

<400> SEQUENCE: 5
gagggagaaa aacgcatgat tatttccgca gccagcgtga agcctgcttt tttat         55

<210> SEQ ID NO 6
<211> LENGTH: 54
<212> TYPE: DNA
<213> ORGANISM: Artificial Sequence
<220> FEATURE:
<223> OTHER INFORMATION: primer for deleting lldD

<400> SEQUENCE: 6
gcgcaaacga ctatgccgca ttcccttteg ccatggcgct caagttagta taaa          54

<210> SEQ ID NO 7
<211> LENGTH: 23
<212> TYPE: DNA
<213> ORGANISM: Artificial Sequence
<220> FEATURE:
<223> OTHER INFORMATION: primer for confirming deletion of lldD

<400> SEQUENCE: 7
gcgtaaagca atgatggcgc acc                                            23

<210> SEQ ID NO 8
<211> LENGTH: 23
<212> TYPE: DNA
<213> ORGANISM: Artificial Sequence
<220> FEATURE:
<223> OTHER INFORMATION: primer for confirming deletion of lldD

<400> SEQUENCE: 8
gcggtgtcgt ttcagagtga ggg                                            23

<210> SEQ ID NO 9
<211> LENGTH: 20
<212> TYPE: DNA
<213> ORGANISM: Artificial Sequence
<220> FEATURE:
<223> OTHER INFORMATION: primer for amplifying yidE

```
<400> SEQUENCE: 9
gaaaatatgg aagtctctgg                                                20

<210> SEQ ID NO 10
<211> LENGTH: 19
<212> TYPE: DNA
<213> ORGANISM: Artificial Sequence
<220> FEATURE:
<223> OTHER INFORMATION: primer for amplifying yidE

<400> SEQUENCE: 10
ctatatgccg gtaaaactg                                                 19

<210> SEQ ID NO 11
<211> LENGTH: 348
<212> TYPE: DNA
<213> ORGANISM: Escherichia coli

<400> SEQUENCE: 11
aagctttacg cgaacgagcc atgacattgc tgacgactct ggcagtggca gatgacataa    60
aactggtcga ctggttacaa caacgcctgg ggcttttaga gcaacgagac acggcaatgt   120
tgcaccgttt gctgcatgat attgaaaaaa atatcaccaa ataaaaaacg ccttagtaag   180 tattttcag cttttcattc tgactgcaac gggcaatatg tctctgtgtg gattaaaaaa   240
agagtgtctg atagcagctt ctgaactggt tacctgccgt gagtaaatta aaattttatt   300
gacttaggtc actaaaatact ttaaccaata taggcgactc taggatcc               348

<210> SEQ ID NO 12
<211> LENGTH: 22
<212> TYPE: DNA
<213> ORGANISM: Artificial Sequence
<220> FEATURE:
<223> OTHER INFORMATION: primer for amplifying yidE

<400> SEQUENCE: 12
cgggatccgc cataatccgt ag                                             22

<210> SEQ ID NO 13
<211> LENGTH: 1662
<212> TYPE: DNA
<213> ORGANISM: Escherichia coli
<220> FEATURE:
<221> NAME/KEY: CDS
<222> LOCATION: (1)..(1659)

<400> SEQUENCE: 13 atg agt gat ata gca tta acg gtc agt att ctg gct ttg gtg gca gtc    48
Met Ser Asp Ile Ala Leu Thr Val Ser Ile Leu Ala Leu Val Ala Val
1               5                   10                  15 gtc ggt ttg ttt atc ggc aac gtc aaa ttt cgc ggc ata gga tta ggt    96
Val Gly Leu Phe Ile Gly Asn Val Lys Phe Arg Gly Ile Gly Leu Gly
                20                  25                  30 att ggc ggc gtg ctg ttt ggt ggg atc atc gtc ggc cat ttt gtt tct   144
Ile Gly Gly Val Leu Phe Gly Gly Ile Ile Val Gly His Phe Val Ser
            35                  40                  45 cag gcg ggg atg aca tta agt agc gat atg ctg cat gtt att cag gaa   192
Gln Ala Gly Met Thr Leu Ser Ser Asp Met Leu His Val Ile Gln Glu
        50                  55                  60 ttt ggc ctg atc ctg ttc gtt tat act atc ggg att cag gta ggg ccg   240
Phe Gly Leu Ile Leu Phe Val Tyr Thr Ile Gly Ile Gln Val Gly Pro
65                  70                  75                  80
```

```
ggc ttc ttt gcc tca ttg cgc gtc tcc gga tta cgc ctc aac ctg ttt       288
Gly Phe Phe Ala Ser Leu Arg Val Ser Gly Leu Arg Leu Asn Leu Phe
             85                  90                  95 gct gtt ctg atc gtc atc atc ggt ggt ctg gtt acc gcc atc ctg cat       336
Ala Val Leu Ile Val Ile Ile Gly Gly Leu Val Thr Ala Ile Leu His
            100                 105                 110 aaa ctg ttt gat att cca ctg ccg gta gtg ctg ggg att ttc tcc ggt       384
Lys Leu Phe Asp Ile Pro Leu Pro Val Val Leu Gly Ile Phe Ser Gly
            115                 120                 125 gcg gtt acc aat acg cca gcg ctg ggg gca ggg cag cag att ttg cgc       432
Ala Val Thr Asn Thr Pro Ala Leu Gly Ala Gly Gln Gln Ile Leu Arg
130                 135                 140 gac ctg ggt aca cca atg gaa atg gtc gat cag atg ggg atg agt tac       480
Asp Leu Gly Thr Pro Met Glu Met Val Asp Gln Met Gly Met Ser Tyr
145                 150                 155                 160 gcg atg gcg tat cca ttc ggc att tgc ggg att ttg ttc acc atg tgg       528
Ala Met Ala Tyr Pro Phe Gly Ile Cys Gly Ile Leu Phe Thr Met Trp
                165                 170                 175 atg ttg cgg gtt att ttc cgc gtc aat gtc gag aca gaa gct cag cag       576
Met Leu Arg Val Ile Phe Arg Val Asn Val Glu Thr Glu Ala Gln Gln
            180                 185                 190 cac gag tct tca cgc acc aat ggc ggc gcg ctg atc aag act atc aat       624
His Glu Ser Ser Arg Thr Asn Gly Gly Ala Leu Ile Lys Thr Ile Asn
            195                 200                 205 att cgc gtt gag aac cct aac ctg cat gat tta gcc att aaa gat gta       672
Ile Arg Val Glu Asn Pro Asn Leu His Asp Leu Ala Ile Lys Asp Val
210                 215                 220 ccg att ctc aac ggc gac aaa att atc tgc tcg cgt ctg aaa cgc gaa       720
Pro Ile Leu Asn Gly Asp Lys Ile Ile Cys Ser Arg Leu Lys Arg Glu
225                 230                 235                 240 gaa acc cta aaa gtt cct tcg cca gat acc att atc caa ctg ggc gat       768
Glu Thr Leu Lys Val Pro Ser Pro Asp Thr Ile Ile Gln Leu Gly Asp
                245                 250                 255 ttg ctg cat ctg gtg ggt cag cca gcg gat tta cat aat gcg caa ctg       816
Leu Leu His Leu Val Gly Gln Pro Ala Asp Leu His Asn Ala Gln Leu
            260                 265                 270 gtg att ggt cag gag gtc gat act tcg ctg tcc acg aaa ggc act gat       864
Val Ile Gly Gln Glu Val Asp Thr Ser Leu Ser Thr Lys Gly Thr Asp
            275                 280                 285 ttg cgc gtc gag cgt gtg gtg gtc acc aat gaa aac gtg ctc gga aaa       912
Leu Arg Val Glu Arg Val Val Val Thr Asn Glu Asn Val Leu Gly Lys
            290                 295                 300 cgt att cgc gac ctg cac ttt aaa gaa cgc tat gac gtt gtt atc tcg       960
Arg Ile Arg Asp Leu His Phe Lys Glu Arg Tyr Asp Val Val Ile Ser
305                 310                 315                 320 cgc ctg aac cgt gcc ggg gtc gaa ctg gtc gcc agt ggc gat atc agc      1008
Arg Leu Asn Arg Ala Gly Val Glu Leu Val Ala Ser Gly Asp Ile Ser
                325                 330                 335 ctg cag ttc ggc gat atc ctc aat ctg gtg ggg cgt ccg tcc gca att      1056
Leu Gln Phe Gly Asp Ile Leu Asn Leu Val Gly Arg Pro Ser Ala Ile
            340                 345                 350 gat gcc gtt gcc aat gtg ctg ggg aat gcg cag caa aaa ctg caa cag      1104
Asp Ala Val Ala Asn Val Leu Gly Asn Ala Gln Gln Lys Leu Gln Gln
            355                 360                 365 gtt cag atg ctg cca gtg ttt att ggc atc ggg cta ggc gta ttg tta      1152
Val Gln Met Leu Pro Val Phe Ile Gly Ile Gly Leu Gly Val Leu Leu
            370                 375                 380 ggt tct att ccc gtc ttt gtg cca gga ttc ccg gcc gcg ttg aaa ctg      1200
Gly Ser Ile Pro Val Phe Val Pro Gly Phe Pro Ala Ala Leu Lys Leu
385                 390                 395                 400
```

```
ggg ctg gcg ggc gga ccg ctg att atg gcg ttg atc ctc ggg cgt atc      1248
Gly Leu Ala Gly Gly Pro Leu Ile Met Ala Leu Ile Leu Gly Arg Ile
            405                 410                 415 ggc agt atc ggc aag ctg tac tgg ttt atg ccg cca agc gcc aac ctc      1296
Gly Ser Ile Gly Lys Leu Tyr Trp Phe Met Pro Pro Ser Ala Asn Leu
        420                 425                 430 gcg ctg cgg gag ctg ggg atc gtg ctg ttc ctc tcg gtc gtt ggt ctg      1344
Ala Leu Arg Glu Leu Gly Ile Val Leu Phe Leu Ser Val Val Gly Leu
    435                 440                 445 aaa tct ggt ggg gat ttt gtg aat acc ctg gtc aat ggc gaa ggg cta      1392
Lys Ser Gly Gly Asp Phe Val Asn Thr Leu Val Asn Gly Glu Gly Leu
450                 455                 460 agc tgg att ggt tat ggt gcc ctg atc acc gcc gtt ccg ctg att act      1440
Ser Trp Ile Gly Tyr Gly Ala Leu Ile Thr Ala Val Pro Leu Ile Thr
465                 470                 475                 480 gtt ggc att ctg gcg cgg atg tta gcc aaa atg aat tac ctg acc atg      1488
Val Gly Ile Leu Ala Arg Met Leu Ala Lys Met Asn Tyr Leu Thr Met
                485                 490                 495 tgc ggg atg ctg gca ggt tcc atg acc gat cct ccg gcg ctg gcg ttt      1536
Cys Gly Met Leu Ala Gly Ser Met Thr Asp Pro Pro Ala Leu Ala Phe
            500                 505                 510 gct aat aat ctt cat cca acc agc ggt gcg gcg gcg ctc tct tac gcc      1584
Ala Asn Asn Leu His Pro Thr Ser Gly Ala Ala Ala Leu Ser Tyr Ala
        515                 520                 525 act gtc tat ccg ttg gta atg ttc ctg cgc att atc acc ccc caa tta      1632
Thr Val Tyr Pro Leu Val Met Phe Leu Arg Ile Ile Thr Pro Gln Leu
    530                 535                 540 ctg gcg gtg ctc ttc tgg agt atc ggt taa                              1662
Leu Ala Val Leu Phe Trp Ser Ile Gly
545                 550

<210> SEQ ID NO 14
<211> LENGTH: 553
<212> TYPE: PRT
<213> ORGANISM: Escherichia coli

<400> SEQUENCE: 14

Met Ser Asp Ile Ala Leu Thr Val Ser Ile Leu Ala Leu Val Ala Val
1               5                   10                  15

Val Gly Leu Phe Ile Gly Asn Val Lys Phe Arg Gly Ile Gly Leu Gly
            20                  25                  30

Ile Gly Gly Val Leu Phe Gly Gly Ile Ile Val Gly His Phe Val Ser
        35                  40                  45

Gln Ala Gly Met Thr Leu Ser Ser Asp Met Leu His Val Ile Gln Glu
    50                  55                  60

Phe Gly Leu Ile Leu Phe Val Tyr Thr Ile Gly Ile Gln Val Gly Pro
65                  70                  75                  80

Gly Phe Phe Ala Ser Leu Arg Val Ser Gly Leu Arg Leu Asn Leu Phe
                85                  90                  95

Ala Val Leu Ile Val Ile Ile Gly Gly Leu Val Thr Ala Ile Leu His
            100                 105                 110

Lys Leu Phe Asp Ile Pro Leu Pro Val Val Leu Gly Ile Phe Ser Gly
        115                 120                 125

Ala Val Thr Asn Thr Pro Ala Leu Gly Ala Gly Gln Gln Ile Leu Arg
    130                 135                 140

Asp Leu Gly Thr Pro Met Glu Met Val Asp Gln Met Gly Met Ser Tyr
145                 150                 155                 160

Ala Met Ala Tyr Pro Phe Gly Ile Cys Gly Ile Leu Phe Thr Met Trp
                165                 170                 175
```

```
Met Leu Arg Val Ile Phe Arg Val Asn Val Glu Thr Glu Ala Gln Gln
            180                 185                 190

His Glu Ser Ser Arg Thr Asn Gly Gly Ala Leu Ile Lys Thr Ile Asn
            195                 200                 205

Ile Arg Val Glu Asn Pro Asn Leu His Asp Leu Ala Ile Lys Asp Val
210                 215                 220

Pro Ile Leu Asn Gly Asp Lys Ile Ile Cys Ser Arg Leu Lys Arg Glu
225                 230                 235                 240

Glu Thr Leu Lys Val Pro Ser Pro Asp Thr Ile Ile Gln Leu Gly Asp
                245                 250                 255

Leu Leu His Leu Val Gly Gln Pro Ala Asp Leu His Asn Ala Gln Leu
                260                 265                 270

Val Ile Gly Gln Glu Val Asp Thr Ser Leu Ser Thr Lys Gly Thr Asp
                275                 280                 285

Leu Arg Val Glu Arg Val Val Thr Asn Glu Asn Val Leu Gly Lys
            290                 295                 300

Arg Ile Arg Asp Leu His Phe Lys Glu Arg Tyr Asp Val Val Ile Ser
305                 310                 315                 320

Arg Leu Asn Arg Ala Gly Val Glu Leu Val Ala Ser Gly Asp Ile Ser
                325                 330                 335

Leu Gln Phe Gly Asp Ile Leu Asn Leu Val Gly Arg Pro Ser Ala Ile
                340                 345                 350

Asp Ala Val Ala Asn Val Leu Gly Asn Ala Gln Gln Lys Leu Gln Gln
                355                 360                 365

Val Gln Met Leu Pro Val Phe Ile Gly Ile Gly Leu Gly Val Leu Leu
                370                 375                 380

Gly Ser Ile Pro Val Phe Val Pro Gly Phe Pro Ala Ala Leu Lys Leu
385                 390                 395                 400

Gly Leu Ala Gly Gly Pro Leu Ile Met Ala Leu Ile Leu Gly Arg Ile
                405                 410                 415

Gly Ser Ile Gly Lys Leu Tyr Trp Phe Met Pro Pro Ser Ala Asn Leu
                420                 425                 430

Ala Leu Arg Glu Leu Gly Ile Val Leu Phe Leu Ser Val Val Gly Leu
                435                 440                 445

Lys Ser Gly Gly Asp Phe Val Asn Thr Leu Val Asn Gly Glu Gly Leu
450                 455                 460

Ser Trp Ile Gly Tyr Gly Ala Leu Ile Thr Ala Val Pro Leu Ile Thr
465                 470                 475                 480

Val Gly Ile Leu Ala Arg Met Leu Ala Lys Met Asn Tyr Leu Thr Met
                485                 490                 495

Cys Gly Met Leu Ala Gly Ser Met Thr Asp Pro Pro Ala Leu Ala Phe
                500                 505                 510

Ala Asn Asn Leu His Pro Thr Ser Gly Ala Ala Ala Leu Ser Tyr Ala
                515                 520                 525

Thr Val Tyr Pro Leu Val Met Phe Leu Arg Ile Ile Thr Pro Gln Leu
            530                 535                 540

Leu Ala Val Leu Phe Trp Ser Ile Gly
545                 550
```

<210> SEQ ID NO 15
<211> LENGTH: 1662
<212> TYPE: DNA
<213> ORGANISM: Salmonella typhimurium
<220> FEATURE:
<221> NAME/KEY: CDS

<222> LOCATION: (1)..(1662)

<400> SEQUENCE: 15

| | | | | | | | | | | | | | | | | |
|---|---|---|---|---|---|---|---|---|---|---|---|---|---|---|---|---|
| atg | agt | gat | atc | gca | ttg | acg | gtc | agc | gtt | ctg | gcg | ttg | gtg | gcg | gtt | 48 |
| Met | Ser | Asp | Ile | Ala | Leu | Thr | Val | Ser | Val | Leu | Ala | Leu | Val | Ala | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtc | ggt | tta | tgg | atc | ggc | aac | att | aaa | gtg | cgc | ggt | gtc | ggc | ttt | ggt | 96 |
| Val | Gly | Leu | Trp | Ile | Gly | Asn | Ile | Lys | Val | Arg | Gly | Val | Gly | Phe | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| att | ggc | ggc | gtt | ctg | ttc | ggc | ggt | att | atc | gtc | ggc | cac | ttc | gtc | gat | 144 |
| Ile | Gly | Gly | Val | Leu | Phe | Gly | Gly | Ile | Ile | Val | Gly | His | Phe | Val | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| cag | gct | ggg | gtg | acg | ctg | agt | ggc | gat | atg | ctg | cac | ttt | atc | cag | gaa | 192 |
| Gln | Ala | Gly | Val | Thr | Leu | Ser | Gly | Asp | Met | Leu | His | Phe | Ile | Gln | Glu | |
| | 50 | | | | | 55 | | | | | 60 | | | | | |

| | | | | | | | | | | | | | | | | |
|---|---|---|---|---|---|---|---|---|---|---|---|---|---|---|---|---|
| ttc | ggc | ctg | atc | ctt | ttt | gtt | tat | acc | atc | ggc | ata | cag | gtg | ggg | ccg | 240 |
| Phe | Gly | Leu | Ile | Leu | Phe | Val | Tyr | Thr | Ile | Gly | Ile | Gln | Val | Gly | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggg | ttt | ttc | gcc | tcg | ctg | cgc | gtt | tcc | ggg | ctg | cgt | ctc | aat | ctg | ttt | 288 |
| Gly | Phe | Phe | Ala | Ser | Leu | Arg | Val | Ser | Gly | Leu | Arg | Leu | Asn | Leu | Phe | |
| | | | | 85 | | | | | 90 | | | | | 95 | | |

| | | | | | | | | | | | | | | | | |
|---|---|---|---|---|---|---|---|---|---|---|---|---|---|---|---|---|
| gct | gtt | ctg | att | gtg | att | atg | ggc | ggg | ttg | gtc | acc | gcg | att | ctg | cat | 336 |
| Ala | Val | Leu | Ile | Val | Ile | Met | Gly | Gly | Leu | Val | Thr | Ala | Ile | Leu | His | |
| | | | | 100 | | | | | 105 | | | | | 110 | | |

| | | | | | | | | | | | | | | | | |
|---|---|---|---|---|---|---|---|---|---|---|---|---|---|---|---|---|
| aaa | att | ttc | gct | att | ccg | ctg | ccg | gtg | gtg | ctg | ggg | att | ttc | tcc | ggc | 384 |
| Lys | Ile | Phe | Ala | Ile | Pro | Leu | Pro | Val | Val | Leu | Gly | Ile | Phe | Ser | Gly | |
| | | 115 | | | | | 120 | | | | | 125 | | | | |

| | | | | | | | | | | | | | | | | |
|---|---|---|---|---|---|---|---|---|---|---|---|---|---|---|---|---|
| gca | gtc | acc | aat | acg | cct | gcg | tta | ggg | gcg | ggt | cag | caa | atc | ctg | cgc | 432 |
| Ala | Val | Thr | Asn | Thr | Pro | Ala | Leu | Gly | Ala | Gly | Gln | Gln | Ile | Leu | Arg | |
| | 130 | | | | | 135 | | | | | 140 | | | | | |

| | | | | | | | | | | | | | | | | |
|---|---|---|---|---|---|---|---|---|---|---|---|---|---|---|---|---|
| gat | ctg | gga | acg | cca | gtg | gat | ctg | gtg | gat | cag | atg | ggg | atg | agc | tat | 480 |
| Asp | Leu | Gly | Thr | Pro | Val | Asp | Leu | Val | Asp | Gln | Met | Gly | Met | Ser | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gcg | atg | gcg | tat | ccg | ttt | ggc | atc | tgc | ggt | att | ttg | ctc | acc | atg | tgg | 528 |
| Ala | Met | Ala | Tyr | Pro | Phe | Gly | Ile | Cys | Gly | Ile | Leu | Leu | Thr | Met | Trp | |
| | | | | 165 | | | | | 170 | | | | | 175 | | |

| | | | | | | | | | | | | | | | | |
|---|---|---|---|---|---|---|---|---|---|---|---|---|---|---|---|---|
| ctg | atg | cgg | ctg | att | ttt | cgc | gtt | aac | gtc | gag | gcg | gag | gcg | cag | aag | 576 |
| Leu | Met | Arg | Leu | Ile | Phe | Arg | Val | Asn | Val | Glu | Ala | Glu | Ala | Gln | Lys | |
| | | | | 180 | | | | | 185 | | | | | 190 | | |

| | | | | | | | | | | | | | | | | |
|---|---|---|---|---|---|---|---|---|---|---|---|---|---|---|---|---|
| cac | gaa | tcc | tct | ctc | gct | aac | ggc | cat | tca | tta | att | cag | aca | atg | aat | 624 |
| His | Glu | Ser | Ser | Leu | Ala | Asn | Gly | His | Ser | Leu | Ile | Gln | Thr | Met | Asn | |
| | | | 195 | | | | | 200 | | | | | 205 | | | |

| | | | | | | | | | | | | | | | | |
|---|---|---|---|---|---|---|---|---|---|---|---|---|---|---|---|---|
| atc | cgt | gtc | gag | aat | ccg | aac | ctc | aat | aat | atg | gct | atc | cag | gat | gtg | 672 |
| Ile | Arg | Val | Glu | Asn | Pro | Asn | Leu | Asn | Asn | Met | Ala | Ile | Gln | Asp | Val | |
| | 210 | | | | | 215 | | | | | 220 | | | | | |

| | | | | | | | | | | | | | | | | |
|---|---|---|---|---|---|---|---|---|---|---|---|---|---|---|---|---|
| ccg | atc | ctg | aac | agc | gat | aaa | atc | att | tgc | tca | cgc | ctg | aaa | cgc | gac | 720 |
| Pro | Ile | Leu | Asn | Ser | Asp | Lys | Ile | Ile | Cys | Ser | Arg | Leu | Lys | Arg | Asp | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gac | acg | ctg | atg | gtg | ccg | tcg | ccg | ggg | acg | att | atc | cag | gca | ggc | gac | 768 |
| Asp | Thr | Leu | Met | Val | Pro | Ser | Pro | Gly | Thr | Ile | Ile | Gln | Ala | Gly | Asp | |
| | | | | 245 | | | | | 250 | | | | | 255 | | |

| | | | | | | | | | | | | | | | | |
|---|---|---|---|---|---|---|---|---|---|---|---|---|---|---|---|---|
| ctg | ctg | cac | ctc | gtc | ggc | caa | tct | acc | gac | ctg | cat | aac | gcg | caa | ctg | 816 |
| Leu | Leu | His | Leu | Val | Gly | Gln | Ser | Thr | Asp | Leu | His | Asn | Ala | Gln | Leu | |
| | | | | 260 | | | | | 265 | | | | | 270 | | |

| | | | | | | | | | | | | | | | | |
|---|---|---|---|---|---|---|---|---|---|---|---|---|---|---|---|---|
| gtg | atc | ggc | aag | gaa | gtg | gac | acc | tcg | ttg | tcg | acg | cgt | ggc | acg | gat | 864 |
| Val | Ile | Gly | Lys | Glu | Val | Asp | Thr | Ser | Leu | Ser | Thr | Arg | Gly | Thr | Asp | |
| | | 275 | | | | | 280 | | | | | 285 | | | | |

| | | | | | | | | | | | | | | | | |
|---|---|---|---|---|---|---|---|---|---|---|---|---|---|---|---|---|
| tta | cgc | gtc | gag | cgt | gtg | gtc | gtc | acc | aac | gaa | aaa | gtg | ctc | ggc | aaa | 912 |
| Leu | Arg | Val | Glu | Arg | Val | Val | Val | Thr | Asn | Glu | Lys | Val | Leu | Gly | Lys | |
| | 290 | | | | | 295 | | | | | 300 | | | | | |

```
cgt atc cgc gat ttg cac ttt aaa gag cgt tat gac gtg gtt atc tcc      960
Arg Ile Arg Asp Leu His Phe Lys Glu Arg Tyr Asp Val Val Ile Ser
305                 310                 315                 320 cgc ctt aac cgc gcg ggc gtt gag ctg gtc gcc agt agt gac gct agc     1008
Arg Leu Asn Arg Ala Gly Val Glu Leu Val Ala Ser Ser Asp Ala Ser
                325                 330                 335 ctg cag ttt ggc gac att ctc aat ctg gtg ggg cgt cca gcc tcg att     1056
Leu Gln Phe Gly Asp Ile Leu Asn Leu Val Gly Arg Pro Ala Ser Ile
            340                 345                 350 gat gcg gta gcc aat gtg gtc ggc aac gcg cag caa aaa ctc cag cag     1104
Asp Ala Val Ala Asn Val Val Gly Asn Ala Gln Gln Lys Leu Gln Gln
        355                 360                 365 gtg cag atg ctg ccg gtg ttt atc ggc atc gga tta ggg gtt ctg ctt     1152
Val Gln Met Leu Pro Val Phe Ile Gly Ile Gly Leu Gly Val Leu Leu
    370                 375                 380 ggg tca atc ccg ttg ttt gtg ccg gga ttc ccg gtc gcg tta aaa ctg     1200
Gly Ser Ile Pro Leu Phe Val Pro Gly Phe Pro Val Ala Leu Lys Leu
385                 390                 395                 400 ggg ctg gcc ggc ggg ccg ctg atc atg gcg cta att ttg ggg cgt atc     1248
Gly Leu Ala Gly Gly Pro Leu Ile Met Ala Leu Ile Leu Gly Arg Ile
                405                 410                 415 ggc agc atc ggt aag ctg tac tgg ttt atg ccg ccg agc gcc aac ctc     1296
Gly Ser Ile Gly Lys Leu Tyr Trp Phe Met Pro Pro Ser Ala Asn Leu
            420                 425                 430 gcg ctg cgt gag tta ggc atc gtt ttg ttt ctg gcg gtc gtt ggg ctg     1344
Ala Leu Arg Glu Leu Gly Ile Val Leu Phe Leu Ala Val Val Gly Leu
        435                 440                 445 aaa tcc ggc ggc gat ttt gtc gat acg ctg acg cag ggc gaa gga tta     1392
Lys Ser Gly Gly Asp Phe Val Asp Thr Leu Thr Gln Gly Glu Gly Leu
    450                 455                 460 agc tgg att ggc tat ggt att ttc atc acc gct att ccg ctg att acc     1440
Ser Trp Ile Gly Tyr Gly Ile Phe Ile Thr Ala Ile Pro Leu Ile Thr
465                 470                 475                 480 gtc ggt ttg ctg gcg cgg att ttt gcc aaa atg aac tat ctg acg ctg     1488
Val Gly Leu Leu Ala Arg Ile Phe Ala Lys Met Asn Tyr Leu Thr Leu
                485                 490                 495 tgc ggg atg ctg gcc ggt tcg atg acc gat ccg cca gcg ctg gca ttt     1536
Cys Gly Met Leu Ala Gly Ser Met Thr Asp Pro Pro Ala Leu Ala Phe
            500                 505                 510 gcc aac aat ctt cat gcc acc agc ggc gcg gcg gcg ctc tct tac gcg     1584
Ala Asn Asn Leu His Ala Thr Ser Gly Ala Ala Ala Leu Ser Tyr Ala
        515                 520                 525 acc gtc tat ccg tta gtg atg ttc ctg cgt att atc acg cca caa ctg     1632
Thr Val Tyr Pro Leu Val Met Phe Leu Arg Ile Ile Thr Pro Gln Leu
    530                 535                 540 ctg gcg gtg att ttt tgg gga atg ggt tag                             1662
Leu Ala Val Ile Phe Trp Gly Met Gly
545                 550

<210> SEQ ID NO 16
<211> LENGTH: 553
<212> TYPE: PRT
<213> ORGANISM: Salmonella typhimurium

<400> SEQUENCE: 16

Met Ser Asp Ile Ala Leu Thr Val Ser Val Leu Ala Leu Val Ala Val
1               5                   10                  15

Val Gly Leu Trp Ile Gly Asn Ile Lys Val Arg Gly Val Gly Phe Gly
                20                  25                  30

Ile Gly Gly Val Leu Phe Gly Gly Ile Ile Val Gly His Phe Val Asp
            35                  40                  45
```

```
Gln Ala Gly Val Thr Leu Ser Gly Asp Met Leu His Phe Ile Gln Glu
    50                  55                  60
Phe Gly Leu Ile Leu Phe Val Tyr Thr Ile Gly Ile Gln Val Gly Pro
65                  70                  75                  80
Gly Phe Phe Ala Ser Leu Arg Val Ser Gly Leu Arg Leu Asn Leu Phe
                85                  90                  95
Ala Val Leu Ile Val Ile Met Gly Gly Leu Val Thr Ala Ile Leu His
            100                 105                 110
Lys Ile Phe Ala Ile Pro Leu Pro Val Val Leu Gly Ile Phe Ser Gly
        115                 120                 125
Ala Val Thr Asn Thr Pro Ala Leu Gly Ala Gly Gln Gln Ile Leu Arg
    130                 135                 140
Asp Leu Gly Thr Pro Val Asp Leu Val Asp Gln Met Gly Met Ser Tyr
145                 150                 155                 160
Ala Met Ala Tyr Pro Phe Gly Ile Cys Gly Ile Leu Leu Thr Met Trp
                165                 170                 175
Leu Met Arg Leu Ile Phe Arg Val Asn Val Glu Ala Glu Ala Gln Lys
            180                 185                 190
His Glu Ser Ser Leu Ala Asn Gly His Ser Leu Ile Gln Thr Met Asn
        195                 200                 205
Ile Arg Val Glu Asn Pro Asn Leu Asn Asn Met Ala Ile Gln Asp Val
    210                 215                 220
Pro Ile Leu Asn Ser Asp Lys Ile Ile Cys Ser Arg Leu Lys Arg Asp
225                 230                 235                 240
Asp Thr Leu Met Val Pro Ser Pro Gly Thr Ile Ile Gln Ala Gly Asp
                245                 250                 255
Leu Leu His Leu Val Gly Gln Ser Thr Asp Leu His Asn Ala Gln Leu
            260                 265                 270
Val Ile Gly Lys Glu Val Asp Thr Ser Leu Ser Thr Arg Gly Thr Asp
        275                 280                 285
Leu Arg Val Glu Arg Val Val Val Thr Asn Glu Lys Val Leu Gly Lys
    290                 295                 300
Arg Ile Arg Asp Leu His Phe Lys Glu Arg Tyr Asp Val Val Ile Ser
305                 310                 315                 320
Arg Leu Asn Arg Ala Gly Val Glu Leu Val Ala Ser Ser Asp Ala Ser
                325                 330                 335
Leu Gln Phe Gly Asp Ile Leu Asn Leu Val Gly Arg Pro Ala Ser Ile
            340                 345                 350
Asp Ala Val Ala Asn Val Val Gly Asn Ala Gln Gln Lys Leu Gln Gln
        355                 360                 365
Val Gln Met Leu Pro Val Phe Ile Gly Ile Gly Leu Gly Val Leu Leu
    370                 375                 380
Gly Ser Ile Pro Leu Phe Val Pro Gly Phe Pro Val Ala Leu Lys Leu
385                 390                 395                 400
Gly Leu Ala Gly Gly Pro Leu Ile Met Ala Leu Ile Leu Gly Arg Ile
                405                 410                 415
Gly Ser Ile Gly Lys Leu Tyr Trp Phe Met Pro Pro Ser Ala Asn Leu
            420                 425                 430
Ala Leu Arg Glu Leu Gly Ile Val Leu Phe Leu Ala Val Val Gly Leu
        435                 440                 445
Lys Ser Gly Gly Asp Phe Val Asp Thr Leu Thr Gln Gly Glu Gly Leu
    450                 455                 460
Ser Trp Ile Gly Tyr Gly Ile Phe Ile Thr Ala Ile Pro Leu Ile Thr
```

```
                 465                 470                 475                 480
Val Gly Leu Leu Ala Arg Ile Phe Ala Lys Met Asn Tyr Leu Thr Leu
                        485                 490                 495

Cys Gly Met Leu Ala Gly Ser Met Thr Asp Pro Pro Ala Leu Ala Phe
                500                 505                 510

Ala Asn Asn Leu His Ala Thr Ser Gly Ala Ala Leu Ser Tyr Ala
                515                 520                 525

Thr Val Tyr Pro Leu Val Met Phe Leu Arg Ile Ile Thr Pro Gln Leu
        530                 535                 540

Leu Ala Val Ile Phe Trp Gly Met Gly
545                 550

<210> SEQ ID NO 17
<211> LENGTH: 3420
<212> TYPE: DNA
<213> ORGANISM: Brevibacterium fluvum
<220> FEATURE:
<221> NAME/KEY: CDS
<222> LOCATION: (1)..(3420)

<400> SEQUENCE: 17 atg tcg act cac aca tct tca acg ctt cca gca ttc aaa aag atc ttg       48
Met Ser Thr His Thr Ser Ser Thr Leu Pro Ala Phe Lys Lys Ile Leu
1               5                   10                  15 gta gca aac cgc ggc gaa atc gcg gtc cgt gct ttc cgt gca gca ctc       96
Val Ala Asn Arg Gly Glu Ile Ala Val Arg Ala Phe Arg Ala Ala Leu
            20                  25                  30 gaa acc ggt gca gcc acg gta gct att tac ccc cgt gaa gat cgg gga      144
Glu Thr Gly Ala Ala Thr Val Ala Ile Tyr Pro Arg Glu Asp Arg Gly
        35                  40                  45 tca ttc cac cgc tct ttt gct tct gaa gct gtc cgc att ggt act gaa      192
Ser Phe His Arg Ser Phe Ala Ser Glu Ala Val Arg Ile Gly Thr Glu
    50                  55                  60 ggc tca cca gtc aag gcg tac ctg gac atc gat gaa att atc ggt gca      240
Gly Ser Pro Val Lys Ala Tyr Leu Asp Ile Asp Glu Ile Ile Gly Ala
65                  70                  75                  80 gct aaa aaa gtt aaa gca gat gct att tac ccg gga tat ggc ttc ctg      288
Ala Lys Lys Val Lys Ala Asp Ala Ile Tyr Pro Gly Tyr Gly Phe Leu
                85                  90                  95 tct gaa aat gcc cag ctt gcc cgc gag tgc gcg gaa aac ggc att act      336
Ser Glu Asn Ala Gln Leu Ala Arg Glu Cys Ala Glu Asn Gly Ile Thr
            100                 105                 110 ttt att ggc cca acc cca gag gtt ctt gat ctc acc ggt gat aag tct      384
Phe Ile Gly Pro Thr Pro Glu Val Leu Asp Leu Thr Gly Asp Lys Ser
        115                 120                 125 cgt gcg gta acc gcc gcg aag aag gct ggt ctg cca gtt ttg gcg gaa      432
Arg Ala Val Thr Ala Ala Lys Lys Ala Gly Leu Pro Val Leu Ala Glu
    130                 135                 140 tcc acc ccg agc aaa aac atc gat gac atc gtt aaa agc gct gaa ggc      480
Ser Thr Pro Ser Lys Asn Ile Asp Asp Ile Val Lys Ser Ala Glu Gly
145                 150                 155                 160 cag act tac ccc atc ttt gta aag gca gtt gcc ggt ggt ggc gga cgc      528
Gln Thr Tyr Pro Ile Phe Val Lys Ala Val Ala Gly Gly Gly Gly Arg
                165                 170                 175 ggt atg cgc ttt gtt tct tca cct gat gag ctt cgc aaa ttg gca aca      576
Gly Met Arg Phe Val Ser Ser Pro Asp Glu Leu Arg Lys Leu Ala Thr
            180                 185                 190 gaa gca tct cgt gaa gct gaa gcg gca ttc ggc gac ggt tcg gta tat      624
Glu Ala Ser Arg Glu Ala Glu Ala Ala Phe Gly Asp Gly Ser Val Tyr
        195                 200                 205
```

|                                                                                     |      |
|-------------------------------------------------------------------------------------|------|
| gtc gag cgt gct gtg att aac ccc cag cac att gaa gtg cag atc ctt                     | 672  |
| Val Glu Arg Ala Val Ile Asn Pro Gln His Ile Glu Val Gln Ile Leu                     |      |
|     210             215             220                                             |      |
| ggc gat cgc act gga gaa gtt gta cac ctt tat gaa cgt gac tgc tca                     | 720  |
| Gly Asp Arg Thr Gly Glu Val Val His Leu Tyr Glu Arg Asp Cys Ser                     |      |
| 225             230             235             240                                 |      |
| ctg cag cgt cgt cac caa aaa gtt gtc gaa att gcg cca gca cag cat                     | 768  |
| Leu Gln Arg Arg His Gln Lys Val Val Glu Ile Ala Pro Ala Gln His                     |      |
|             245             250             255                                     |      |
| ttg gat cca gaa ctg cgt gat cgc att tgt gcg gat gca gta aag ttc                     | 816  |
| Leu Asp Pro Glu Leu Arg Asp Arg Ile Cys Ala Asp Ala Val Lys Phe                     |      |
|         260             265             270                                         |      |
| tgc cgc tcc att ggt tac cag ggc gcg gga act gtg gaa ttc ttg gtc                     | 864  |
| Cys Arg Ser Ile Gly Tyr Gln Gly Ala Gly Thr Val Glu Phe Leu Val                     |      |
|     275             280             285                                             |      |
| gat gaa aag ggc aac cac gtt ttc atc gaa atg aac cca cgt atc cag                     | 912  |
| Asp Glu Lys Gly Asn His Val Phe Ile Glu Met Asn Pro Arg Ile Gln                     |      |
| 290             295             300                                                 |      |
| gtt gag cac acc gtg act gaa gaa gtc acc gag gtg gac ctg gtg aag                     | 960  |
| Val Glu His Thr Val Thr Glu Glu Val Thr Glu Val Asp Leu Val Lys                     |      |
| 305             310             315             320                                 |      |
| gcg cag atg cgc ttg gct gct ggt gca acc ttg aag gaa ttg ggt ctg                     | 1008 |
| Ala Gln Met Arg Leu Ala Ala Gly Ala Thr Leu Lys Glu Leu Gly Leu                     |      |
|             325             330             335                                     |      |
| acc caa gat aag atc aag acc cac ggt gcg gca ctg cag tgc cgc atc                     | 1056 |
| Thr Gln Asp Lys Ile Lys Thr His Gly Ala Ala Leu Gln Cys Arg Ile                     |      |
|         340             345             350                                         |      |
| acc acg gaa gat cca aac aac ggc ttc cgc cca gat acc gga act atc                     | 1104 |
| Thr Thr Glu Asp Pro Asn Asn Gly Phe Arg Pro Asp Thr Gly Thr Ile                     |      |
|     355             360             365                                             |      |
| acc gcg tac cgc tca cca ggc gga gct ggc gtt cgt ctt gac ggt gca                     | 1152 |
| Thr Ala Tyr Arg Ser Pro Gly Gly Ala Gly Val Arg Leu Asp Gly Ala                     |      |
| 370             375             380                                                 |      |
| gct cag ctc ggt ggc gaa atc acc gca cac ttt gac tcc atg ctg gtg                     | 1200 |
| Ala Gln Leu Gly Gly Glu Ile Thr Ala His Phe Asp Ser Met Leu Val                     |      |
| 385             390             395             400                                 |      |
| aaa atg acc tgc cgt ggt tcc gat ttt gaa act gct gtt gct cgt gca                     | 1248 |
| Lys Met Thr Cys Arg Gly Ser Asp Phe Glu Thr Ala Val Ala Arg Ala                     |      |
|             405             410             415                                     |      |
| cag cgc gcg ttg gct gag ttc acc gtg tct ggt gtt gca acc aac att                     | 1296 |
| Gln Arg Ala Leu Ala Glu Phe Thr Val Ser Gly Val Ala Thr Asn Ile                     |      |
|         420             425             430                                         |      |
| ggt ttc ttg cgt gcg ttg ctg cgt gaa gag gac ttt act tcc aag cgc                     | 1344 |
| Gly Phe Leu Arg Ala Leu Leu Arg Glu Glu Asp Phe Thr Ser Lys Arg                     |      |
|     435             440             445                                             |      |
| atc gcc acc gga ttt atc ggc gat cac cca cac ctc ctt cag gct cca                     | 1392 |
| Ile Ala Thr Gly Phe Ile Gly Asp His Pro His Leu Leu Gln Ala Pro                     |      |
| 450             455             460                                                 |      |
| cct gcg gat gat gag cag gga cgc atc ctg gat tac ttg gca gat gtc                     | 1440 |
| Pro Ala Asp Asp Glu Gln Gly Arg Ile Leu Asp Tyr Leu Ala Asp Val                     |      |
| 465             470             475             480                                 |      |
| acc gtg aac aag cct cat ggt gtg cgt cca aag gat gtt gca gca cca                     | 1488 |
| Thr Val Asn Lys Pro His Gly Val Arg Pro Lys Asp Val Ala Ala Pro                     |      |
|             485             490             495                                     |      |
| atc gat aag ctg ccc aac atc aag gat ctg cca ctg cca cgc ggt tcc                     | 1536 |
| Ile Asp Lys Leu Pro Asn Ile Lys Asp Leu Pro Leu Pro Arg Gly Ser                     |      |
|         500             505             510                                         |      |
| cgt gac cgc ctg aag cag ctt gga cca gca gcg ttt gcc cgc gat ctc                     | 1584 |
| Arg Asp Arg Leu Lys Gln Leu Gly Pro Ala Ala Phe Ala Arg Asp Leu                     |      |
|     515             520             525                                             |      |

| | | |
|---|---|---|
| cgt gag cag gac gca ctg gca gtt act gat acc acc ttc cgc gat gca | | 1632 |
| Arg Glu Gln Asp Ala Leu Ala Val Thr Asp Thr Thr Phe Arg Asp Ala | | |
| 530 535 540 | | |
| cac cag tct ttg ctt gcg acc cga gtc cgc tca ttc gca ctg aag cct | | 1680 |
| His Gln Ser Leu Leu Ala Thr Arg Val Arg Ser Phe Ala Leu Lys Pro | | |
| 545 550 555 560 | | |
| gcg gca gag gcc gtc gca aag ctg act cct gag ctt ttg tcc gtg gag | | 1728 |
| Ala Ala Glu Ala Val Ala Lys Leu Thr Pro Glu Leu Leu Ser Val Glu | | |
| 565 570 575 | | |
| gcc tgg ggc ggt gcg acc tac gat gtg gcg atg cgt ttc ctc ttt gag | | 1776 |
| Ala Trp Gly Gly Ala Thr Tyr Asp Val Ala Met Arg Phe Leu Phe Glu | | |
| 580 585 590 | | |
| gat ccg tgg gac agg ctc gac gag ctg cgc gag gcg atg ccg aat gtg | | 1824 |
| Asp Pro Trp Asp Arg Leu Asp Glu Leu Arg Glu Ala Met Pro Asn Val | | |
| 595 600 605 | | |
| aac att cag atg ctg ctt cgc ggc cgc aac acc gtg gga tac acc cca | | 1872 |
| Asn Ile Gln Met Leu Leu Arg Gly Arg Asn Thr Val Gly Tyr Thr Pro | | |
| 610 615 620 | | |
| tac cca gac tcc gtc tgt cgc gcg ttt gtt aag gaa gct gcc acc tcc | | 1920 |
| Tyr Pro Asp Ser Val Cys Arg Ala Phe Val Lys Glu Ala Ala Thr Ser | | |
| 625 630 635 640 | | |
| ggc gtg gac atc ttc cgc atc ttc gac gcg ctt aac gac gtc tcc cag | | 1968 |
| Gly Val Asp Ile Phe Arg Ile Phe Asp Ala Leu Asn Asp Val Ser Gln | | |
| 645 650 655 | | |
| atg cgt cca gca atc gac gca gtc ctg gag acc aac acc gcg gtc gct | | 2016 |
| Met Arg Pro Ala Ile Asp Ala Val Leu Glu Thr Asn Thr Ala Val Ala | | |
| 660 665 670 | | |
| gaa gtg gct atg gct tat tct ggt gat ctt tcc gat ccg aat gaa aag | | 2064 |
| Glu Val Ala Met Ala Tyr Ser Gly Asp Leu Ser Asp Pro Asn Glu Lys | | |
| 675 680 685 | | |
| ctc tac acc ctg gat tac tac ctg aag atg gca gag gag atc gtc aag | | 2112 |
| Leu Tyr Thr Leu Asp Tyr Tyr Leu Lys Met Ala Glu Glu Ile Val Lys | | |
| 690 695 700 | | |
| tct ggc gct cac att ctg gct att aag gat atg gct ggt ctg ctt cgc | | 2160 |
| Ser Gly Ala His Ile Leu Ala Ile Lys Asp Met Ala Gly Leu Leu Arg | | |
| 705 710 715 720 | | |
| cca gct gca gcc acc aag ctg gtc acc gca ctg cgc cgt gaa ttt gat | | 2208 |
| Pro Ala Ala Ala Thr Lys Leu Val Thr Ala Leu Arg Arg Glu Phe Asp | | |
| 725 730 735 | | |
| ctg cca gtg cac gtg cac acc cac gac act gcg ggt ggc cag ctg gca | | 2256 |
| Leu Pro Val His Val His Thr His Asp Thr Ala Gly Gly Gln Leu Ala | | |
| 740 745 750 | | |
| acc tac ttt gct gca gct caa gct ggt gca gat gct gtt gac ggt gct | | 2304 |
| Thr Tyr Phe Ala Ala Ala Gln Ala Gly Ala Asp Ala Val Asp Gly Ala | | |
| 755 760 765 | | |
| tcc gca cca ctg tct ggc acc acc tcc cag cca tcc ctg tct gcc att | | 2352 |
| Ser Ala Pro Leu Ser Gly Thr Thr Ser Gln Pro Ser Leu Ser Ala Ile | | |
| 770 775 780 | | |
| gtt gct gca ttc gcg cac acc cgt cgc gat acc ggt ttg agc ctc gag | | 2400 |
| Val Ala Ala Phe Ala His Thr Arg Arg Asp Thr Gly Leu Ser Leu Glu | | |
| 785 790 795 800 | | |
| gct gtt tct gac ctc gag cca tac tgg gaa gca gtg cgc gga ctg tac | | 2448 |
| Ala Val Ser Asp Leu Glu Pro Tyr Trp Glu Ala Val Arg Gly Leu Tyr | | |
| 805 810 815 | | |
| ctg cca ttt gag tct gga acc cca ggc cca acc ggt cgc gtc tac cgc | | 2496 |
| Leu Pro Phe Glu Ser Gly Thr Pro Gly Pro Thr Gly Arg Val Tyr Arg | | |
| 820 825 830 | | |
| cac gaa atc cca ggc gga cag ctg tcc aac ctg cgt gca cag gcc acc | | 2544 |
| His Glu Ile Pro Gly Gly Gln Leu Ser Asn Leu Arg Ala Gln Ala Thr | | |
| 835 840 845 | | |

```
gca ctg ggc ctt gcg gat cgt ttc gaa ctc atc gaa gac aac tac gcg      2592
Ala Leu Gly Leu Ala Asp Arg Phe Glu Leu Ile Glu Asp Asn Tyr Ala
850                 855                 860 gca gtt aat gag atg ctg gga cgc cca acc aag gtc acc cca tcc tcc      2640
Ala Val Asn Glu Met Leu Gly Arg Pro Thr Lys Val Thr Pro Ser Ser
865                 870                 875                 880 aag gtt gtt ggc gac ctc gca ctc cac ctc gtt ggt gcg ggt gtg gat      2688
Lys Val Val Gly Asp Leu Ala Leu His Leu Val Gly Ala Gly Val Asp
                885                 890                 895 cca gca gac ttt gct gca gat cca caa aag tac gac atc cca gac tct      2736
Pro Ala Asp Phe Ala Ala Asp Pro Gln Lys Tyr Asp Ile Pro Asp Ser
        900                 905                 910 gtc atc gcg ttc ctg cgc ggt gag ctt ggt aac cct cca ggt ggc tgg      2784
Val Ile Ala Phe Leu Arg Gly Glu Leu Gly Asn Pro Pro Gly Gly Trp
            915                 920                 925 cca gag cca ctg cgc acc cgc gca ctg gaa ggc cgc tcc gaa ggc aag      2832
Pro Glu Pro Leu Arg Thr Arg Ala Leu Glu Gly Arg Ser Glu Gly Lys
930                 935                 940 gca cct ctg acg gaa gtt cct gag gaa gag cag gcg cac ctc gac gct      2880
Ala Pro Leu Thr Glu Val Pro Glu Glu Glu Gln Ala His Leu Asp Ala
945                 950                 955                 960 gat gat tcc aag gaa cgt cgc aac agc ctc aac cgc ctg ctg ttc ccg      2928
Asp Asp Ser Lys Glu Arg Arg Asn Ser Leu Asn Arg Leu Leu Phe Pro
                965                 970                 975 aag cca acc gaa gag ttc ctc gag cac cgt cgc cgc ttc ggc aac acc      2976
Lys Pro Thr Glu Glu Phe Leu Glu His Arg Arg Arg Phe Gly Asn Thr
        980                 985                 990 tct gcg ctg gat gat cgt gaa ttc ttc tac ggc ctg gtc gaa ggc cgc      3024
Ser Ala Leu Asp Asp Arg Glu Phe Phe Tyr Gly Leu Val Glu Gly Arg
            995                 1000                1005 gag act ttg atc cgc ctg cca gat gtg cgc acc cca ctg ctt gtt         3069
Glu Thr Leu Ile Arg Leu Pro Asp Val Arg Thr Pro Leu Leu Val
1010                1015                1020 cgc ctg gat gcg atc tcc gag cca gac gat aag ggt atg cgc aat         3114
Arg Leu Asp Ala Ile Ser Glu Pro Asp Asp Lys Gly Met Arg Asn
1025                1030                1035 gtt gtg gcc aac gtc aac ggc cag atc cgc cca atg cgt gtg cgt         3159
Val Val Ala Asn Val Asn Gly Gln Ile Arg Pro Met Arg Val Arg
1040                1045                1050 gac cgc tcc gtt gag tct gtc acc gca acc gca gaa aag gca gat         3204
Asp Arg Ser Val Glu Ser Val Thr Ala Thr Ala Glu Lys Ala Asp
1055                1060                1065 tcc tcc aac aag ggc cat gtt gct gca cca ttc gct ggt gtt gtc         3249
Ser Ser Asn Lys Gly His Val Ala Ala Pro Phe Ala Gly Val Val
1070                1075                1080 act gtg act gtt gct gaa ggt gat gag gtc aag gct gga gat gca         3294
Thr Val Thr Val Ala Glu Gly Asp Glu Val Lys Ala Gly Asp Ala
1085                1090                1095 gtc gca atc atc gag gct atg aag atg gaa gca aca atc act gct         3339
Val Ala Ile Ile Glu Ala Met Lys Met Glu Ala Thr Ile Thr Ala
1100                1105                1110 tct gtt gac ggc aaa atc gat cgc gtt gtg gtt cct gct gca acg         3384
Ser Val Asp Gly Lys Ile Asp Arg Val Val Val Pro Ala Ala Thr
1115                1120                1125 aag gtg gaa ggt ggc gac ttg atc gtc gtc gtt tcc                     3420
Lys Val Glu Gly Gly Asp Leu Ile Val Val Val Ser
1130                1135                1140

<210> SEQ ID NO 18
<211> LENGTH: 1140
<212> TYPE: PRT
```

<210> ORGANISM: Brevibacterium fluvum

<400> SEQUENCE: 18

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
130                 135                 140

Ser Thr Pro Ser Lys Asn Ile Asp Asp Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ser Ser Pro Asp Glu Leu Arg Lys Leu Ala Thr
            180                 185                 190

Glu Ala Ser Arg Glu Ala Glu Ala Ala Phe Gly Asp Gly Ser Val Tyr
        195                 200                 205

Val Glu Arg Ala Val Ile Asn Pro Gln His Ile Glu Val Gln Ile Leu
    210                 215                 220

Gly Asp Arg Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala

```
                    405                 410                 415
Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
            435                 440                 445

Ile Ala Thr Gly Phe Ile Gly Asp His Pro His Leu Leu Gln Ala Pro
        450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Thr Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Ala Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
    770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830
```

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                 1005

Glu Thr Leu Ile Arg Leu Pro Asp Val Arg Thr Pro Leu Leu Val
        1010                 1015                 1020

Arg Leu Asp Ala Ile Ser Glu Pro Asp Asp Lys Gly Met Arg Asn
        1025                 1030                 1035

Val Val Ala Asn Val Asn Gly Gln Ile Arg Pro Met Arg Val Arg
        1040                 1045                 1050

Asp Arg Ser Val Glu Ser Val Thr Ala Thr Ala Glu Lys Ala Asp
        1055                 1060                 1065

Ser Ser Asn Lys Gly His Val Ala Ala Pro Phe Ala Gly Val Val
        1070                 1075                 1080

Thr Val Thr Val Ala Glu Gly Asp Glu Val Lys Ala Gly Asp Ala
        1085                 1090                 1095

Val Ala Ile Ile Glu Ala Met Lys Met Glu Ala Thr Ile Thr Ala
        1100                 1105                 1110

Ser Val Asp Gly Lys Ile Asp Arg Val Val Val Pro Ala Ala Thr
        1115                 1120                 1125

Lys Val Glu Gly Gly Asp Leu Ile Val Val Val Ser
        1130                 1135                 1140

<210> SEQ ID NO 19
<211> LENGTH: 22
<212> TYPE: DNA
<213> ORGANISM: Artificial Sequence
<220> FEATURE:
<223> OTHER INFORMATION: primer for amplifying yidE

<400> SEQUENCE: 19
cgggatccgc cataatccgt ag                                                22

<210> SEQ ID NO 20
<211> LENGTH: 990
<212> TYPE: DNA
<213> ORGANISM: Escherichia coli
<220> FEATURE:
<221> NAME/KEY: CDS
<222> LOCATION: (1)..(990)

<400> SEQUENCE: 20

```
atg aaa ctc gcc gtt tat agc aca aaa cag tac gac aag aag tac ctg        48
Met Lys Leu Ala Val Tyr Ser Thr Lys Gln Tyr Asp Lys Lys Tyr Leu
 1               5                  10                  15 caa cag gtg aac gag tcc ttt ggc ttt gag ctg gaa ttt ttt gac ttt        96
Gln Gln Val Asn Glu Ser Phe Gly Phe Glu Leu Glu Phe Phe Asp Phe
             20                  25                  30 ctg ctg acg gaa aaa acc gct aaa act gcc aat ggc tgc gaa gcg gta       144
Leu Leu Thr Glu Lys Thr Ala Lys Thr Ala Asn Gly Cys Glu Ala Val
         35                  40                  45 tgt att ttc gta aac gat gac ggc agc cgc ccg gtg ctg gaa gag ctg       192
Cys Ile Phe Val Asn Asp Asp Gly Ser Arg Pro Val Leu Glu Glu Leu
     50                  55                  60 aaa aag cac ggc gtt aaa tat atc gcc ctg cgc tgt gcc ggt ttc aat       240
Lys Lys His Gly Val Lys Tyr Ile Ala Leu Arg Cys Ala Gly Phe Asn
 65                  70                  75                  80 aac gtc gac ctt gac gcg gca aaa gaa ctg ggg ctg aaa gta gtc cgt       288
Asn Val Asp Leu Asp Ala Ala Lys Glu Leu Gly Leu Lys Val Val Arg
                 85                  90                  95 gtt cca gcc tat gat cca gag gcc gtt gct gaa cac gcc atc ggt atg       336
Val Pro Ala Tyr Asp Pro Glu Ala Val Ala Glu His Ala Ile Gly Met
            100                 105                 110 atg atg acg ctg aac cgc cgt att cac cgc gcg tat cag cgt acc cgt       384
Met Met Thr Leu Asn Arg Arg Ile His Arg Ala Tyr Gln Arg Thr Arg
        115                 120                 125 gat gct aac ttc tct ctg gaa ggt ctg acc ggc ttt act atg tat ggc       432
Asp Ala Asn Phe Ser Leu Glu Gly Leu Thr Gly Phe Thr Met Tyr Gly
    130                 135                 140 aaa acg gca ggc gtt atc ggt acc ggt aaa atc ggt gtg gcg atg ctg       480
Lys Thr Ala Gly Val Ile Gly Thr Gly Lys Ile Gly Val Ala Met Leu
145                 150                 155                 160 cgc att ctg aaa ggt ttt ggt atg cgt ctg ctg gcg ttc gat ccg tat       528
Arg Ile Leu Lys Gly Phe Gly Met Arg Leu Leu Ala Phe Asp Pro Tyr
                165                 170                 175 cca agt gca gcg gcg ctg gaa ctc ggt gtg gag tat gtc gat ctg cca       576
Pro Ser Ala Ala Ala Leu Glu Leu Gly Val Glu Tyr Val Asp Leu Pro
            180                 185                 190 acc ctg ttc tct gaa tca gac gtt atc tct ctg cac tgc ccg ctg aca       624
Thr Leu Phe Ser Glu Ser Asp Val Ile Ser Leu His Cys Pro Leu Thr
        195                 200                 205 ccg gaa aac tat cat ctg ttg aac gaa gcc gcc ttc gaa cag atg aaa       672
Pro Glu Asn Tyr His Leu Leu Asn Glu Ala Ala Phe Glu Gln Met Lys
    210                 215                 220 aat ggc gtg atg atc gtc aat acc agc cgc ggt gca ttg att gat tct       720
Asn Gly Val Met Ile Val Asn Thr Ser Arg Gly Ala Leu Ile Asp Ser
225                 230                 235                 240 cag gca gca att gaa gcg ctg aaa aat cag aaa att ggt tcg ttg ggt       768
Gln Ala Ala Ile Glu Ala Leu Lys Asn Gln Lys Ile Gly Ser Leu Gly
                245                 250                 255 atg gac gtg tat gag aac gaa cgc gat cta ttc ttt gaa gat aaa tcc       816
Met Asp Val Tyr Glu Asn Glu Arg Asp Leu Phe Phe Glu Asp Lys Ser
            260                 265                 270 aac gac gtg atc cag gat gac gta ttc cgt cgc ctg tct gcc tgc cac       864
Asn Asp Val Ile Gln Asp Asp Val Phe Arg Arg Leu Ser Ala Cys His
        275                 280                 285 aac gtg ctg ttt acc ggg cac cag gca ttc ctg aca gca gaa gct ctg       912
Asn Val Leu Phe Thr Gly His Gln Ala Phe Leu Thr Ala Glu Ala Leu
    290                 295                 300 acc agt att tct cag act acg ctg caa aac tta agc aat ctg gaa aaa       960
Thr Ser Ile Ser Gln Thr Thr Leu Gln Asn Leu Ser Asn Leu Glu Lys
```

```
Thr Ser Ile Ser Gln Thr Thr Leu Gln Asn Leu Ser Asn Leu Glu Lys
305                 310                 315                 320 ggc gaa acc tgc ccg aac gaa ctg gtt taa                          990
Gly Glu Thr Cys Pro Asn Glu Leu Val
                325

<210> SEQ ID NO 21
<211> LENGTH: 329
<212> TYPE: PRT
<213> ORGANISM: Escherichia coli

<400> SEQUENCE: 21

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325

<210> SEQ ID NO 22
```

```
<211> LENGTH: 1191
<212> TYPE: DNA
<213> ORGANISM: Escherichia coli
<220> FEATURE:
<221> NAME/KEY: CDS
<222> LOCATION: (1)..(1191)

<400> SEQUENCE: 22 atg att att tcc gca gcc agc gat tat cgc gcc gca gcg caa cgc att        48
Met Ile Ile Ser Ala Ala Ser Asp Tyr Arg Ala Ala Ala Gln Arg Ile
1               5                   10                  15 ctg ccg ccg ttc ctg ttc cac tat atg gat ggt ggt gca tat tct gaa        96
Leu Pro Pro Phe Leu Phe His Tyr Met Asp Gly Gly Ala Tyr Ser Glu
                20                  25                  30 tac acg ctg cgc cgc aac gtg gaa gat ttg tca gaa gtg gcg ctg cgc       144
Tyr Thr Leu Arg Arg Asn Val Glu Asp Leu Ser Glu Val Ala Leu Arg
            35                  40                  45 cag cgt att ctg aaa aac atg tcc gac tta agc ctg gaa acg acg ctg       192
Gln Arg Ile Leu Lys Asn Met Ser Asp Leu Ser Leu Glu Thr Thr Leu
        50                  55                  60 ttt aat gag aaa ttg tcg atg ccg gtg gca ctg gct ccg gtg ggt ttg       240
Phe Asn Glu Lys Leu Ser Met Pro Val Ala Leu Ala Pro Val Gly Leu
65                  70                  75                  80 tgt ggc atg tat gcg cgt cgt ggc gaa gtt cag gca gcc aaa gcg gcg       288
Cys Gly Met Tyr Ala Arg Arg Gly Glu Val Gln Ala Ala Lys Ala Ala
                85                  90                  95 gac gcg cat ggt att ccg ttt act ctc tcg acg gtt tcc gtt tgc ccg       336
Asp Ala His Gly Ile Pro Phe Thr Leu Ser Thr Val Ser Val Cys Pro
                100                 105                 110 att gaa gaa gtc gcg cca gcc atc aag cgc cca atg tgg ttc cag ctt       384
Ile Glu Glu Val Ala Pro Ala Ile Lys Arg Pro Met Trp Phe Gln Leu
            115                 120                 125 tat gta ctg cgc gat cgc ggc ttt atg cgt aac gcg ctg gag cga gca       432
Tyr Val Leu Arg Asp Arg Gly Phe Met Arg Asn Ala Leu Glu Arg Ala
        130                 135                 140 aaa gca gcg ggt tgt tcg acg ctg gtt ttc acc gtg gat atg ccg aca       480
Lys Ala Ala Gly Cys Ser Thr Leu Val Phe Thr Val Asp Met Pro Thr
145                 150                 155                 160 ccg ggc gca cgc tac cgt gat gcg cat tca ggt atg agc ggc ccg aac       528
Pro Gly Ala Arg Tyr Arg Asp Ala His Ser Gly Met Ser Gly Pro Asn
                165                 170                 175 gcg gca atg cgc cgc tac ttg caa gcg gtg aca cat ccg caa tgg gcg       576
Ala Ala Met Arg Arg Tyr Leu Gln Ala Val Thr His Pro Gln Trp Ala
                180                 185                 190 tgg gat gtg ggc ctg aac ggt cgt cca cat gat tta ggt aat atc tca       624
Trp Asp Val Gly Leu Asn Gly Arg Pro His Asp Leu Gly Asn Ile Ser
            195                 200                 205 gct tat ctc ggc aaa ccg acc gga ctg gaa gat tac atc ggc tgg ctg       672
Ala Tyr Leu Gly Lys Pro Thr Gly Leu Glu Asp Tyr Ile Gly Trp Leu
        210                 215                 220 ggg aat aac ttc gat ccg tcc atc tca tgg aaa gac ctt gaa tgg atc       720
Gly Asn Asn Phe Asp Pro Ser Ile Ser Trp Lys Asp Leu Glu Trp Ile
225                 230                 235                 240 cgc gat ttc tgg gat ggc ccg atg gtg atc aaa ggg atc ctc gat ccg       768
Arg Asp Phe Trp Asp Gly Pro Met Val Ile Lys Gly Ile Leu Asp Pro
                245                 250                 255 gaa gat gcg cgc gat gca gta cgt ttt ggt gct gat gga att gtg gtt       816
Glu Asp Ala Arg Asp Ala Val Arg Phe Gly Ala Asp Gly Ile Val Val
                260                 265                 270 tct aac cac ggt ggc cgc cag ctg gac ggt gta ctc tct tcc gcc cgt       864
Ser Asn His Gly Gly Arg Gln Leu Asp Gly Val Leu Ser Ser Ala Arg
            275                 280                 285
```

```
gca ctg cct gct att gca gat gcg gtg aaa ggt gat ata gcc att ctg      912
Ala Leu Pro Ala Ile Ala Asp Ala Val Lys Gly Asp Ile Ala Ile Leu
        290                 295                 300 gcg gat agc gga att cgt aac ggg ctt gat gtc gtg cgt atg att gcg      960
Ala Asp Ser Gly Ile Arg Asn Gly Leu Asp Val Val Arg Met Ile Ala
305                 310                 315                 320 ctc ggt gcc gac acc gta ctg ctg ggt cgt gct ttc ttg tat gcg ctg     1008
Leu Gly Ala Asp Thr Val Leu Leu Gly Arg Ala Phe Leu Tyr Ala Leu
                325                 330                 335 gca aca gcg ggc cag gcg ggt gta gct aac ctg cta aat ctg atc gaa     1056
Ala Thr Ala Gly Gln Ala Gly Val Ala Asn Leu Leu Asn Leu Ile Glu
            340                 345                 350 aaa gag atg aaa gtg gcg atg acg ctg act ggc gcg aaa tcg atc agc     1104
Lys Glu Met Lys Val Ala Met Thr Leu Thr Gly Ala Lys Ser Ile Ser
        355                 360                 365 gaa att acg caa gat tcg ctg gtg cag ggg ctg ggt aaa gag ttg cct     1152
Glu Ile Thr Gln Asp Ser Leu Val Gln Gly Leu Gly Lys Glu Leu Pro
370                 375                 380 gcg gca ctg gct ccc atg gcg aaa ggg aat gcg gca tag              1191
Ala Ala Leu Ala Pro Met Ala Lys Gly Asn Ala Ala
385                 390                 395

<210> SEQ ID NO 23
<211> LENGTH: 396
<212> TYPE: PRT
<213> ORGANISM: Escherichia coli

<400> SEQUENCE: 23

Met Ile Ile Ser Ala Ala Ser Asp Tyr Arg Ala Ala Ala Gln Arg Ile
1               5                   10                  15

Leu Pro Pro Phe Leu Phe His Tyr Met Asp Gly Gly Ala Tyr Ser Glu
            20                  25                  30

Tyr Thr Leu Arg Arg Asn Val Glu Asp Leu Ser Glu Val Ala Leu Arg
        35                  40                  45

Gln Arg Ile Leu Lys Asn Met Ser Asp Leu Ser Leu Glu Thr Thr Leu
    50                  55                  60

Phe Asn Glu Lys Leu Ser Met Pro Val Ala Leu Ala Pro Val Gly Leu
65                  70                  75                  80

Cys Gly Met Tyr Ala Arg Arg Gly Glu Val Gln Ala Ala Lys Ala Ala
                85                  90                  95

Asp Ala His Gly Ile Pro Phe Thr Leu Ser Thr Val Ser Val Cys Pro
            100                 105                 110

Ile Glu Glu Val Ala Pro Ala Ile Lys Arg Pro Met Trp Phe Gln Leu
        115                 120                 125

Tyr Val Leu Arg Asp Arg Gly Phe Met Arg Asn Ala Leu Glu Arg Ala
    130                 135                 140

Lys Ala Ala Gly Cys Ser Thr Leu Val Phe Thr Val Asp Met Pro Thr
145                 150                 155                 160

Pro Gly Ala Arg Tyr Arg Asp Ala His Ser Gly Met Ser Gly Pro Asn
                165                 170                 175

Ala Ala Met Arg Arg Tyr Leu Gln Ala Val Thr His Pro Gln Trp Ala
            180                 185                 190

Trp Asp Val Gly Leu Asn Gly Arg Pro His Asp Leu Gly Asn Ile Ser
        195                 200                 205

Ala Tyr Leu Gly Lys Pro Thr Gly Leu Glu Asp Tyr Ile Gly Trp Leu
    210                 215                 220

Gly Asn Asn Phe Asp Pro Ser Ile Ser Trp Lys Asp Leu Glu Trp Ile
```

```
                225                 230                 235                 240
Arg Asp Phe Trp Asp Gly Pro Met Val Ile Lys Gly Ile Leu Asp Pro
                            245                 250                 255

Glu Asp Ala Arg Asp Ala Val Arg Phe Gly Ala Asp Gly Ile Val Val
                260                 265                 270

Ser Asn His Gly Gly Arg Gln Leu Asp Gly Val Leu Ser Ser Ala Arg
            275                 280                 285

Ala Leu Pro Ala Ile Ala Asp Ala Val Lys Gly Asp Ile Ala Ile Leu
        290                 295                 300

Ala Asp Ser Gly Ile Arg Asn Gly Leu Asp Val Val Arg Met Ile Ala
305                 310                 315                 320

Leu Gly Ala Asp Thr Val Leu Leu Gly Arg Ala Phe Leu Tyr Ala Leu
                325                 330                 335

Ala Thr Ala Gly Gln Ala Gly Val Ala Asn Leu Leu Asn Leu Ile Glu
                340                 345                 350

Lys Glu Met Lys Val Ala Met Thr Leu Thr Gly Ala Lys Ser Ile Ser
            355                 360                 365

Glu Ile Thr Gln Asp Ser Leu Val Gln Gly Leu Gly Lys Glu Leu Pro
        370                 375                 380

Ala Ala Leu Ala Pro Met Ala Lys Gly Asn Ala Ala
385                 390                 395

<210> SEQ ID NO 24
<211> LENGTH: 553
<212> TYPE: PRT
<213> ORGANISM: Artificial Sequence
<220> FEATURE:
<223> OTHER INFORMATION: conserved sequence
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
```

```
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (150)..(152)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (177)..(178)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (197)..(198)
<223> OTHER INFORMATION: Xaa can be any naturally occurring amino acid
<220> FEATURE:
<221> NAME/KEY: misc_feature
<222> LOCATION: (201)..(202)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (217)..(219)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (240)..(241)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
```

-continued

```
<221> NAME/KEY: misc_feature
<222> LOCATION: (264)..(265)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid
<220> FEATURE:
<221> NAME/KEY: misc_feature
<222> LOCATION: (350)..(351)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (444)..(444)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (459)..(460)
<223> OTHER INFORMATION: Xaa can be any naturally occurring amino acid
<220> FEATURE:
<221> NAME/KEY: misc_feature
<222> LOCATION: (471)..(472)
<223> OTHER INFORMATION: Xaa can be any naturally occurring amino acid
<220> FEATURE:
<221> NAME/KEY: misc_feature
<222> LOCATION: (476)..(476)
<223> OTHER INFORMATION: Xaa can be any naturally occurring amino acid
<220> FEATURE:
<221> NAME/KEY: misc_feature
<222> LOCATION: (483)..(483)
<223> OTHER INFORMATION: Xaa can be any naturally occurring amino acid
<220> FEATURE:
<221> NAME/KEY: misc_feature
<222> LOCATION: (487)..(488)
<223> OTHER INFORMATION: Xaa can be any naturally occurring amino acid
<220> FEATURE:
<221> NAME/KEY: misc_feature
<222> LOCATION: (496)..(496)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid
<220> FEATURE:
<221> NAME/KEY: misc_feature
<222> LOCATION: (548)..(548)
<223> OTHER INFORMATION: Xaa can be any naturally occurring amino acid
<220> FEATURE:
```

<221> NAME/KEY: misc_feature
<222> LOCATION: (551)..(552)
<223> OTHER INFORMATION: Xaa can be any naturally occurring amino acid

<400> SEQUENCE: 24

```
Met Ser Asp Ile Ala Leu Thr Val Ser Xaa Leu Ala Leu Val Ala Val
1               5                   10                  15

Val Gly Leu Xaa Ile Gly Asn Xaa Lys Xaa Arg Gly Xaa Gly Xaa Gly
                20                  25                  30

Ile Gly Gly Val Leu Phe Gly Gly Ile Ile Val Gly His Phe Val Xaa
            35                  40                  45

Gln Ala Gly Xaa Thr Leu Ser Xaa Asp Met Leu His Xaa Ile Gln Glu
        50                  55                  60

Phe Gly Leu Ile Leu Phe Val Tyr Thr Ile Gly Ile Gln Val Gly Pro
65                  70                  75                  80

Gly Phe Phe Ala Ser Leu Arg Val Ser Gly Leu Arg Leu Asn Leu Phe
                85                  90                  95

Ala Val Leu Ile Val Ile Xaa Gly Gly Leu Val Thr Ala Ile Leu His
                100                 105                 110

Lys Xaa Phe Xaa Ile Pro Leu Pro Val Val Leu Gly Ile Phe Ser Gly
            115                 120                 125

Ala Val Thr Asn Thr Pro Ala Leu Gly Ala Gly Gln Gln Ile Leu Arg
        130                 135                 140

Asp Leu Gly Thr Pro Xaa Xaa Xaa Val Asp Gln Met Gly Met Ser Tyr
145                 150                 155                 160

Ala Met Ala Tyr Pro Phe Gly Ile Cys Gly Ile Leu Xaa Thr Met Trp
                165                 170                 175

Xaa Xaa Arg Xaa Ile Phe Arg Val Asn Val Glu Xaa Glu Ala Gln Xaa
                180                 185                 190

His Glu Ser Ser Xaa Xaa Asn Gly Xaa Xaa Leu Ile Xaa Thr Xaa Asn
            195                 200                 205

Ile Arg Val Glu Asn Pro Asn Leu Xaa Xaa Xaa Ala Ile Xaa Asp Val
            210                 215                 220

Pro Ile Leu Asn Xaa Asp Lys Ile Ile Cys Ser Arg Leu Lys Arg Xaa
225                 230                 235                 240

Xaa Thr Leu Xaa Val Pro Ser Pro Xaa Thr Ile Ile Gln Xaa Gly Asp
                245                 250                 255

Leu Leu His Leu Val Gly Gln Xaa Xaa Asp Leu His Asn Ala Gln Leu
            260                 265                 270

Val Ile Gly Xaa Glu Val Asp Thr Ser Leu Ser Thr Xaa Gly Thr Asp
            275                 280                 285

Leu Arg Val Glu Arg Val Val Thr Asn Glu Xaa Val Leu Gly Lys
290                 295                 300

Arg Ile Arg Asp Leu His Phe Lys Glu Arg Tyr Asp Val Val Ile Ser
305                 310                 315                 320

Arg Leu Asn Arg Ala Gly Val Glu Leu Val Ala Ser Xaa Asp Xaa Ser
                325                 330                 335

Leu Gln Phe Gly Asp Ile Leu Asn Leu Val Gly Arg Pro Xaa Xaa Ile
            340                 345                 350

Asp Ala Val Ala Asn Val Xaa Gly Asn Ala Gln Gln Lys Leu Gln Gln
            355                 360                 365

Val Gln Met Leu Pro Val Phe Ile Gly Ile Gly Leu Gly Val Leu Leu
        370                 375                 380

Gly Ser Ile Pro Xaa Phe Val Pro Gly Phe Pro Xaa Ala Leu Lys Leu
385                 390                 395                 400
```

```
Gly Leu Ala Gly Gly Pro Leu Ile Met Ala Leu Ile Leu Gly Arg Ile
                405                 410                 415
Gly Ser Ile Gly Lys Leu Tyr Trp Phe Met Pro Ser Ala Asn Leu
            420                 425                 430
Ala Leu Arg Glu Leu Gly Ile Val Leu Phe Leu Xaa Val Val Gly Leu
        435                 440                 445
Lys Ser Gly Gly Asp Phe Val Xaa Thr Leu Xaa Xaa Gly Glu Gly Leu
    450                 455                 460
Ser Trp Ile Gly Tyr Gly Xaa Xaa Ile Thr Ala Xaa Pro Leu Ile Thr
465                 470                 475                 480
Val Gly Xaa Leu Ala Arg Xaa Xaa Ala Lys Met Asn Tyr Leu Thr Xaa
            485                 490                 495
Cys Gly Met Leu Ala Gly Ser Met Thr Asp Pro Pro Ala Leu Ala Phe
            500                 505                 510
Ala Asn Asn Leu His Xaa Thr Ser Gly Ala Ala Leu Ser Tyr Ala
        515                 520                 525
Thr Val Tyr Pro Leu Val Met Phe Leu Arg Ile Ile Thr Pro Gln Leu
    530                 535                 540
Leu Ala Val Xaa Phe Trp Xaa Xaa Gly
545                 550

<210> SEQ ID NO 25
<211> LENGTH: 1662
<212> TYPE: DNA
<213> ORGANISM: Shigella flexneri
<220> FEATURE:
<221> NAME/KEY: CDS
<222> LOCATION: (1)..(1662)

<400> SEQUENCE: 25 atg agt gat ata gca tta acg gtc agt att ctg gct ttg gtg gca gtc      48
Met Ser Asp Ile Ala Leu Thr Val Ser Ile Leu Ala Leu Val Ala Val
1               5                   10                  15 gtc ggt ttg ttt atc ggc aac gtc aaa ttt cgc ggc ata gga tta ggt      96
Val Gly Leu Phe Ile Gly Asn Val Lys Phe Arg Gly Ile Gly Leu Gly
            20                  25                  30 att ggc ggc gtg ctg ttt ggt ggg atc atc gtc ggc cat ttt gtt tct     144
Ile Gly Gly Val Leu Phe Gly Gly Ile Ile Val Gly His Phe Val Ser
        35                  40                  45 cag gcg ggg atg aca tta agt agc gat atg ctg cat gtt att cag gaa     192
Gln Ala Gly Met Thr Leu Ser Ser Asp Met Leu His Val Ile Gln Glu
    50                  55                  60 ttt ggc ctg atc ctg ttc gtt tat acc atc ggg att cag gta ggg ccg     240
Phe Gly Leu Ile Leu Phe Val Tyr Thr Ile Gly Ile Gln Val Gly Pro
65                  70                  75                  80 ggc ttc ttt gcc tca ttg cgc gtc tcc gga tta cgc ctc aac ctg ttt     288
Gly Phe Phe Ala Ser Leu Arg Val Ser Gly Leu Arg Leu Asn Leu Phe
                85                  90                  95 gct gtt ctg atc gtc atc atc ggt ggt ctg gtt acc gcc atc ctg cat     336
Ala Val Leu Ile Val Ile Ile Gly Gly Leu Val Thr Ala Ile Leu His
            100                 105                 110 aaa ctg ttt gat att cca ctg ccg gta gtg ctg ggg att ttc tcc ggt     384
Lys Leu Phe Asp Ile Pro Leu Pro Val Val Leu Gly Ile Phe Ser Gly
        115                 120                 125 gcg gta acc aat acg cca gcg ctg ggg gca ggg cag cag atc ttg cgc     432
Ala Val Thr Asn Thr Pro Ala Leu Gly Ala Gly Gln Gln Ile Leu Arg
    130                 135                 140 gac ctg ggt aca cca atg gaa atg gtc gat cag atg ggg atg agt tac     480
Asp Leu Gly Thr Pro Met Glu Met Val Asp Gln Met Gly Met Ser Tyr
```

```
                145                 150                 155                 160
gcg atg gcg tat cca ttc ggc att tgc ggg att ttg ttc acc atg tgg        528
Ala Met Ala Tyr Pro Phe Gly Ile Cys Gly Ile Leu Phe Thr Met Trp
            165                 170                 175 atg ttg cgg gtt att ttc cgc gtc aat gtc gag aca gaa gct cag cag        576
Met Leu Arg Val Ile Phe Arg Val Asn Val Glu Thr Glu Ala Gln Gln
        180                 185                 190 cac gag tct tca cgc acc aat gcc ggc gcg ctg atc aag act atc aat        624
His Glu Ser Ser Arg Thr Asn Ala Gly Ala Leu Ile Lys Thr Ile Asn
    195                 200                 205 att cgc gtt gag aac cct aac cgg cat gat tta gcc att aaa gat gta        672
Ile Arg Val Glu Asn Pro Asn Arg His Asp Leu Ala Ile Lys Asp Val
210                 215                 220 ccg att ctc aac ggc gac aaa att atc tgc tcg cgt ctg aaa cga gaa        720
Pro Ile Leu Asn Gly Asp Lys Ile Ile Cys Ser Arg Leu Lys Arg Glu
225                 230                 235                 240 gaa acc cta aaa gta cct tcg cca gat acc att atc caa ctg ggc gat        768
Glu Thr Leu Lys Val Pro Ser Pro Asp Thr Ile Ile Gln Leu Gly Asp
            245                 250                 255 ttg ctg cat ctg gtg ggg cag cca gcg gat tta cat aat gcg caa ctg        816
Leu Leu His Leu Val Gly Gln Pro Ala Asp Leu His Asn Ala Gln Leu
        260                 265                 270 gtg att ggt cag gag gtc gat acc tcg ctg tct acg aaa ggc act gat        864
Val Ile Gly Gln Glu Val Asp Thr Ser Leu Ser Thr Lys Gly Thr Asp
    275                 280                 285 ttg cgc gtc gag cgt gtg gtg gtc acc aat gaa aac gtg ctc gga aaa        912
Leu Arg Val Glu Arg Val Val Val Thr Asn Glu Asn Val Leu Gly Lys
290                 295                 300 cgt att cgc gac ctg cac ttt aaa gaa cgc tat gac gtt gtt atc tcg        960
Arg Ile Arg Asp Leu His Phe Lys Glu Arg Tyr Asp Val Val Ile Ser
305                 310                 315                 320 cgc ctg aac cgt gcc ggg gtc gaa ctg gtc gcc agt ggc gat atc agc       1008
Arg Leu Asn Arg Ala Gly Val Glu Leu Val Ala Ser Gly Asp Ile Ser
            325                 330                 335 ctg cag ttc ggc gat atc ctc aac ctg gtg ggg cgt ccg tcc gca att       1056
Leu Gln Phe Gly Asp Ile Leu Asn Leu Val Gly Arg Pro Ser Ala Ile
        340                 345                 350 gat gcc gtt gcc aat gtg ctg ggg aat gcg cag caa aaa ctg caa cag       1104
Asp Ala Val Ala Asn Val Leu Gly Asn Ala Gln Gln Lys Leu Gln Gln
    355                 360                 365 gtt cag atg ctg cca gtg ttt att ggc atc ggg ctt ggc gta ttg tta       1152
Val Gln Met Leu Pro Val Phe Ile Gly Ile Gly Leu Gly Val Leu Leu
370                 375                 380 ggt tct att ccc gtc ttt gtg cca gga ttc ccg gcc gcg ttg aaa ctg       1200
Gly Ser Ile Pro Val Phe Val Pro Gly Phe Pro Ala Ala Leu Lys Leu
385                 390                 395                 400 ggg ctg gcg ggc ggt ccg ctg att atg gcg ttg atc ctc ggg cgt atc       1248
Gly Leu Ala Gly Gly Pro Leu Ile Met Ala Leu Ile Leu Gly Arg Ile
            405                 410                 415 ggc agt atc ggc aag ctg tac tgg ttt atg ccg cca agt gcc aac ctc       1296
Gly Ser Ile Gly Lys Leu Tyr Trp Phe Met Pro Pro Ser Ala Asn Leu
        420                 425                 430 gcg ctg cgg gag ctg ggg atc gtg ctg ttc ctc tcg atc gtt ggt ctg       1344
Ala Leu Arg Glu Leu Gly Ile Val Leu Phe Leu Ser Ile Val Gly Leu
    435                 440                 445 aaa tct ggt ggg gat ttt gtg aat acc ctg gtc aat ggc gaa ggg cta       1392
Lys Ser Gly Gly Asp Phe Val Asn Thr Leu Val Asn Gly Glu Gly Leu
450                 455                 460 agc tgg att ggt tat ggt gcc ctg atc acc gcc gtt ccg ctg att act       1440
Ser Trp Ile Gly Tyr Gly Ala Leu Ile Thr Ala Val Pro Leu Ile Thr
```

```
                465                 470                 475                 480
gtt ggc att ctg gcg cgg atg tta gcc aaa atg aat tac ctg acc atg         1488
Val Gly Ile Leu Ala Arg Met Leu Ala Lys Met Asn Tyr Leu Thr Met
                    485                 490                 495 tgc ggg atg ctg gca ggt tcc atg acc gat cct ccg gcg ctg gcg ttt         1536
Cys Gly Met Leu Ala Gly Ser Met Thr Asp Pro Pro Ala Leu Ala Phe
            500                 505                 510 gct aat aat ctt cat cca acc agt ggt gcg gcg gcg ctc tct tac gcc         1584
Ala Asn Asn Leu His Pro Thr Ser Gly Ala Ala Ala Leu Ser Tyr Ala
        515                 520                 525 act gtc tat ccg tta gtg atg ttc ctg cgc att atc acc ccc caa tta         1632
Thr Val Tyr Pro Leu Val Met Phe Leu Arg Ile Ile Thr Pro Gln Leu
    530                 535                 540 ctg gcg gtg ctc ttc tgg agt atc ggt taa                                 1662
Leu Ala Val Leu Phe Trp Ser Ile Gly
545                 550

<210> SEQ ID NO 26
<211> LENGTH: 553
<212> TYPE: PRT
<213> ORGANISM: Shigella flexneri

<400> SEQUENCE: 26

Met Ser Asp Ile Ala Leu Thr Val Ser Ile Leu Ala Leu Val Ala Val
1               5                   10                  15

Val Gly Leu Phe Ile Gly Asn Val Lys Phe Arg Gly Ile Gly Leu Gly
                20                  25                  30

Ile Gly Gly Val Leu Phe Gly Gly Ile Ile Val Gly His Phe Val Ser
            35                  40                  45

Gln Ala Gly Met Thr Leu Ser Ser Asp Met Leu His Val Ile Gln Glu
        50                  55                  60

Phe Gly Leu Ile Leu Phe Val Tyr Thr Ile Gly Ile Gln Val Gly Pro
65                  70                  75                  80

Gly Phe Phe Ala Ser Leu Arg Val Ser Gly Leu Arg Leu Asn Leu Phe
                85                  90                  95

Ala Val Leu Ile Val Ile Gly Gly Leu Val Thr Ala Ile Leu His
            100                 105                 110

Lys Leu Phe Asp Ile Pro Leu Pro Val Val Leu Gly Ile Phe Ser Gly
        115                 120                 125

Ala Val Thr Asn Thr Pro Ala Leu Gly Ala Gly Gln Gln Ile Leu Arg
    130                 135                 140

Asp Leu Gly Thr Pro Met Glu Met Val Asp Gln Met Gly Met Ser Tyr
145                 150                 155                 160

Ala Met Ala Tyr Pro Phe Gly Ile Cys Gly Ile Leu Phe Thr Met Trp
                165                 170                 175

Met Leu Arg Val Ile Phe Arg Val Asn Val Glu Thr Glu Ala Gln Gln
            180                 185                 190

His Glu Ser Ser Arg Thr Asn Ala Gly Ala Leu Ile Lys Thr Ile Asn
        195                 200                 205

Ile Arg Val Glu Asn Pro Asn Arg His Asp Leu Ala Ile Lys Asp Val
    210                 215                 220

Pro Ile Leu Asn Gly Asp Lys Ile Ile Cys Ser Arg Leu Lys Arg Glu
225                 230                 235                 240

Glu Thr Leu Lys Val Pro Ser Pro Asp Thr Ile Ile Gln Leu Gly Asp
                245                 250                 255

Leu Leu His Leu Val Gly Gln Pro Ala Asp Leu His Asn Ala Gln Leu
            260                 265                 270
```

-continued

```
Val Ile Gly Gln Glu Val Asp Thr Ser Leu Ser Thr Lys Gly Thr Asp
            275                 280                 285

Leu Arg Val Glu Arg Val Val Thr Asn Glu Asn Val Leu Gly Lys
    290                 295                 300

Arg Ile Arg Asp Leu His Phe Lys Glu Arg Tyr Asp Val Val Ile Ser
305                 310                 315                 320

Arg Leu Asn Arg Ala Gly Val Glu Leu Ala Ser Gly Asp Ile Ser
                325                 330                 335

Leu Gln Phe Gly Asp Ile Leu Asn Leu Val Gly Arg Pro Ser Ala Ile
            340                 345                 350

Asp Ala Val Ala Asn Val Leu Gly Asn Ala Gln Gln Lys Leu Gln Gln
                355                 360                 365

Val Gln Met Leu Pro Val Phe Ile Gly Ile Gly Leu Gly Val Leu Leu
            370                 375                 380

Gly Ser Ile Pro Val Phe Val Pro Gly Phe Pro Ala Ala Leu Lys Leu
385                 390                 395                 400

Gly Leu Ala Gly Gly Pro Leu Ile Met Ala Leu Ile Leu Gly Arg Ile
                405                 410                 415

Gly Ser Ile Gly Lys Leu Tyr Trp Phe Met Pro Pro Ser Ala Asn Leu
            420                 425                 430

Ala Leu Arg Glu Leu Gly Ile Val Leu Phe Leu Ser Ile Val Gly Leu
                435                 440                 445

Lys Ser Gly Gly Asp Phe Val Asn Thr Leu Val Asn Gly Glu Gly Leu
450                 455                 460

Ser Trp Ile Gly Tyr Gly Ala Leu Ile Thr Ala Val Pro Leu Ile Thr
465                 470                 475                 480

Val Gly Ile Leu Ala Arg Met Leu Ala Lys Met Asn Tyr Leu Thr Met
                485                 490                 495

Cys Gly Met Leu Ala Gly Ser Met Thr Asp Pro Pro Ala Leu Ala Phe
            500                 505                 510

Ala Asn Asn Leu His Pro Thr Ser Gly Ala Ala Ala Leu Ser Tyr Ala
                515                 520                 525

Thr Val Tyr Pro Leu Val Met Phe Leu Arg Ile Ile Thr Pro Gln Leu
            530                 535                 540

Leu Ala Val Leu Phe Trp Ser Ile Gly
545                 550

<210> SEQ ID NO 27
<211> LENGTH: 1659
<212> TYPE: DNA
<213> ORGANISM: Yersinia pestis
<220> FEATURE:
<221> N

```
              50                  55                  60
ttc ggc ctg att ctg ttt gtg tat acc atc ggt att caa gtt ggg ccg    240
Phe Gly Leu Ile Leu Phe Val Tyr Thr Ile Gly Ile Gln Val Gly Pro
 65                  70                  75                  80 ggg ttc ttc tct tca cta cgg gta tcg ggg ttg cgg ctt aac tgc ttc    288
Gly Phe Phe Ser Ser Leu Arg Val Ser Gly Leu Arg Leu Asn Cys Phe
                 85                  90                  95 gcc atc ttg atg gtg gtt gtg ggc ggg tta gta aca gcg att att cat    336
Ala Ile Leu Met Val Val Val Gly Gly Leu Val Thr Ala Ile Ile His
            100                 105                 110 aag ctg ttt gct gtg ccg ctg ccg att att ctg ggg gtg ttt tct ggt    384
Lys Leu Phe Ala Val Pro Leu Pro Ile Ile Leu Gly Val Phe Ser Gly
        115                 120                 125 gcg gta acc aat aca ccg gca ctt ggt gcg gct cag caa att ctt acc    432
Ala Val Thr Asn Thr Pro Ala Leu Gly Ala Ala Gln Gln Ile Leu Thr
130                 135                 140 gat tta ggt tcg ccg cca caa ctg gtc agt caa atg ggg atg ggt tac    480
Asp Leu Gly Ser Pro Pro Gln Leu Val Ser Gln Met Gly Met Gly Tyr
145                 150                 155                 160 gcc atg gcg tat cca ttt ggt att tgt ggc att tta ctg gtg atg tgg    528
Ala Met Ala Tyr Pro Phe Gly Ile Cys Gly Ile Leu Leu Val Met Trp
                165                 170                 175 ctg att cgt tta ttc ttt aaa atc aat atc gat cgt gaa gcg aaa gcg    576
Leu Ile Arg Leu Phe Phe Lys Ile Asn Ile Asp Arg Glu Ala Lys Ala
            180                 185                 190 ttc gac agc agc tac ggg caa aac cgc gag ttg ctg caa acc atg aac    624
Phe Asp Ser Ser Tyr Gly Gln Asn Arg Glu Leu Leu Gln Thr Met Asn
        195                 200                 205 gtt gcg gtg cgt aac ccc aat cta cat ggt tta tcg gta cag gat gtg    672
Val Ala Val Arg Asn Pro Asn Leu His Gly Leu Ser Val Gln Asp Val
210                 215                 220 cca ttg ctg aac agc gat gag gtg gtc tgt tca cga ttg aag cgt ggc    720
Pro Leu Leu Asn Ser Asp Glu Val Val Cys Ser Arg Leu Lys Arg Gly
225                 230                 235                 240 gat tta ctg atg gtg ccc atg cca gcc acg gtg att gaa att ggg gat    768
Asp Leu Leu Met Val Pro Met Pro Ala Thr Val Ile Glu Ile Gly Asp
                245                 250                 255 tat ctg cat ttg gtc ggg caa cgg gat gcg ctg gag aaa gtg cgg ctg    816
Tyr Leu His Leu Val Gly Gln Arg Asp Ala Leu Glu Lys Val Arg Leu
            260                 265                 270 gtt gtg ggt gaa gag gtc gat gtg aca tta tcc acg gca gga acg gcg    864
Val Val Gly Glu Glu Val Asp Val Thr Leu Ser Thr Ala Gly Thr Ala
        275                 280                 285 ttg caa acg gct cga gtg gta gtg acc aac gag gcg gta ctg ggt aaa    912
Leu Gln Thr Ala Arg Val Val Val Thr Asn Glu Ala Val Leu Gly Lys
290                 295                 300 aaa atc cgc gat ctt aat cta aaa cag aag tat gac gtg gtg att act    960
Lys Ile Arg Asp Leu Asn Leu Lys Gln Lys Tyr Asp Val Val Ile Thr
305                 310                 315                 320 cgt ctt aat cgc gcg ggt atc gag ctg gtc gcc agc aac agt gcc agc    1008
Arg Leu Asn Arg Ala Gly Ile Glu Leu Val Ala Ser Asn Ser Ala Ser
                325                 330                 335 ttg caa ttc ggc gat atc ctg aat tta gtg ggc cgt cct gaa gct atc    1056
Leu Gln Phe Gly Asp Ile Leu Asn Leu Val Gly Arg Pro Glu Ala Ile
            340                 345                 350 gaa gcg gtg tcc gcg att gtg ggg aac gcg cag caa aaa ttg caa cag    1104
Glu Ala Val Ser Ala Ile Val Gly Asn Ala Gln Gln Lys Leu Gln Gln
        355                 360                 365 gtg cag atg tta ccg gta ttt atc ggt gtc ggt ctc ggg gtt tta ctg    1152
Val Gln Met Leu Pro Val Phe Ile Gly Val Gly Leu Gly Val Leu Leu
```

```
                370                 375                 380
ggg tcg ata ccg ctg ttt gtt cca ggg ttt ccg gcg gca tta cgt tta    1200
Gly Ser Ile Pro Leu Phe Val Pro Gly Phe Pro Ala Ala Leu Arg Leu
385                 390                 395                 400 ggg cta gcg ggt ggt ccg cta gtg gtg gcg ttg atc ctc gga cgg att    1248
Gly Leu Ala Gly Gly Pro Leu Val Val Ala Leu Ile Leu Gly Arg Ile
            405                 410                 415 ggt agc att ggt aag ctg tat tgg ttt atg cca ccg agt gct aac ctg    1296
Gly Ser Ile Gly Lys Leu Tyr Trp Phe Met Pro Pro Ser Ala Asn Leu
        420                 425                 430 gcc ttg cgt gaa ttg ggg ata gtg ctg ttt ttg tca gtg gtc gga ttg    1344
Ala Leu Arg Glu Leu Gly Ile Val Leu Phe Leu Ser Val Val Gly Leu
    435                 440                 445 aaa tcc ggc ggt gat ttt atc aat acg ctg gtc aat ggt gat ggg ctg    1392
Lys Ser Gly Gly Asp Phe Ile Asn Thr Leu Val Asn Gly Asp Gly Leu
450                 455                 460 gca tgg att ggt tat ggt gcg atg atc acc ggg ata ccg ttg cta acg    1440
Ala Trp Ile Gly Tyr Gly Ala Met Ile Thr Gly Ile Pro Leu Leu Thr
465                 470                 475                 480 gta ggc att ttg gca cgt atg ctg gtc aaa atg aac tac ctg acg cta    1488
Val Gly Ile Leu Ala Arg Met Leu Val Lys Met Asn Tyr Leu Thr Leu
                485                 490                 495 tgt ggc atg tta gcg ggt tcg atg acg gat cca cct gcg ctg gcc ttt    1536
Cys Gly Met Leu Ala Gly Ser Met Thr Asp Pro Pro Ala Leu Ala Phe
            500                 505                 510 gcc aat ggc ctg cac ccg acc agc ggt gcg gcg gcg ttg tct tat gcg    1584
Ala Asn Gly Leu His Pro Thr Ser Gly Ala Ala Ala Leu Ser Tyr Ala
        515                 520                 525 aca gtg tac ccg ctg gcg atg ttt cta cga atc atg tca cca cag ata    1632
Thr Val Tyr Pro Leu Ala Met Phe Leu Arg Ile Met Ser Pro Gln Ile
    530                 535                 540 ttg gcg gta ttg ttc tgg acg ttg tag                                1659
Leu Ala Val Leu Phe Trp Thr Leu
545                 550

<210> SEQ ID NO 28
<211> LENGTH: 552
<212> TYPE: PRT
<213> ORGANISM: Yersinia pestis

<400> SEQUENCE: 28

Met Ser Ala Ile Ala Leu Thr Val Ser Met Leu Ala Leu Val Ala Val
1               5                   10                  15

Leu Gly Leu Trp Ile Gly Asn Trp Lys Ile Tyr Gly Val Gly Leu Gly
            20                  25                  30

Ile Gly Gly Val Leu Phe Gly Gly Ile Ile Val Gly His Phe Ala Gln
        35                  40                  45

Thr Tyr Gln Ile Val Leu Asn Gly Asp Met Leu His Phe Ile Gln Glu
    50                  55                  60

Phe Gly Leu Ile Leu Phe Val Tyr Thr Ile Gly Ile Gln Val Gly Pro
65                  70                  75                  80

Gly Phe Phe Ser Ser Leu Arg Val Ser Gly Leu Arg Leu Asn Cys Phe
                85                  90                  95

Ala Ile Leu Met Val Val Gly Gly Leu Val Thr Ala Ile Ile His
            100                 105                 110

Lys Leu Phe Ala Val Pro Leu Pro Ile Ile Leu Gly Val Phe Ser Gly
        115                 120                 125

Ala Val Thr Asn Thr Pro Ala Leu Gly Ala Ala Gln Gln Ile Leu Thr
    130                 135                 140
```

-continued

```
Asp Leu Gly Ser Pro Pro Gln Leu Val Ser Gln Met Gly Met Gly Tyr
145                 150                 155                 160

Ala Met Ala Tyr Pro Phe Gly Ile Cys Gly Ile Leu Leu Val Met Trp
                165                 170                 175

Leu Ile Arg Leu Phe Phe Lys Ile Asn Ile Asp Arg Glu Ala Lys Ala
            180                 185                 190

Phe Asp Ser Ser Tyr Gly Gln Asn Arg Glu Leu Leu Gln Thr Met Asn
        195                 200                 205

Val Ala Val Arg Asn Pro Asn Leu His Gly Leu Ser Val Gln Asp Val
    210                 215                 220

Pro Leu Leu Asn Ser Asp Glu Val Val Cys Ser Arg Leu Lys Arg Gly
225                 230                 235                 240

Asp Leu Leu Met Val Pro Met Pro Ala Thr Val Ile Glu Ile Gly Asp
                245                 250                 255

Tyr Leu His Leu Val Gly Gln Arg Asp Ala Leu Glu Lys Val Arg Leu
            260                 265                 270

Val Val Gly Glu Glu Val Asp Val Thr Leu Ser Thr Ala Gly Thr Ala
        275                 280                 285

Leu Gln Thr Ala Arg Val Val Thr Asn Glu Ala Val Leu Gly Lys
    290                 295                 300

Lys Ile Arg Asp Leu Asn Leu Lys Gln Lys Tyr Asp Val Val Ile Thr
305                 310                 315                 320

Arg Leu Asn Arg Ala Gly Ile Glu Leu Val Ala Ser Asn Ser Ala Ser
                325                 330                 335

Leu Gln Phe Gly Asp Ile Leu Asn Leu Val Gly Arg Pro Glu Ala Ile
            340                 345                 350

Glu Ala Val Ser Ala Ile Val Gly Asn Ala Gln Gln Lys Leu Gln Gln
        355                 360                 365

Val Gln Met Leu Pro Val Phe Ile Gly Val Gly Leu Gly Val Leu Leu
    370                 375                 380

Gly Ser Ile Pro Leu Phe Val Pro Gly Phe Pro Ala Ala Leu Arg Leu
385                 390                 395                 400

Gly Leu Ala Gly Gly Pro Leu Val Val Ala Leu Ile Leu Gly Arg Ile
                405                 410                 415

Gly Ser Ile Gly Lys Leu Tyr Trp Phe Met Pro Pro Ser Ala Asn Leu
            420                 425                 430

Ala Leu Arg Glu Leu Gly Ile Val Leu Phe Leu Ser Val Val Gly Leu
        435                 440                 445

Lys Ser Gly Gly Asp Phe Ile Asn Thr Leu Val Asn Gly Asp Gly Leu
    450                 455                 460

Ala Trp Ile Gly Tyr Gly Ala Met Ile Thr Gly Ile Pro Leu Leu Thr
465                 470                 475                 480

Val Gly Ile Leu Ala Arg Met Leu Val Lys Met Asn Tyr Leu Thr Leu
                485                 490                 495

Cys Gly Met Leu Ala Gly Ser Met Thr Asp Pro Pro Ala Leu Ala Phe
            500                 505                 510

Ala Asn Gly Leu His Pro Thr Ser Gly Ala Ala Ala Leu Ser Tyr Ala
        515                 520                 525

Thr Val Tyr Pro Leu Ala Met Phe Leu Arg Ile Met Ser Pro Gln Ile
    530                 535                 540

Leu Ala Val Leu Phe Trp Thr Leu
545                 550
```

```
<210> SEQ ID NO 29
<211> LENGTH: 553
<212> TYPE: PRT
<213> ORGANISM: Artificial Sequence
<220> FEATURE:
<223> OTHER INFORMATION: concerved sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (47)..(53)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (102)..(103)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
```

```
<222> LOCATION: (116)..(117)
<223> OTHER INFORMATION: Xaa can be any naturally occurring amino acid
<220> FEATURE:
<221> NAME/KEY: misc_feature
<222> LOCATION: (121)..(122)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (150)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (173)..(174)
<223> OTHER INFORMATION: Xaa can be any naturally occurring amino acid
<220> FEATURE:
<221> NAME/KEY: misc_feature
<222> LOCATION: (177)..(178)
<223> OTHER INFORMATION: Xaa can be any naturally occurring amino acid
<220> FEATURE:
<221> NAME/KEY: misc_feature
<222> LOCATION: (180)..(181)
<223> OTHER INFORMATION: Xaa can be any naturally occurring amino acid
<220> FEATURE:
<221> NAME/KEY: misc_feature
<222> LOCATION: (183)..(184)
<223> OTHER INFORMATION: Xaa can be any naturally occurring amino acid
<220> FEATURE:
<221> NAME/KEY: misc_feature
<222> LOCATION: (186)..(188)
<223> OTHER INFORMATION: Xaa can be any naturally occurring amino acid
<220> FEATURE:
<221> NAME/KEY: misc_feature
<222> LOCATION: (191)..(194)
<223> OTHER INFORMATION: Xaa can be any naturally occurring amino acid
<220> FEATURE:
<221> NAME/KEY: misc_feature
<222> LOCATION: (197)..(202)
<223> OTHER INFORMATION: Xaa can be any naturally occurring amino acid
<220> FEATURE:
<221> NAME/KEY: misc_feature
<222> LOCATION: (204)..(205)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (209)..(210)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
```

```
<222> LOCATION: (216)..(222)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (231)..(233)
<223> OTHER INFORMATION: Xaa can be any naturally occurring amino acid
<220> FEATURE:
<221> NAME/KEY: misc_feature
<222> LOCATION: (240)..(242)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (253)..(254)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (264)..(266)
<223> OTHER INFORMATION: Xaa can be any naturally occurring amino acid
<220> FEATURE:
<221> NAME/KEY: misc_feature
<222> LOCATION: (268)..(271)
<223> OTHER INFORMATION: Xaa can be any naturally occurring amino acid
<220> FEATURE:
<221> NAME/KEY: misc_feature
<222> LOCATION: (274)..(274)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: misc_feature
<222> LOCATION: (280)..(281)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (290)..(292)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: misc_feature
```

```
<222> LOCATION: (305)..(305)
<223> OTHER INFORMATION: Xaa can be any naturally occurring amino acid
<220> FEATURE:
<221> NAME/KEY: misc_feature
<222> LOCATION: (310)..(311)
<223> OTHER INFORMATION: Xaa can be any naturally occurring amino acid
<220> FEATURE:
<221> NAME/KEY: misc_feature
<222> LOCATION: (313)..(314)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (327)..(327)
<223> OTHER INFORMATION: Xaa can be any naturally occurring amino acid
<220> FEATURE:
<221> NAME/KEY: misc_feature
<222> LOCATION: (333)..(335)
<223> OTHER INFORMATION: Xaa can be any naturally occurring amino acid
<220> FEATURE:
<221> NAME/KEY: misc_feature
<222> LOCATION: (350)..(351)
<223> OTHER INFORMATION: Xaa can be any naturally occurring amino acid
<220> FEATURE:
<221> NAME/KEY: misc_feature
<222> LOCATION: (353)..(353)
<223> OTHER INFORMATION: Xaa can be any naturally occurring amino acid
<220> FEATURE:
<221> NAME/KEY: misc_feature
<222> LOCATION: (356)..(359)
<223> OTHER INFORMATION: Xaa can be any naturally occurring amino acid
<220> FEATURE:
<221> NAME/KEY: misc_feature
<222> LOCATION: (378)..(378)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (399)..(399)
<223> OTHER INFORMATION: Xaa can be any naturally occurring amino acid
<220> FEATURE:
<221> NAME/KEY: misc_feature
<222> LOCATION: (408)..(409)
<223> OTHER INFORMATION: Xaa can be any naturally occurring amino acid
<220> FEATURE:
<221> NAME/KEY: misc_feature
<222> LOCATION: (444)..(445)
<223> OTHER INFORMATION: Xaa can be any naturally occurring amino acid
<220> FEATURE:
<221> NAME/KEY: misc_feature
<222> LOCATION: (455)..(456)
<223> OTHER INFORMATION: Xaa can be any naturally occurring amino acid
<220> FEATURE:
<221> NAME/KEY: misc_feature
<222> LOCATION: (459)..(460)
<223> OTHER INFORMATION: Xaa can be any naturally occurring amino acid
<220> FEATURE:
<221> NAME/KEY: misc_feature
<222> LOCATION: (462)..(462)
<223> OTHER INFORMATION: Xaa can be any naturally occurring amino acid
<220> FEATURE:
<221> NAME/KEY: misc_feature
<222> LOCATION: (465)..(465)
<223> OTHER INFORMATION: Xaa can be any naturally occurring amino acid
<220> FEATURE:
<221> NAME/KEY: misc_feature
<222> LOCATION: (471)..(472)
<223> OTHER INFORMATION: Xaa can be any naturally occurring amino acid
<220> FEATURE:
<221> NAME/KEY: misc_feature
```

```
<222> LOCATION: (475)..(476)
<223> OTHER INFORMATION: Xaa can be any naturally occurring amino acid
<220> FEATURE:
<221> NAME/KEY: misc_feature
<222> LOCATION: (479)..(479)
<223> OTHER INFORMATION: Xaa can be any naturally occurring amino acid
<220> FEATURE:
<221> NAME/KEY: misc_feature
<222> LOCATION: (483)..(483)
<223> OTHER INFORMATION: Xaa can be any naturally occurring amino acid
<220> FEATURE:
<221> NAME/KEY: misc_feature
<222> LOCATION: (487)..(489)
<223> OTHER INFORMATION: Xaa can be any naturally occurring amino acid
<220> FEATURE:
<221> NAME/KEY: misc_feature
<222> LOCATION: (496)..(496)
<223> OTHER INFORMATION: Xaa can be any naturally occurring amino acid
<220> FEATURE:
<221> NAME/KEY: misc_feature
<222> LOCATION: (515)..(515)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: misc_feature
<222> LOCATION: (540)..(541)
<223> OTHER INFORMATION: Xaa can be any naturally occurring amino acid
<220> FEATURE:
<221> NAME/KEY: misc_feature
<222> LOCATION: (544)..(544)
<223> OTHER INFORMATION: Xaa can be any naturally occurring amino acid
<220> FEATURE:
<221> NAME/KEY: misc_feature
<222> LOCATION: (548)..(548)
<223> OTHER INFORMATION: Xaa can be any naturally occurring amino acid
<220> FEATURE:
<221> NAME/KEY: misc_feature
<222> LOCATION: (551)..(552)
<223> OTHER INFORMATION: Xaa can be any naturally occurring amino acid

<400> SEQUENCE: 29

Met Ser Xaa Ile Ala Leu Thr Val Ser Xaa Leu Ala Leu Val Ala Val
1               5                   10                  15

Xaa Gly Leu Xaa Ile Gly Asn Xaa Lys Xaa Xaa Gly Xaa Gly Xaa Gly
            20                  25                  30

Ile Gly Gly Val Leu Phe Gly Gly Ile Ile Val Gly His Phe Xaa Xaa
        35                  40                  45

Xaa Xaa Xaa Xaa Xaa Leu Xaa Xaa Asp Met Leu His Xaa Ile Gln Glu
    50                  55                  60

Phe Gly Leu Ile Leu Phe Val Tyr Thr Ile Gly Ile Gln Val Gly Pro
65                  70                  75                  80

Gly Phe Phe Xaa Ser Leu Arg Val Ser Gly Leu Arg Leu Asn Xaa Phe
                85                  90                  95

Ala Xaa Leu Xaa Val Xaa Xaa Gly Gly Leu Val Thr Ala Ile Xaa His
            100                 105                 110

Lys Xaa Phe Xaa Xaa Pro Leu Pro Xaa Xaa Leu Gly Xaa Phe Ser Gly
        115                 120                 125

Ala Val Thr Asn Thr Pro Ala Leu Gly Ala Xaa Gln Gln Ile Leu Xaa
    130                 135                 140

Asp Leu Gly Xaa Pro Xaa Xaa Xaa Val Xaa Gln Met Gly Met Xaa Tyr
145                 150                 155                 160

Ala Met Ala Tyr Pro Phe Gly Ile Cys Gly Ile Leu Xaa Xaa Met Trp
```

```
              165                 170                 175
Xaa Xaa Arg Xaa Phe Xaa Xaa Asn Xaa Xaa Xaa Glu Ala Xaa Xaa
            180                 185                 190
Xaa Xaa Ser Ser Xaa Xaa Xaa Xaa Xaa Leu Xaa Xaa Thr Xaa Asn
            195                 200                 205
Xaa Xaa Val Xaa Asn Pro Asn Xaa Xaa Xaa Xaa Xaa Xaa Asp Val
            210                 215                 220
Pro Xaa Leu Asn Xaa Asp Xaa Xaa Xaa Cys Ser Arg Leu Lys Arg Xaa
225             230                 235                 240
Xaa Xaa Leu Xaa Val Pro Xaa Pro Xaa Thr Xaa Ile Xaa Xaa Gly Asp
            245                 250                 255
Xaa Leu His Leu Val Gly Gln Xaa Xaa Xaa Leu Xaa Xaa Xaa Xaa Leu
            260                 265                 270
Val Xaa Gly Xaa Glu Val Asp Xaa Xaa Leu Ser Thr Xaa Gly Thr Xaa
            275                 280                 285
Leu Xaa Xaa Xaa Arg Val Val Val Thr Asn Glu Xaa Val Leu Gly Lys
            290                 295                 300
Xaa Ile Arg Asp Leu Xaa Xaa Lys Xaa Xaa Tyr Asp Val Val Ile Xaa
305             310                 315                 320
Arg Leu Asn Arg Ala Gly Xaa Glu Leu Val Ala Ser Xaa Xaa Xaa Ser
            325                 330                 335
Leu Gln Phe Gly Asp Ile Leu Asn Leu Val Gly Arg Pro Xaa Xaa Ile
            340                 345                 350
Xaa Ala Val Xaa Xaa Xaa Xaa Gly Asn Ala Gln Gln Lys Leu Gln Gln
            355                 360                 365
Val Gln Met Leu Pro Val Phe Ile Gly Xaa Gly Leu Gly Val Leu Leu
            370                 375                 380
Gly Ser Ile Pro Xaa Phe Val Pro Gly Phe Pro Xaa Ala Leu Xaa Leu
385             390                 395                 400
Gly Leu Ala Gly Gly Pro Leu Xaa Xaa Ala Leu Ile Leu Gly Arg Ile
            405                 410                 415
Gly Ser Ile Gly Lys Leu Tyr Trp Phe Met Pro Pro Ser Ala Asn Leu
            420                 425                 430
Ala Leu Arg Glu Leu Gly Ile Val Leu Phe Leu Xaa Xaa Val Gly Leu
            435                 440                 445
Lys Ser Gly Gly Asp Phe Xaa Xaa Thr Leu Xaa Xaa Gly Xaa Gly Leu
            450                 455                 460
Xaa Trp Ile Gly Tyr Gly Xaa Xaa Ile Thr Xaa Xaa Pro Leu Xaa Thr
465             470                 475                 480
Val Gly Xaa Leu Ala Arg Xaa Xaa Xaa Lys Met Asn Tyr Leu Thr Xaa
            485                 490                 495
Cys Gly Met Leu Ala Gly Ser Met Thr Asp Pro Pro Ala Leu Ala Phe
            500                 505                 510
Ala Asn Xaa Leu His Xaa Thr Ser Gly Ala Ala Ala Leu Ser Tyr Ala
            515                 520                 525
Thr Val Tyr Pro Leu Xaa Met Phe Leu Arg Ile Xaa Xaa Pro Gln Xaa
            530                 535                 540
Leu Ala Val Xaa Phe Trp Xaa Xaa Gly
545             550

<210> SEQ ID NO 30
<211> LENGTH: 843
<212> TYPE: DNA
<213> ORGANISM: Mannheimia succiniciproducens
<220> FEATURE:
```

```
<221> NAME/KEY: CDS
<222> LOCATION: (1)..(843)

<400> SEQUENCE: 30 ttg tcg gtg aaa aaa tcg aac ttg agc cgt cca aac tgg ttg gca ata      48
Leu Ser Val Lys Lys Ser Asn Leu Ser Arg Pro Asn Trp Leu Ala Ile
1               5                   10                  15 tcc cgt tcc gaa cgg gtt gtg ggt acc aat gaa aaa gta ttg ggt aaa      96
Ser Arg Ser Glu Arg Val Val Gly Thr Asn Glu Lys Val Leu Gly Lys
            20                  25                  30 cgc att cgt act ttg ggt att cat cag cgt tac ggc att atg att tcc     144
Arg Ile Arg Thr Leu Gly Ile His Gln Arg Tyr Gly Ile Met Ile Ser
        35                  40                  45 cgc tta aac cgt gcc ggg gtt gaa ctt gtg ccg act gcg gac agc att     192
Arg Leu Asn Arg Ala Gly Val Glu Leu Val Pro Thr Ala Asp Ser Ile
    50                  55                  60 ttg cag ttc ggg gac gtg ctt cac atg gtt ggt aat gtc gaa acc atg     240
Leu Gln Phe Gly Asp Val Leu His Met Val Gly Asn Val Glu Thr Met
65                  70                  75                  80 gat gcc gcc att tct att atc ggc aat gcc aaa cag aaa ttg caa cag     288
Asp Ala Ala Ile Ser Ile Ile Gly Asn Ala Lys Gln Lys Leu Gln Gln
                85                  90                  95 gtg caa atg cta ccg gtc ttt atc ggg att tgt tta ggg gtt tta tta     336
Val Gln Met Leu Pro Val Phe Ile Gly Ile Cys Leu Gly Val Leu Leu
            100                 105                 110 ggc tca tta ccg att cat ata ccg ggc ttc ccc gtt gcg ctt aaa tta     384
Gly Ser Leu Pro Ile His Ile Pro Gly Phe Pro Val Ala Leu Lys Leu
        115                 120                 125 ggt ctt gcg ggc ggt cct tta gtc gtt gcg tta atc ctt gcc cgt atc     432
Gly Leu Ala Gly Gly Pro Leu Val Val Ala Leu Ile Leu Ala Arg Ile
    130                 135                 140 ggt tca atc ggt aaa ctt tat tgg ttt atg ccg cca agt gcc aac tta     480
Gly Ser Ile Gly Lys Leu Tyr Trp Phe Met Pro Pro Ser Ala Asn Leu
145                 150                 155                 160 gcg tta cgt gaa atc ggt atc gta tta ttc ctt acg gtt gta ggc tta     528
Ala Leu Arg Glu Ile Gly Ile Val Leu Phe Leu Thr Val Val Gly Leu
                165                 170                 175 aaa tcc ggc ggt aat ttc gtc aat acc tta act caa ggt gat ggg gta     576
Lys Ser Gly Gly Asn Phe Val Asn Thr Leu Thr Gln Gly Asp Gly Val
            180                 185                 190 acc tgg atg gga tac ggc gtg ctg att aca ttt gtt ccg tta atg gct     624
Thr Trp Met Gly Tyr Gly Val Leu Ile Thr Phe Val Pro Leu Met Ala
        195                 200                 205 gtg ggc att atc gcc cgg atc tat gcg aag atg aat tat ctc agt atc     672
Val Gly Ile Ile Ala Arg Ile Tyr Ala Lys Met Asn Tyr Leu Ser Ile
    210                 215                 220 tgc ggt tta ctc gca ggt tcc atg acc gat ccg ccg gca tta gcc ttt     720
Cys Gly Leu Leu Ala Gly Ser Met Thr Asp Pro Pro Ala Leu Ala Phe
225                 230                 235                 240 gcc aat gcg att aaa gaa gaa aac ggt gcc gcc gct tta tct tat gcc     768
Ala Asn Ala Ile Lys Glu Glu Asn Gly Ala Ala Ala Leu Ser Tyr Ala
                245                 250                 255 acc gtg tat ccg ctg gtg atg ttc ctg cga ata att tct cct cag ttg     816
Thr Val Tyr Pro Leu Val Met Phe Leu Arg Ile Ile Ser Pro Gln Leu
            260                 265                 270 tta gca atc ctg ttg tgg gtt gca taa                                 843
Leu Ala Ile Leu Leu Trp Val Ala
        275                 280

<210> SEQ ID NO 31
<211> LENGTH: 280
```

<212> TYPE: PRT
<213> ORGANISM: Mannheimia succiniciproducens

<400> SEQUENCE: 31

Leu Ser Val Lys Lys Ser Asn Leu Ser Arg Pro Asn Trp Leu Ala Ile
1               5                   10                  15

Ser Arg Ser Glu Arg Val Val Gly Thr Asn Glu Lys Val Leu Gly Lys
            20                  25                  30

Arg Ile Arg Thr Leu Gly Ile His Gln Arg Tyr Gly Ile Met Ile Ser
        35                  40                  45

Arg Leu Asn Arg Ala Gly Val Glu Leu Val Pro Thr Ala Asp Ser Ile
    50                  55                  60

Leu Gln Phe Gly Asp Val Leu His Met Val Gly Asn Val Glu Thr Met
65                  70                  75                  80

Asp Ala Ala Ile Ser Ile Ile Gly Asn Ala Lys Gln Lys Leu Gln Gln
                85                  90                  95

Val Gln Met Leu Pro Val Phe Ile Gly Ile Cys Leu Gly Val Leu Leu
            100                 105                 110

Gly Ser Leu Pro Ile His Ile Pro Gly Phe Pro Val Ala Leu Lys Leu
        115                 120                 125

Gly Leu Ala Gly Gly Pro Leu Val Val Ala Leu Ile Leu Ala Arg Ile
    130                 135                 140

Gly Ser Ile Gly Lys Leu Tyr Trp Phe Met Pro Ser Ala Asn Leu
145                 150                 155                 160

Ala Leu Arg Glu Ile Gly Ile Val Leu Phe Leu Thr Val Val Gly Leu
                165                 170                 175

Lys Ser Gly Gly Asn Phe Val Asn Thr Leu Thr Gln Gly Asp Gly Val
            180                 185                 190

Thr Trp Met Gly Tyr Gly Val Leu Ile Thr Phe Val Pro Leu Met Ala
        195                 200                 205

Val Gly Ile Ile Ala Arg Ile Tyr Ala Lys Met Asn Tyr Leu Ser Ile
    210                 215                 220

Cys Gly Leu Leu Ala Gly Ser Met Thr Asp Pro Pro Ala Leu Ala Phe
225                 230                 235                 240

Ala Asn Ala Ile Lys Glu Glu Asn Gly Ala Ala Ala Leu Ser Tyr Ala
                245                 250                 255

Thr Val Tyr Pro Leu Val Met Phe Leu Arg Ile Ile Ser Pro Gln Leu
            260                 265                 270

Leu Ala Ile Leu Leu Trp Val Ala
        275                 280

<210> SEQ ID NO 32
<211> LENGTH: 89
<212> TYPE: DNA
<213> ORGANISM: Artificial Sequence
<220> FEATURE:
<223> OTHER INFORMATION: primer for deleting adhE

<400> SEQUENCE: 32
caagttgata agatcttccg tgccgccgct ctggccgctg cagatgctcg aatccctctc    60
tgaagcctgc ttttttatac taagttggc                                      89

<210> SEQ ID NO 33
<211> LENGTH: 89
<212> TYPE: DNA
<213> ORGANISM: Artificial Sequence
<220> FEATURE:
<223> OTHER INFORMATION: primer for deleting adhE

<400> SEQUENCE: 33

```
acgtgagcca ggaaatcagc ttcctgaacg ccggcttcgc gaatagattt cggaataccc    60
gctcaagtta gtataaaaaa gctgaacga                                      89
```

<210> SEQ ID NO 34
<211> LENGTH: 2688
<212> TYPE: DNA
<213> ORGANISM: Enterobacter aerogenes
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (1303)..(1303)
<223> OTHER INFORMATION: n is a, c, g, or t
<220> FEATURE:
<221> NAME/KEY: misc_feature
<222> LOCATION: (1869)..(1869)
<223> OTHER INFORMATION: n is a, c, g, or t
<220> FEATURE:
<221> NAME/KEY: misc_feature
<222> LOCATION: (2609)..(2610)
<223> OTHER INFORMATION: n is a, c, g, or t
<220> FEATURE:
<221> NAME/KEY: misc_feature
<222> LOCATION: (2618)..(2618)
<223> OTHER INFORMATION: n is a, c, g, or t

<400> SEQUENCE: 34

```
tcgcatgctc ccggccgcca tggccgcggg attctcgttg agcgtgtaaa aaaagcccag    60
cattgaatat gccagtttca ctcaagaaca agttgataag atcttccgtg ccgccgctct   120
ggccgctgca gatgctcgaa tccctctcgc taaaatggct gttgccgaat ccggcatggg   180
tattattgaa gataaagtga tcaaaaacca cttcgcttcc gaatatatct acaacgccta   240
taaagatgaa aagacctgtg cgtcctgtc tgaagacgac actttcggta ccatcaccat   300
tgctgagcca atcggtatta tttgcggtat cgtcccgact accaacccga cttctactgc   360
tatcttcaaa tcgctgatca gcctgaagac gcgtaacgcc atcatcttct ctccgcaccc   420
gcgtgctgct aaagacgcga ctaacaaagc ggcggacatc gtattgcagg cagctattgc   480
cgcaggcgcg ccgaaagatc tgatcggttg atcgaccag ccttccgtag aactgtctaa   540
cgcactgatg catcatcctg acatcaacct gatcctcgcc accggcggcc caggtatggt   600
taaggccgct tatagctccg gtaaaccagc tatcggcgtt ggcgcgggca acacgccggt   660
tgntattgat gaaacggctg atatcaaacg cgctgtggcg tccgtactga tgtcaaaaac   720
cttcgataac ggcgttatct gtgcttctga acaatccgtg gtggttgtcg actccgtcta   780
cgacgccgtc cgcgagcgtt ttgccagcca tggcggctac ctgctgcagg gtaaagagct   840
gaaagccgtt caggacatca tcctgaaaaa tggcgcgctg aatgcggcga tcgttggtca   900
accagcggca aaaatcgctg aactggcagg cttcaccgtg ccagccacca ctaagattct   960
gatcggcgaa gttaccgacg ttgacgaaag cgaaccgttc gctcacgaaa aactgtctcc  1020
gacgctggca atgtaccgtg cgaaagattt cgaagacgcg gtcaataaag cagaaaaact  1080
ggtcgccatg ggcggtatcg gtcacacctc ttgcctgtac accgaccagg acaaccagcc  1140
ggctcgcgtg gcctacttcg gccagatgat gaaaaccgcg cgtatcctga tcaacacccc  1200
ggcttcccag ggtggtatcg gcgacctgta aacttcaag ctcgcacctt ccctgactct  1260
gggttgtggt tcctggggtg gtaactccat ctctgaaaac gtnggtccga acacctgat  1320 caacaagaaa accgttgcta agcgagctga aaacatgttg tggcataaac ttccgaaatc  1380
```

```
tatctacttc cgtcgtggct cactgccaat cgcactggat gaagtgatta ctgatggtca    1440
caaacgcgcg ctgattgtga ctgaccgctt cctgttcaac aacggttacg cggaccagat    1500
cacttccgta ctgaaagcgg ctggcgtaga aaccgaagtg ttctttgaag ttgaagctga    1560
cccaacgctg actatcgtgc gtaaaggcgc ggatctggcc aactccttca aaccagacgt    1620
aatcatcgcc ctgggcggcg gttccccgat ggatgcggca aaaatcatgt gggtcatgta    1680
cgagcacccg gaaacccact cgaagaact  ggcgctgcgc tttatggata tccgtaaacg    1740
tatctacaag ttcccgaaaa tgggcgtcaa agccaagatg gttgccatta ccaccacctc    1800
cggtaccggt tctgaagtta ccccgttcgc cgtagtaacc gacgatgcaa ctggacagaa    1860
atatccgcng gctgactacg ctctgactcc ggatatggcg attgtcgatg ccaacctggt    1920
catggatatg ccgaagtctc tctgtgcctt cggtggtctg gatgccgtga ctcacgctct    1980
ggaagcttac gtctccgtac tggcttctga gttctccgat ggtcaggctc tgcaggcgct    2040
gaaactgcta aaagagtatc tgccggcctc ttaccatgaa ggttctaaga acccggtagc    2100
ccgcgaacgt gtgcacagcg ccgccactat cgccggtatc gcgtttgcta acgccttcct    2160
cggcgtgtgc cactcaatgg cgcacaaact gggctcgcag ttccacattc ctcacggtct    2220
ggcaaacgcc ctgctgatca gcaacgttat ccgctataac gcgaatgaca acccgaccaa    2280
gcagaccgca ttcagccagt atgaccgtcc gcaggcgcgc cgtcgctacg ctgagatcgc    2340
agaccacctg ggcctgagcg ctccgggcga ccgcactgcg gcgaaaatcg agaaactgct    2400
ggcatggctg aaaagcctca agctgaact  gggtattccg aaatctatcc gtgaagctgg    2460
cgttcaggaa gcagacttcc tggcgaacgt ggataaactg tctgaagatg cattcgatga    2520
ccagtgcacc ggcgctaacc cgcgttaccc gctgatctcc gagctgaaac agattctgct    2580
ggatacctac tacggtcgtg atttatgtnn agaaggtnga aactgcagcg aagaaagaag    2640
ctgctccggc taaagctgag aaaaaagcga aaaatccgc  ttaatcag               2688
```

<210> SEQ ID NO 35  
<211> LENGTH: 30  
<212> TYPE: DNA  
<213> ORGANISM: Artificial Sequence  
<220> FEATURE:  
<223> OTHER INFORMATION: primer for amplifying threonine promoter

<400> SEQUENCE: 35

```
aagagctccg cgaacgagcc atgacattgc                                       30
```

<210> SEQ ID NO 36  
<211> LENGTH: 43  
<212> TYPE: DNA  
<213> ORGANISM: Artificial Sequence  
<220> FEATURE:  
<223> OTHER INFORMATION: primer for amplifying threonine promoter

<400> SEQUENCE: 36

```
gtcgacacac gtcattcctc cttgtcgcct atattggtta aag                       43
```

<210> SEQ ID NO 37  
<211> LENGTH: 361  
<212> TYPE: DNA  
<213> ORGANISM: Escherichia coli

<400> SEQUENCE: 37

```
aagagctccg cgaacgagcc atgacattgc tgacgactct ggcagtggca gatgacataa    60
aactggtcga ctggttacaa caacgcctgg ggcttttaga gcaacgagac acggcaatgt   120
```

```
tgcaccgttt gctgcatgat attgaaaaaa atatcaccaa ataaaaaacg ccttagtaag      180
tatttttcag cttttcattc tgactgcaac gggcaatatg tctctgtgtg gattaaaaaa      240
agagtgtctg atagcagctt ctgaactggt tacctgccgt gagtaaatta aaattttatt      300
gacttaggtc actaaatact ttaaccaata taggcgacaa ggaggaatga cgtgtgtcga      360
c                                                                      361

<210> SEQ ID NO 38
<211> LENGTH: 44
<212> TYPE: DNA
<213> ORGANISM: Artificial Sequence
<220> FEATURE:
<223> OTHER INFORMATION: primer for amplifying pyruvate carboxylase gene

<400> SEQUENCE: 38
aaggaggaat gacgtgtgtc gactcacaca tcttcaacgc ttcc                        44

<210> SEQ ID NO 39
<211> LENGTH: 28
<212> TYPE: DNA
<213> ORGANISM: Artificial Sequence
<220> FEATURE:
<223> OTHER INFORMATION: primer for amplifying pyruvate carboxylase gene

<400> SEQUENCE: 39
ttgagctctt tttacagaaa ggtttagg                                          28

<210> SEQ ID NO 40
<211> LENGTH: 3461
<212> TYPE: DNA
<213> ORGANISM: Enterobacter aerogenes

<400> SEQUENCE: 40
aaggaggaat gacgtgtgtc gactcacaca tcttcaacgc ttccagcatt caaaaagatc      60
ttggtagcaa accgcggcga atcgcggtc cgtgctttcc gtgcagcact cgaaaccggt     120
gcagccacgg tagctatta cccccgtgaa gatcggggat cattccaccg ctcttttgct     180
tctgaagctg tccgcattgg taccgaaggc tcaccagtca aggcgtacct ggacatcgat     240
gaaattatcg gtcagctaa aaagttaaa gcagatgcca tttacccggg atacggcttc      300
ctgtctgaaa tgcccagct tgcccgcgag tgtgcggaaa acggcattac ttttattggc      360 ccaacccag aggttcttga tctcaccggt gataagtctc gcgcggtaac cgccgcgaag      420
aaggctggtc tgccagtttt ggcggaatcc accccgagca aaacatcga tgagatcgtt      480 aaaagcgctg aaggccagac ttaccccatc tttgtgaagg cagttgccgg tggtggcgga      540
cgcggtatgc gttttgttgc ttcacctgat gagcttcgca attagcaac agaagcatct      600 cgtgaagctg aagcggcttt cggcgatggc gcggtatatg tcgaacgtgc tgtgattaac      660
cctcagcata ttgaagtgca gatccttggc gatcacactg gagaagttgt acacctttat      720
gaacgtgact gctcactgca gcgtcgtcac caaaaagttg tcgaaattgc gccagcacag      780
catttggatc agaactgcg tgatcgcatt tgtgcggatg cagtaaagtt ctgccgctcc      840
attggttacc agggcgcggg aaccgtggaa ttcttggtcg atgaaagggg caaccacgtc      900
ttcatcgaaa tgaacccacg tatccaggtt gagcacaccg tgactgaaga agtcaccgag      960
gtggacctgg tgaaggcgca gatgcgcttg gctgctggtg caaccttgaa ggaattgggt     1020
ctgacccaag ataagatcaa gacccacggt gcagcactgc agtgccgcat caccacggaa     1080
gatccaaaca acggcttccg cccagatacc ggaactatca ccgcgtaccg ctcaccaggc     1140
```

```
ggagctggcg ttcgtcttga cggtgcagct cagctcggtg gcgaaatcac cgcacacttt    1200
gactccatgc tggtgaaaat gacctgccgt ggttccgact ttgaaactgc tgttgctcgt    1260
gcacagcgcg cgttggctga gttcaccgtg tctggtgttg caaccaacat tggtttcttg    1320
cgtgcgttgc tgcgggaaga ggacttcact tccaagcgca tcgccaccgg attcattgcc    1380
gatcacccgc acctccttca ggctccacct gctgatgatg agcagggacg catcctggat    1440
tacttggcag atgtcaccgt gaacaagcct catggtgtgc gtccaaagga tgttgcagct    1500
cctatcgata agctgcctaa catcaaggat ctgccactgc cacgcggttc ccgtgaccgc    1560
ctgaagcagc ttgcccagc cgcgtttgct cgtgatctcc gtgagcagga cgcactggca    1620
gttactgata ccaccttccg cgatgcacac cagtctttgc ttgcgacccg agtccgctca    1680
ttcgcactga agcctgcggc agaggccgtc gcaaagctga ctcctgagct tttgtccgtg    1740
gaggcctggg gcggcgcgac ctacgatgtg gcgatgcgtt tcctcttga ggatccgtgg    1800 gacaggctcg acgagctgcg cgaggcgatg ccgaatgtaa acattcagat gctgcttcgc    1860
ggccgcaaca ccgtgggata cacccccgtac ccagactccg tctgccgcgc gtttgttaag    1920
gaagctgcca gctccggcgt ggacatcttc cgcatcttcg acgcgcttaa cgacgtctcc    1980
cagatgcgtc cagcaatcga cgcagtcctg gagaccaaca ccgcggtagc cgaggtggct    2040
atggcttatt ctggtgatct ctctgatcca aatgaaaagc tctacaccct ggattactac    2100
ctaaagatgg cagaggagat cgtcaagtct ggcgctcaca tcttggccat taaggatatg    2160
gctggtctgc ttcgcccagc tgcggtaacc aagctggtca ccgcactgcg ccgtgaattc    2220
gatctgccag tgcacgtgca cacccacgac actgcgggtg gccagctggc aacctacttt    2280
gctgcagctc aagctggtgc agatgctgtt gacggtgctt ccgcaccact gtctggcacc    2340
acctcccagc catccctgtc tgccattgtt gctgcattcg cgcacacccg tcgcgatacc    2400
ggtttgagcc tcgaggctgt ttctgacctc gagccgtact gggaagcagt gcgcggactg    2460
tacctgccat ttgagtctgg aaccccaggc ccaaccggtc gcgtctaccg ccacgaaatc    2520
ccaggcggac agttgtccaa cctgcgtgca caggccaccg cactgggcct tgcggatcgt    2580
ttcgaactca tcgaagacaa ctacgcagcc gttaatgaga tgctgggacg cccaaccaag    2640
gtcaccccat cctccaaggt tgttggcgac ctcgcactcc acctcgttgg tgcgggtgtg    2700
gatccagcag actttgctgc cgatccacaa aagtacgaca tcccagactc tgtcatcgcg    2760
ttcctgcgcg gcgagcttgg taaccctcca ggtggctggc cagagccact gcgcacccgc    2820
gcactggaag gccgctccga aggcaaggca cctctgacgg aagttcctga ggaagagcag    2880
gcgcacctcg acgctgatga ttccaaggaa cgtcgcaata gcctcaaccg cctgctgttc    2940
ccgaagccaa ccgaagagtt cctcgagcac cgtcgccgct tcggcaacac ctctgcgctg    3000
gatgatcgtg aattcttcta cggcctggtc gaaggccgcg agactttgat ccgcctgcca    3060
gatgtgcgca ccccactgct tgttcgcctg gatgcgatct ctgagccaga cgataagggt    3120
atgcgcaatg ttgtggccaa cgtcaacggc cagatccgcc caatgcgtgt gcgtgaccgc    3180
tccgttgagt ctgtcaccgc aaccgcagaa aaggcagatt cctccaacaa gggccatgtt    3240
gctgcaccat tcgctggtgt tgtcaccgtg actgttgctg aaggtgatga ggtcaaggct    3300
ggagatgcag tcgcaatcat cgaggctatg aagatggaag caacaatcac tgcttctgtt    3360
gacggcaaaa tcgatcgcgt tgtggttcct gctgcaacga aggtggaagg tggcgacttg    3420
atcgtcgtcg tttcctaaac cttctctgtaa aaagagctca a    3461
```

```
<210> SEQ ID NO 41
<211> LENGTH: 32
<212> TYPE: DNA
<213> ORGANISM: Artificial Sequence
<220> FEATURE:
<223> OTHER INFORMATION: primer for amplifying threonine promoter

<400> SEQUENCE: 41
aagcatgcta cgcgaacgag ccatgacatt gc                                32

<210> SEQ ID NO 42
<211> LENGTH: 38
<212> TYPE: DNA
<213> ORGANISM: Artificial Sequence
<220> FEATURE:
<223> OTHER INFORMATION: primer for amplifying threonine promoter

<400> SEQUENCE: 42
catacgtcat tcctccttgt cgcctatatt ggttaaag                          38

<210> SEQ ID NO 43
<211> LENGTH: 357
<212> TYPE: DNA
<213> ORGANISM: Escherichia coli

<400> SEQUENCE: 43
aagcatgctc gcgaacgagc catgacattg ctgacgactc tggcagtggc agatgacata    60
aaactggtcg actggttaca caacgcctg gggcttttag agcaacgaga cacggcaatg   120
ttgcaccgtt tgctgcatga tattgaaaaa aatatcacca ataaaaaac gccttagtaa   180 gtattttca gcttttcatt ctgactgcaa cgggcaatat gtctctgtgt ggattaaaaa    240
aagagtgtct gatagcagct tctgaactgg ttacctgccg tgagtaaatt aaaatttat   300 tgacttaggt cactaaatac tttaaccaat ataggcgaca aggaggaatg acgtatg      357

<210> SEQ ID NO 44
<211> LENGTH: 40
<212> TYPE: DNA
<213> ORGANISM: Artificial Sequence
<220> FEATURE:
<223> OTHER INFORMATION: primer for amplifying yidE

<400> SEQUENCE: 44
gacaaggagg aatgacgtat gagtgatata gcattgaccg                        40

<210> SEQ ID NO 45
<211> LENGTH: 27
<212> TYPE: DNA
<213> ORGANISM: Artificial Sequence
<220> FEATURE:
<223> OTHER INFORMATION: primer for amplifying yidE

<400> SEQUENCE: 45
gggaaggatc cagcgagtat caggtgg                                      27

<210> SEQ ID NO 46
<211> LENGTH: 1745
<212> TYPE: DNA
<213> ORGANISM: Enterobacter aerogenes
<220> FEATURE:
<221> NAME/KEY: CDS
<222> LOCATION: (19)..(1680)

<400> SEQUENCE: 46
gacaaggagg aatgacgt atg agt gat ata gca ttg acc gtc agc gtg ttg    51
                    Met Ser Asp Ile Ala Leu Thr Val Ser Val Leu
```

```
            1               5                   10
gcg ctg gtt gcg gtg gtg gga ttg tgg atc ggt aat gtc aaa atc cgc    99
Ala Leu Val Ala Val Val Gly Leu Trp Ile Gly Asn Val Lys Ile Arg
            15                  20                  25 ggc gtc ggt ttt ggc atc ggc ggc gtg ctg ttt ggc ggc att atc gtg   147
Gly Val Gly Phe Gly Ile Gly Gly Val Leu Phe Gly Gly Ile Ile Val
        30                  35                  40 ggc cac ttt gtg gat cag gca ggg att acg ctg agc agc ccg atg ctg   195
Gly His Phe Val Asp Gln Ala Gly Ile Thr Leu Ser Ser Pro Met Leu
    45                  50                  55 cat ttt atc cag gaa ttc ggc ctt att ctc ttc gtt tat acc atc ggt   243
His Phe Ile Gln Glu Phe Gly Leu Ile Leu Phe Val Tyr Thr Ile Gly
60                  65                  70                  75 att cag gtc ggg ccg ggc ttt ttt gcc tcg tta cgc gtc gcc gga ctt   291
Ile Gln Val Gly Pro Gly Phe Phe Ala Ser Leu Arg Val Ala Gly Leu
            80                  85                  90 aag ctc aat ctg ttc gcg atc ctt atc gtc gta ctt ggc ggg ctg gtg   339
Lys Leu Asn Leu Phe Ala Ile Leu Ile Val Val Leu Gly Gly Leu Val
            95                  100                 105 act gcg atc ctg cat aaa ctg ttc aat att ccg ctg ccg gtg gtg ctt   387
Thr Ala Ile Leu His Lys Leu Phe Asn Ile Pro Leu Pro Val Val Leu
        110                 115                 120 ggt atc ttc tcc ggt gcg gtc acc aat acc ccg gcg ctt ggc gcc gga   435
Gly Ile Phe Ser Gly Ala Val Thr Asn Thr Pro Ala Leu Gly Ala Gly
    125                 130                 135 cag caa atc ctg cgc gat ctt ggc ctg ccg ttt gat gtc gtc gat cag   483
Gln Gln Ile Leu Arg Asp Leu Gly Leu Pro Phe Asp Val Val Asp Gln
140                 145                 150                 155 atg ggg atg agt tac gcg atg gcc tac ccg ttt ggt atc tgc ggc att   531
Met Gly Met Ser Tyr Ala Met Ala Tyr Pro Phe Gly Ile Cys Gly Ile
            160                 165                 170 ttg ctg acc atg tgg ctg gtg cgg ctg ttc ttc cgc atc aat gtg gaa   579
Leu Leu Thr Met Trp Leu Val Arg Leu Phe Phe Arg Ile Asn Val Glu
            175                 180                 185 aaa gag gcg cag cag ttt gat gag agc agc ggt aac ggg cac gct cat   627
Lys Glu Ala Gln Gln Phe Asp Glu Ser Ser Gly Asn Gly His Ala His
            190                 195                 200 ctg cac acc att aac gtg cgg gtg gag aac ccg aac ctg aat aat atg   675
Leu His Thr Ile Asn Val Arg Val Glu Asn Pro Asn Leu Asn Asn Met
    205                 210                 215 gcg att cag gat gtg cca atg ctc aac agc gac aaa att atc tgc tcg   723
Ala Ile Gln Asp Val Pro Met Leu Asn Ser Asp Lys Ile Ile Cys Ser
220                 225                 230                 235 cgg ttg aag cgc gat gag cta ttg atg gtg ccg gcg ccg ggt acg ctt   771
Arg Leu Lys Arg Asp Glu Leu Leu Met Val Pro Ala Pro Gly Thr Leu
            240                 245                 250 atc cag cat ggc gat ctg ctg cac ctg gtc ggg cgg ccg gag gat tta   819
Ile Gln His Gly Asp Leu Leu His Leu Val Gly Arg Pro Glu Asp Leu
        255                 260                 265 cac aat gcg cag ctg gtg att ggt aaa gag gtg gcg act tcg ctc tca   867
His Asn Ala Gln Leu Val Ile Gly Lys Glu Val Ala Thr Ser Leu Ser
    270                 275                 280 acg cgc gga acc gat ctc aaa gtg gaa cgc gtg gtg gtc act aac gag   915
Thr Arg Gly Thr Asp Leu Lys Val Glu Arg Val Val Val Thr Asn Glu
285                 290                 295 aag gtc tta ggg aag aaa atc cgc gat ctg cac ttt aaa caa cgc tat   963
Lys Val Leu Gly Lys Lys Ile Arg Asp Leu His Phe Lys Gln Arg Tyr
300                 305                 310                 315 gac gtc gtg atc tcg cgg ctt aat cgc gcc ggg gtg gag ctg gtg gcc  1011
Asp Val Val Ile Ser Arg Leu Asn Arg Ala Gly Val Glu Leu Val Ala
```

```
                        320                 325                 330
agc agc cat gcc agc ctg cag ttt ggc gac att ctt aac tta gtt ggg        1059
Ser Ser His Ala Ser Leu Gln Phe Gly Asp Ile Leu Asn Leu Val Gly
            335                 340                 345 cgt cca cag gcc att gac gcg gtg gcc aat gaa ctc ggc aac gca cag        1107
Arg Pro Gln Ala Ile Asp Ala Val Ala Asn Glu Leu Gly Asn Ala Gln
        350                 355                 360 caa aaa ctg caa cag gta caa atg cta ccg gtg ttt atc ggc att ggc        1155
Gln Lys Leu Gln Gln Val Gln Met Leu Pro Val Phe Ile Gly Ile Gly
    365                 370                 375 ctg ggg gtg ctg ctg ggg tct att ccg ctg ttt att cct ggc ttc ccg        1203
Leu Gly Val Leu Leu Gly Ser Ile Pro Leu Phe Ile Pro Gly Phe Pro
380                 385                 390                 395 gca gcg tta aaa ctg ggg ctg gcc ggc ggg ccg ctg att atg gcg ctg        1251
Ala Ala Leu Lys Leu Gly Leu Ala Gly Gly Pro Leu Ile Met Ala Leu
                400                 405                 410 atc ctc ggg cgt atc ggc agc atc ggc aag ttg tac tgg ttt atg ccg        1299
Ile Leu Gly Arg Ile Gly Ser Ile Gly Lys Leu Tyr Trp Phe Met Pro
            415                 420                 425 ccg agc gcc aac ctg gcg ctg cgc gaa ctc ggt att gtg ctg ttt ctg        1347
Pro Ser Ala Asn Leu Ala Leu Arg Glu Leu Gly Ile Val Leu Phe Leu
        430                 435                 440 gcg gtg gtg ggg ctg aag tcc ggc ggc gat ttt gtc gac acc ctg ctc        1395
Ala Val Val Gly Leu Lys Ser Gly Gly Asp Phe Val Asp Thr Leu Leu
    445                 450                 455 cac ggc gag ggg ctc agc tgg atc gcc tac ggt att ttc atc acc gct        1443
His Gly Glu Gly Leu Ser Trp Ile Ala Tyr Gly Ile Phe Ile Thr Ala
460                 465                 470                 475 atc ccg ctg ctg acg gtg ggc ata ctg gcg cgg atg ctg gcg aag atg        1491
Ile Pro Leu Leu Thr Val Gly Ile Leu Ala Arg Met Leu Ala Lys Met
                480                 485                 490 aac tat ctg acc ctc tgc ggg atg ctg gcg ggc tca atg acc gac ccg        1539
Asn Tyr Leu Thr Leu Cys Gly Met Leu Ala Gly Ser Met Thr Asp Pro
            495                 500                 505 ccg gcg ctg gcc ttc gcc aac aac ctg cac gcc acc agc ggc gcg gcg        1587
Pro Ala Leu Ala Phe Ala Asn Asn Leu His Ala Thr Ser Gly Ala Ala
        510                 515                 520 gcg ctc tcc tac gcc acg gtt tat ccg ttg gtg atg ttc ctg cgg ata        1635
Ala Leu Ser Tyr Ala Thr Val Tyr Pro Leu Val Met Phe Leu Arg Ile
    525                 530                 535 atc acc cct cag cta ctg gcc gtg ctg ttc tgg ggg ctg agt tag           1680
Ile Thr Pro Gln Leu Leu Ala Val Leu Phe Trp Gly Leu Ser
540                 545                 550 cgggctctgt gcctggaccc ggcgcaggtg ataatccacc tgatactcgc tggcgttgga      1740
tcctt                                                                   1745

<210> SEQ ID NO 47
<211> LENGTH: 553
<212> TYPE: PRT
<213> ORGANISM: Enterobacter aerogenes

<400> SEQUENCE: 47

Met Ser Asp Ile Ala Leu Thr Val Ser Val Leu Ala Leu Val Ala Val
1               5                   10                  15

Val Gly Leu Trp Ile Gly Asn Val Lys Ile Arg Gly Val Gly Phe Gly
                20                  25                  30

Ile Gly Gly Val Leu Phe Gly Gly Ile Val Gly His Phe Val Asp
            35                  40                  45

Gln Ala Gly Ile Thr Leu Ser Ser Pro Met Leu His Phe Ile Gln Glu
```

```
                50                      55                      60
Phe Gly Leu Ile Leu Phe Val Tyr Thr Ile Gly Ile Gln Val Gly Pro
 65                      70                      75                      80

Gly Phe Phe Ala Ser Leu Arg Val Ala Gly Leu Lys Leu Asn Leu Phe
                         85                      90                      95

Ala Ile Leu Ile Val Leu Gly Gly Leu Val Thr Ala Ile Leu His
                        100                     105                     110

Lys Leu Phe Asn Ile Pro Leu Pro Val Val Leu Gly Ile Phe Ser Gly
                115                     120                     125

Ala Val Thr Asn Thr Pro Ala Leu Gly Ala Gln Gln Ile Leu Arg
130                     135                     140

Asp Leu Gly Leu Pro Phe Asp Val Val Asp Gln Met Gly Met Ser Tyr
145                     150                     155                     160

Ala Met Ala Tyr Pro Phe Gly Ile Cys Gly Ile Leu Leu Thr Met Trp
                165                     170                     175

Leu Val Arg Leu Phe Phe Arg Ile Asn Val Glu Lys Glu Ala Gln Gln
                180                     185                     190

Phe Asp Glu Ser Ser Gly Asn Gly His Ala His Leu His Thr Ile Asn
                195                     200                     205

Val Arg Val Glu Asn Pro Asn Leu Asn Asn Met Ala Ile Gln Asp Val
210                     215                     220

Pro Met Leu Asn Ser Asp Lys Ile Ile Cys Ser Arg Leu Lys Arg Asp
225                     230                     235                     240

Glu Leu Leu Met Val Pro Ala Pro Gly Thr Leu Ile Gln His Gly Asp
                245                     250                     255

Leu Leu His Leu Val Gly Arg Pro Glu Asp Leu His Asn Ala Gln Leu
                260                     265                     270

Val Ile Gly Lys Glu Val Ala Thr Ser Leu Ser Thr Arg Gly Thr Asp
                275                     280                     285

Leu Lys Val Glu Arg Val Val Thr Asn Glu Lys Val Leu Gly Lys
                290                     295                     300

Lys Ile Arg Asp Leu His Phe Lys Gln Arg Tyr Asp Val Val Ile Ser
305                     310                     315                     320

Arg Leu Asn Arg Ala Gly Val Glu Leu Val Ala Ser Ser His Ala Ser
                        325                     330                     335

Leu Gln Phe Gly Asp Ile Leu Asn Leu Val Gly Arg Pro Gln Ala Ile
                340                     345                     350

Asp Ala Val Ala Asn Glu Leu Gly Asn Ala Gln Gln Lys Leu Gln Gln
                355                     360                     365

Val Gln Met Leu Pro Val Phe Ile Gly Ile Gly Leu Gly Val Leu Leu
                370                     375                     380

Gly Ser Ile Pro Leu Phe Ile Pro Gly Phe Pro Ala Ala Leu Lys Leu
385                     390                     395                     400

Gly Leu Ala Gly Gly Pro Leu Ile Met Ala Leu Ile Leu Gly Arg Ile
                        405                     410                     415

Gly Ser Ile Gly Lys Leu Tyr Trp Phe Met Pro Pro Ser Ala Asn Leu
                420                     425                     430

Ala Leu Arg Glu Leu Gly Ile Val Leu Phe Leu Ala Val Val Gly Leu
                435                     440                     445

Lys Ser Gly Gly Asp Phe Val Asp Thr Leu Leu His Gly Glu Gly Leu
                450                     455                     460

Ser Trp Ile Ala Tyr Gly Ile Phe Ile Thr Ala Ile Pro Leu Leu Thr
465                     470                     475                     480
```

```
Val Gly Ile Leu Ala Arg Met Leu Ala Lys Met Asn Tyr Leu Thr Leu
            485                 490                 495

Cys Gly Met Leu Ala Gly Ser Met Thr Asp Pro Pro Ala Leu Ala Phe
        500                 505                 510

Ala Asn Asn Leu His Ala Thr Ser Gly Ala Ala Leu Ser Tyr Ala
        515                 520                 525

Thr Val Tyr Pro Leu Val Met Phe Leu Arg Ile Ile Thr Pro Gln Leu
    530                 535                 540

Leu Ala Val Leu Phe Trp Gly Leu Ser
545                 550

<210> SEQ ID NO 48
<211> LENGTH: 33
<212> TYPE: DNA
<213> ORGANISM: Artificial Sequence
<220> FEATURE:
<223> OTHER INFORMATION: primer for amplifying cat

<400> SEQUENCE: 48
tagcgagatc tctgatgtcc ggcggtgctt ttg                            33

<210> SEQ ID NO 49
<211> LENGTH: 32
<212> TYPE: DNA
<213> ORGANISM: Artificial Sequence
<220> FEATURE:
<223> OTHER INFORMATION: primer for amplifying cat

<400> SEQUENCE: 49
aaaaagagct cttacgcccc gccctgccac tc                             32

<210> SEQ ID NO 50
<211> LENGTH: 34
<212> TYPE: DNA
<213> ORGANISM: Artificial Sequence
<220> FEATURE:
<223> OTHER INFORMATION: primer for amplifying sacB

<400> SEQUENCE: 50
caggatctag aaggagacat gaacgatgaa catc                           34

<210> SEQ ID NO 51
<211> LENGTH: 36
<212> TYPE: DNA
<213> ORGANISM: Artificial Sequence
<220> FEATURE:
<223> OTHER INFORMATION: primer for amplifying sacB

<400> SEQUENCE: 51
gataaggatc cgaaataaaa gaaaatgcca atagga                         36

<210> SEQ ID NO 52
<211> LENGTH: 31
<212> TYPE: DNA
<213> ORGANISM: Artificial Sequence
<220> FEATURE:
<223> OTHER INFORMATION: primer for amplifying PlacUV5 fragment

<400> SEQUENCE: 52
cctttgagct cgcgggcagt gagcgcaacg c                              31

<210> SEQ ID NO 53
<211> LENGTH: 48
<212> TYPE: DNA
<213> ORGANISM: Artificial Sequence
```

```
<220> FEATURE:
<223> OTHER INFORMATION: primer for amplifying PlacUV5 fragment

<400> SEQUENCE: 53
ctagagcggc cgccgatcgg gatcctcctg tgtgaaattg ttatccgc                    48

<210> SEQ ID NO 54
<211> LENGTH: 42
<212> TYPE: DNA
<213> ORGANISM: Artificial Sequence
<220> FEATURE:
<223> OTHER INFORMATION: primer for amplifying DNA fragment containing
      lambda Red alpha, beta and gamma genes and tL3

<400> SEQUENCE: 54
ctctacgatc gaggaggtta taaaaaatgg atattaatac tg                         42

<210> SEQ ID NO 55
<211> LENGTH: 36
<212> TYPE: DNA
<213> ORGANISM: Artificial Sequence
<220> FEATURE:
<223> OTHER INFORMATION: primer for amplifying DNA fragment containing
      lambda Red alpha, beta and gamma genes and tL3

<400> SEQUENCE: 55
tcaaagcggc cgcttcttcg tctgtttcta ctggta                                36

<210> SEQ ID NO 56
<211> LENGTH: 31
<212> TYPE: DNA
<213> ORGANISM: Artificial Sequence
<220> FEATURE:
<223> OTHER INFORMATION: primer for amplifying DNA fragment containing
      PlacUV5 and TrrnB

<400> SEQUENCE: 56
cctttggtac cgcgggcagt gagcgcaacg c                                     31

<210> SEQ ID NO 57
<211> LENGTH: 34
<212> TYPE: DNA
<213> ORGANISM: Artificial Sequence
<220> FEATURE:
<223> OTHER INFORMATION: primer for amplifying DNA fragment containing
      PlacUV5 and TrrnB

<400> SEQUENCE: 57
aacaggaatt ctttgcctgg cggcagtagc gcgg                                  34

<210> SEQ ID NO 58
<211> LENGTH: 40
<212> TYPE: DNA
<213> ORGANISM: Artificial Sequence
<220> FEATURE:
<223> OTHER INFORMATION: primer for amplifying attL

<400> SEQUENCE: 58
ctagtaagat cttgaagcct gcttttttat actaagttgg                            40

<210> SEQ ID NO 59
<211> LENGTH: 41
<212> TYPE: DNA
<213> ORGANISM: Artificial Sequence
<220> FEATURE:
<223> OTHER INFORMATION: primer for amplifying attL

<400> SEQUENCE: 59
```

```
atgatcgaat tcgaaatcaa ataatgattt tattttgact g                          41
```

<210> SEQ ID NO 60
<211> LENGTH: 120
<212> TYPE: DNA
<213> ORGANISM: Escherichia coli

<400> SEQUENCE: 60

```
agatcttgaa gcctgctttt ttatactaag ttggcattat aaaaaagcat tgcttatcaa      60
tttgttgcaa cgaacaggtc actatcagtc aaaataaaat cattatttga tttcgaattc     120
```

<210> SEQ ID NO 61
<211> LENGTH: 41
<212> TYPE: DNA
<213> ORGANISM: Artificial Sequence
<220> FEATURE:
<223> OTHER INFORMATION: primer for amplifying attR

<400> SEQUENCE: 61

```
atgccactgc agtctgttac aggtcactaa taccatctaa g                          41
```

<210> SEQ ID NO 62
<211> LENGTH: 46
<212> TYPE: DNA
<213> ORGANISM: Artificial Sequence
<220> FEATURE:
<223> OTHER INFORMATION: primer for amplifying attR

<400> SEQUENCE: 62

```
accgttaagc tttctagacg ctcaagttag tataaaaaag ctgaac                     46
```

<210> SEQ ID NO 63
<211> LENGTH: 184
<212> TYPE: DNA
<213> ORGANISM: Escherichia coli

<400> SEQUENCE: 63

```
ctgcagtctg ttacaggtca ctaataccat ctaagtagtt gattcatagt gactgcatat      60
gttgtgtttt acagtattat gtagtctgtt ttttatgcaa aatctaattt aatatattga     120
tatttatatc attttacgtt tctcgttcag ctttttttata ctaacttgag cgtctagaaa    180
gctt                                                                 184
```

<210> SEQ ID NO 64
<211> LENGTH: 38
<212> TYPE: DNA
<213> ORGANISM: Artificial Sequence
<220> FEATURE:
<223> OTHER INFORMATION: primer for amplifying bla

<400> SEQUENCE: 64

```
ttcttagacg tcaggtggca cttttcgggg aaatgtgc                              38
```

<210> SEQ ID NO 65
<211> LENGTH: 37
<212> TYPE: DNA
<213> ORGANISM: Artificial Sequence
<220> FEATURE:
<223> OTHER INFORMATION: primer for amplifying bla

<400> SEQUENCE: 65

```
taacagagat ctcgcgcaga aaaaaaggat ctcaaga                               37
```

```
<210> SEQ ID NO 66
<211> LENGTH: 46
<212> TYPE: DNA
<213> ORGANISM: Artificial Sequence
<220> FEATURE:
<223> OTHER INFORMATION: primer for amplifying ter_rrnB

<400> SEQUENCE: 66
aacagagatc taagcttaga tcctttgcct ggcggcagta gcgcgg            46

<210> SEQ ID NO 67
<211> LENGTH: 35
<212> TYPE: DNA
<213> ORGANISM: Artificial Sequence
<220> FEATURE:
<223> OTHER INFORMATION: primer for amplifying ter_rrnB

<400> SEQUENCE: 67
ataaactgca gcaaaaagag tttgtagaaa cgcaa                        35

<210> SEQ ID NO 68
<211> LENGTH: 1388
<212> TYPE: DNA
<213> ORGANISM: Escherichia coli

<400> SEQUENCE: 68
gaattctcat gtttgacagc ttatcatcga taagctttaa tgcggtagtt tatcacagtt    60
aaattgctaa cgcagtcagg caccgtgtat gaaatctaac aatgcgctca tcgtcatcct   120
cggcaccgtc accctggatg ctgtaggcat aggcttggtt atgccggtac tgccgggcct   180
cttgcgggat atcgtccatt ccgacagcat cgccagtcac tatggcgtgc tgctagcgct   240
atatgcgttg atgcaatttc tatgcgcacc cgttctcgga gcactgtccg accgctttgg   300
ccgccgccca gtcctgctcg cttcgctact tggagccact atcgactacg cgatcatggc   360
gaccacaccc gtcctgtgga tcctctacgc cggacgcatc gtggccggca tcaccggcgc   420
cacaggtgcg gttgctggcg cctatatcgc cgacatcacc gatggggaag atcgggctcg   480
ccacttcggg ctcatgagcg cttgtttcgg cgtgggtatg gtggcaggcc ccgtggccgg   540
gggactgttg ggcgccatct ccttgcatgc accattcctt gcggcggcgg tgctcaacgg   600
cctcaaccta ctactgggct gcttcctaat gcaggagtcg cataagggag agcgtcgacc   660
gatgcccttg agagccttca acccagtcag ctccttccgg tgggcgcggg gcatgactat   720
cgtcgccgca cttatgactg tcttctttat catgcaactc gtaggacagg tgccggcagc   780
gctctgggtc attttcggcg aggaccgctt tcgctggagc gcgacgatga tcggcctgtc   840
gcttgcggta ttcggaatct tgcacgccct cgctcaagcc ttcgtcactg gtcccgccac   900
caaacgtttc ggcgagaagc aggccattat cgccggcatg gcggccgacg cgctgggcta   960
cgtcttgctg gcgttcgcga cgcgaggctg gatggccttc cccattatga ttcttctcgc  1020
ttccggcggc atcgggatgc cgcgttgca ggccatgctg tccaggcagg tagatgacga  1080
ccatcaggga cagcttcaag gatcgctcgc ggctcttacc agcctaactt cgatcactgg  1140
accgctgatc gtcacggcga tttatgccgc ctcggcgagc acatggaacg ggttggcatg  1200
gattgtaggc gccgccctat accttgtctg cctccccgcg ttgcgtcgcg gtgcatggag  1260
ccgggccacc tcgacctgaa tggaagccgg cggcacctcg ctaacggatt caccactcca  1320
actagaaagc ttaacacaga aaaaagcccg cacctgacag tgcgggcttt ttttttcgac  1380
cactgcag                                                           1388
```

```
<210> SEQ ID NO 69
<211> LENGTH: 36
<212> TYPE: DNA
<213> ORGANISM: Artificial Sequence
<220> FEATURE:
<223> OTHER INFORMATION: primer for amplifying ter_thrL

<400> SEQUENCE: 69
agtaattcta gaaagcttaa cacagaaaaa agcccg                                  36

<210> SEQ ID NO 70
<211> LENGTH: 43
<212> TYPE: DNA
<213> ORGANISM: Artificial Sequence
<220> FEATURE:
<223> OTHER INFORMATION: primer for amplifying ter_thrL

<400> SEQUENCE: 70
ctagtaggat ccctgcagtg gtcgaaaaaa aaagcccgca ctg                          43

<210> SEQ ID NO 71
<211> LENGTH: 553
<212> TYPE: PRT
<213> ORGANISM: Artificial Sequence
<220> FEATURE:
<223> OTHER INFORMATION: conserved sequnece
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
```

```
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(103)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (150)..(152)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (177)..(178)
<223> OTHER INFORMATION: Xaa can be any naturally occurring amino acid
<220> FEATURE:
<221> NAME/KEY: misc_feature
<222> LOCATION: (180)..(181)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (192)..(195)
<223> OTHER INFORMATION: Xaa can be any naturally occurring amino acid
<220> FEATURE:
<221> NAME/KEY: misc_feature
<222> LOCATION: (197)..(198)
<223> OTHER INFORMATION: Xaa can be any naturally occurring amino acid
<220> FEATURE:
<221> NAME/KEY: misc_feature
<222> LOCATION: (201)..(205)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (217)..(219)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
```

```
<222> LOCATION: (240)..(242)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (263)..(265)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: misc_feature
<222> LOCATION: (279)..(279)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (313)..(313)
<223> OTHER INFORMATION: Xaa can be any naturally occurring amino acid
<220> FEATURE:
<221> NAME/KEY: misc_feature
<222> LOCATION: (333)..(335)
<223> OTHER INFORMATION: Xaa can be any naturally occurring amino acid
<220> FEATURE:
<221> NAME/KEY: misc_feature
<222> LOCATION: (350)..(351)
<223> OTHER INFORMATION: Xaa can be any naturally occurring amino acid
<220> FEATURE:
<221> NAME/KEY: misc_feature
<222> LOCATION: (358)..(359)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (391)..(391)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
```

```
<222> LOCATION: (444)..(444)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (459)..(460)
<223> OTHER INFORMATION: Xaa can be any naturally occurring amino acid
<220> FEATURE:
<221> NAME/KEY: misc_feature
<222> LOCATION: (468)..(468)
<223> OTHER INFORMATION: Xaa can be any naturally occurring amino acid
<220> FEATURE:
<221> NAME/KEY: misc_feature
<222> LOCATION: (471)..(472)
<223> OTHER INFORMATION: Xaa can be any naturally occurring amino acid
<220> FEATURE:
<221> NAME/KEY: misc_feature
<222> LOCATION: (476)..(476)
<223> OTHER INFORMATION: Xaa can be any naturally occurring amino acid
<220> FEATURE:
<221> NAME/KEY: misc_feature
<222> LOCATION: (479)..(479)
<223> OTHER INFORMATION: Xaa can be any naturally occurring amino acid
<220> FEATURE:
<221> NAME/KEY: misc_feature
<222> LOCATION: (483)..(483)
<223> OTHER INFORMATION: Xaa can be any naturally occurring amino acid
<220> FEATURE:
<221> NAME/KEY: misc_feature
<222> LOCATION: (487)..(488)
<223> OTHER INFORMATION: Xaa can be any naturally occurring amino acid
<220> FEATURE:
<221> NAME/KEY: misc_feature
<222> LOCATION: (496)..(496)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid
<220> FEATURE:
<221> NAME/KEY: misc_feature
<222> LOCATION: (548)..(548)
<223> OTHER INFORMATION: Xaa can be any naturally occurring amino acid
<220> FEATURE:
<221> NAME/KEY: misc_feature
<222> LOCATION: (551)..(553)
<223> OTHER INFORMATION: Xaa can be any naturally occurring amino acid

<400> SEQUENCE: 71

Met Ser Asp Ile Ala Leu Thr Val Ser Xaa Leu Ala Leu Val Ala Val
1               5                   10                  15

Val Gly Leu Xaa Ile Gly Asn Xaa Lys Xaa Arg Gly Xaa Gly Xaa Gly
            20                  25                  30

Ile Gly Gly Val Leu Phe Gly Gly Ile Ile Val Gly His Phe Val Xaa
        35                  40                  45

Gln Ala Gly Xaa Thr Leu Ser Xaa Xaa Met Leu His Xaa Ile Gln Glu
    50                  55                  60

Phe Gly Leu Ile Leu Phe Val Tyr Thr Ile Gly Ile Gln Val Gly Pro
65                  70                  75                  80

Gly Phe Phe Ala Ser Leu Arg Val Xaa Gly Leu Xaa Leu Asn Leu Phe
                85                  90                  95

Ala Xaa Leu Ile Val Xaa Xaa Gly Gly Leu Val Thr Ala Ile Leu His
            100                 105                 110

Lys Xaa Phe Xaa Ile Pro Leu Pro Val Val Leu Gly Ile Phe Ser Gly
        115                 120                 125

Ala Val Thr Asn Thr Pro Ala Leu Gly Ala Gly Gln Gln Ile Leu Arg
    130                 135                 140
```

-continued

```
Asp Leu Gly Xaa Pro Xaa Xaa Xaa Val Asp Gln Met Gly Met Ser Tyr
145                 150                 155                 160

Ala Met Ala Tyr Pro Phe Gly Ile Cys Gly Ile Leu Xaa Thr Met Trp
                165                 170                 175

Xaa Xaa Arg Xaa Xaa Phe Arg Xaa Asn Val Glu Xaa Glu Ala Gln Xaa
        180                 185                 190

Xaa Xaa Xaa Ser Xaa Xaa Asn Gly Xaa Xaa Xaa Xaa Thr Xaa Asn
        195                 200                 205

Xaa Arg Val Glu Asn Pro Asn Leu Xaa Xaa Xaa Ala Ile Xaa Asp Val
    210                 215                 220

Pro Xaa Leu Asn Xaa Asp Lys Ile Ile Cys Ser Arg Leu Lys Arg Xaa
225                 230                 235                 240

Xaa Xaa Leu Xaa Val Pro Xaa Pro Xaa Thr Xaa Ile Gln Xaa Gly Asp
                245                 250                 255

Leu Leu His Leu Val Gly Xaa Xaa Xaa Asp Leu His Asn Ala Gln Leu
        260                 265                 270

Val Ile Gly Xaa Glu Val Xaa Thr Ser Leu Ser Thr Xaa Gly Thr Asp
            275                 280                 285

Leu Xaa Val Glu Arg Val Val Thr Asn Glu Xaa Val Leu Gly Lys
    290                 295                 300

Xaa Ile Arg Asp Leu His Phe Lys Xaa Arg Tyr Asp Val Val Ile Ser
305                 310                 315                 320

Arg Leu Asn Arg Ala Gly Val Glu Leu Val Ala Ser Xaa Xaa Xaa Ser
                325                 330                 335

Leu Gln Phe Gly Asp Ile Leu Asn Leu Val Gly Arg Pro Xaa Xaa Ile
                340                 345                 350

Asp Ala Val Ala Asn Xaa Xaa Gly Asn Ala Gln Gln Lys Leu Gln Gln
                355                 360                 365

Val Gln Met Leu Pro Val Phe Ile Gly Ile Gly Leu Gly Val Leu Leu
    370                 375                 380

Gly Ser Ile Pro Xaa Phe Xaa Pro Gly Phe Pro Xaa Ala Leu Lys Leu
385                 390                 395                 400

Gly Leu Ala Gly Gly Pro Leu Ile Met Ala Leu Ile Leu Gly Arg Ile
                405                 410                 415

Gly Ser Ile Gly Lys Leu Tyr Trp Phe Met Pro Pro Ser Ala Asn Leu
                420                 425                 430

Ala Leu Arg Glu Leu Gly Ile Val Leu Phe Leu Xaa Val Val Gly Leu
        435                 440                 445

Lys Ser Gly Gly Asp Phe Val Xaa Thr Leu Xaa Xaa Gly Glu Gly Leu
    450                 455                 460

Ser Trp Ile Xaa Tyr Gly Xaa Xaa Ile Thr Ala Xaa Pro Leu Xaa Thr
465                 470                 475                 480

Val Gly Xaa Leu Ala Arg Xaa Xaa Ala Lys Met Asn Tyr Leu Thr Xaa
                485                 490                 495

Cys Gly Met Leu Ala Gly Ser Met Thr Asp Pro Pro Ala Leu Ala Phe
                500                 505                 510

Ala Asn Asn Leu His Xaa Thr Ser Gly Ala Ala Ala Leu Ser Tyr Ala
                515                 520                 525

Thr Val Tyr Pro Leu Val Met Phe Leu Arg Ile Thr Pro Gln Leu
    530                 535                 540

Leu Ala Val Xaa Phe Trp Xaa Xaa Xaa
545                 550
```

<210> SEQ ID NO 72

```
<211> LENGTH: 553
<212> TYPE: PRT
<213> ORGANISM: Artificial Sequence
<220> FEATURE:
<223> OTHER INFORMATION: conserved sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (47)..(53)
<223> OTHER INFORMATION: Xaa can be any naturally occurring amino acid
<220> FEATURE:
<221> NAME/KEY: misc_feature
<222> LOCATION: (55)..(57)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (102)..(103)
<223> OTHER INFORMATION: Xaa can be any naturally occurring amino acid
<220> FEATURE:
<221> NAME/KEY: misc_feature
<222> LOCATION: (111)..(111)
```

```
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (116)..(117)
<223> OTHER INFORMATION: Xaa can be any naturally occurring amino acid
<220> FEATURE:
<221> NAME/KEY: misc_feature
<222> LOCATION: (121)..(122)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (150)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (173)..(174)
<223> OTHER INFORMATION: Xaa can be any naturally occurring amino acid
<220> FEATURE:
<221> NAME/KEY: misc_feature
<222> LOCATION: (177)..(178)
<223> OTHER INFORMATION: Xaa can be any naturally occurring amino acid
<220> FEATURE:
<221> NAME/KEY: misc_feature
<222> LOCATION: (180)..(181)
<223> OTHER INFORMATION: Xaa can be any naturally occurring amino acid
<220> FEATURE:
<221> NAME/KEY: misc_feature
<222> LOCATION: (183)..(184)
<223> OTHER INFORMATION: Xaa can be any naturally occurring amino acid
<220> FEATURE:
<221> NAME/KEY: misc_feature
<222> LOCATION: (186)..(188)
<223> OTHER INFORMATION: Xaa can be any naturally occurring amino acid
<220> FEATURE:
<221> NAME/KEY: misc_feature
<222> LOCATION: (191)..(195)
<223> OTHER INFORMATION: Xaa can be any naturally occurring amino acid
<220> FEATURE:
<221> NAME/KEY: misc_feature
<222> LOCATION: (197)..(205)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (209)..(210)
<223> OTHER INFORMATION: Xaa can be any naturally occurring amino acid
<220> FEATURE:
<221> NAME/KEY: misc_feature
<222> LOCATION: (212)..(212)
```

-continued

```
<223> OTHER INFORMATION: Xaa can be any naturally occurring amino acid
<220> FEATURE:
<221> NAME/KEY: misc_feature
<222> LOCATION: (217)..(222)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid
<220> FEATURE:
<221> NAME/KEY: misc_feature
<222> LOCATION: (231)..(233)
<223> OTHER INFORMATION: Xaa can be any naturally occurring amino acid
<220> FEATURE:
<221> NAME/KEY: misc_feature
<222> LOCATION: (241)..(242)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (253)..(254)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (263)..(266)
<223> OTHER INFORMATION: Xaa can be any naturally occurring amino acid
<220> FEATURE:
<221> NAME/KEY: misc_feature
<222> LOCATION: (268)..(271)
<223> OTHER INFORMATION: Xaa can be any naturally occurring amino acid
<220> FEATURE:
<221> NAME/KEY: misc_feature
<222> LOCATION: (274)..(274)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: misc_feature
<222> LOCATION: (279)..(281)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (290)..(292)
<223> OTHER INFORMATION: Xaa can be any naturally occurring amino acid
<220> FEATURE:
<221> NAME/KEY: misc_feature
<222> LOCATION: (305)..(305)
```

```
<223> OTHER INFORMATION: Xaa can be any naturally occurring amino acid
<220> FEATURE:
<221> NAME/KEY: misc_feature
<222> LOCATION: (310)..(311)
<223> OTHER INFORMATION: Xaa can be any naturally occurring amino acid
<220> FEATURE:
<221> NAME/KEY: misc_feature
<222> LOCATION: (313)..(314)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (327)..(327)
<223> OTHER INFORMATION: Xaa can be any naturally occurring amino acid
<220> FEATURE:
<221> NAME/KEY: misc_feature
<222> LOCATION: (333)..(335)
<223> OTHER INFORMATION: Xaa can be any naturally occurring amino acid
<220> FEATURE:
<221> NAME/KEY: misc_feature
<222> LOCATION: (350)..(351)
<223> OTHER INFORMATION: Xaa can be any naturally occurring amino acid
<220> FEATURE:
<221> NAME/KEY: misc_feature
<222> LOCATION: (353)..(353)
<223> OTHER INFORMATION: Xaa can be any naturally occurring amino acid
<220> FEATURE:
<221> NAME/KEY: misc_feature
<222> LOCATION: (356)..(359)
<223> OTHER INFORMATION: Xaa can be any naturally occurring amino acid
<220> FEATURE:
<221> NAME/KEY: misc_feature
<222> LOCATION: (378)..(378)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (391)..(391)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (399)..(399)
<223> OTHER INFORMATION: Xaa can be any naturally occurring amino acid
<220> FEATURE:
<221> NAME/KEY: misc_feature
<222> LOCATION: (408)..(409)
<223> OTHER INFORMATION: Xaa can be any naturally occurring amino acid
<220> FEATURE:
<221> NAME/KEY: misc_feature
<222> LOCATION: (444)..(444)
<223> OTHER INFORMATION: Xaa can be any naturally occurring amino acid
<220> FEATURE:
<221> NAME/KEY: misc_feature
<222> LOCATION: (455)..(456)
<223> OTHER INFORMATION: Xaa can be any naturally occurring amino acid
<220> FEATURE:
<221> NAME/KEY: misc_feature
<222> LOCATION: (459)..(460)
<223> OTHER INFORMATION: Xaa can be any naturally occurring amino acid
<220> FEATURE:
<221> NAME/KEY: misc_feature
<222> LOCATION: (462)..(462)
<223> OTHER INFORMATION: Xaa can be any naturally occurring amino acid
<220> FEATURE:
<221> NAME/KEY: misc_feature
<222> LOCATION: (465)..(465)
<223> OTHER INFORMATION: Xaa can be any naturally occurring amino acid
<220> FEATURE:
<221> NAME/KEY: misc_feature
<222> LOCATION: (468)..(468)
```

```
<223> OTHER INFORMATION: Xaa can be any naturally occurring amino acid
<220> FEATURE:
<221> NAME/KEY: misc_feature
<222> LOCATION: (471)..(472)
<223> OTHER INFORMATION: Xaa can be any naturally occurring amino acid
<220> FEATURE:
<221> NAME/KEY: misc_feature
<222> LOCATION: (475)..(476)
<223> OTHER INFORMATION: Xaa can be any naturally occurring amino acid
<220> FEATURE:
<221> NAME/KEY: misc_feature
<222> LOCATION: (479)..(479)
<223> OTHER INFORMATION: Xaa can be any naturally occurring amino acid
<220> FEATURE:
<221> NAME/KEY: misc_feature
<222> LOCATION: (483)..(483)
<223> OTHER INFORMATION: Xaa can be any naturally occurring amino acid
<220> FEATURE:
<221> NAME/KEY: misc_feature
<222> LOCATION: (487)..(489)
<223> OTHER INFORMATION: Xaa can be any naturally occurring amino acid
<220> FEATURE:
<221> NAME/KEY: misc_feature
<222> LOCATION: (496)..(496)
<223> OTHER INFORMATION: Xaa can be any naturally occurring amino acid
<220> FEATURE:
<221> NAME/KEY: misc_feature
<222> LOCATION: (515)..(515)
<223> OTHER INFORMATION: Xaa can be any naturally occurring amino acid
<220> FEATURE:
<221> NAME/KEY: misc_feature
<222> LOCATION: (518)..(518)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: misc_feature
<222> LOCATION: (540)..(541)
<223> OTHER INFORMATION: Xaa can be any naturally occurring amino acid
<220> FEATURE:
<221> NAME/KEY: misc_feature
<222> LOCATION: (544)..(544)
<223> OTHER INFORMATION: Xaa can be any naturally occurring amino acid
<220> FEATURE:
<221> NAME/KEY: misc_feature
<222> LOCATION: (548)..(548)
<223> OTHER INFORMATION: Xaa can be any naturally occurring amino acid
<220> FEATURE:
<221> NAME/KEY: misc_feature
<222> LOCATION: (551)..(553)
<223> OTHER INFORMATION: Xaa can be any naturally occurring amino acid

<400> SEQUENCE: 72

Met Ser Xaa Ile Ala Leu Thr Val Ser Xaa Leu Ala Leu Val Ala Val
1               5                   10                  15

Xaa Gly Leu Xaa Ile Gly Asn Xaa Lys Xaa Xaa Gly Xaa Gly Xaa Gly
            20                  25                  30

Ile Gly Gly Val Leu Phe Gly Gly Ile Ile Val Gly His Phe Xaa Xaa
        35                  40                  45

Xaa Xaa Xaa Xaa Xaa Leu Xaa Xaa Xaa Met Leu His Xaa Ile Gln Glu
    50                  55                  60

Phe Gly Leu Ile Leu Phe Val Tyr Thr Ile Gly Ile Gln Val Gly Pro
65                  70                  75                  80

Gly Phe Phe Xaa Ser Leu Arg Val Xaa Gly Leu Xaa Leu Asn Xaa Phe
                85                  90                  95

Ala Xaa Leu Xaa Val Xaa Xaa Gly Gly Leu Val Thr Ala Ile Xaa His
            100                 105                 110

Lys Xaa Phe Xaa Xaa Pro Leu Pro Xaa Xaa Leu Gly Xaa Phe Ser Gly
        115                 120                 125
```

```
Ala Val Thr Asn Thr Pro Ala Leu Gly Ala Xaa Gln Gln Ile Leu Xaa
            130                 135                 140

Asp Leu Gly Xaa Pro Xaa Xaa Xaa Val Xaa Gln Met Gly Met Xaa Tyr
145                 150                 155                 160

Ala Met Ala Tyr Pro Phe Gly Ile Cys Gly Ile Leu Xaa Xaa Met Trp
                165                 170                 175

Xaa Xaa Arg Xaa Xaa Phe Xaa Xaa Asn Xaa Xaa Xaa Glu Ala Xaa Xaa
            180                 185                 190

Xaa Xaa Xaa Ser Xaa Xaa Xaa Xaa Xaa Xaa Xaa Xaa Thr Xaa Asn
            195                 200                 205

Xaa Xaa Val Xaa Asn Pro Asn Leu Xaa Xaa Xaa Xaa Xaa Asp Val
    210                 215                 220

Pro Xaa Leu Asn Xaa Asp Xaa Xaa Xaa Cys Ser Arg Leu Lys Arg Glu
225                 230                 235                 240

Xaa Xaa Leu Xaa Val Pro Xaa Pro Xaa Thr Xaa Ile Xaa Xaa Gly Asp
                245                 250                 255

Xaa Leu His Leu Val Gly Xaa Xaa Xaa Leu Xaa Xaa Xaa Xaa Leu
            260                 265                 270

Val Xaa Gly Xaa Glu Val Xaa Xaa Xaa Leu Ser Thr Xaa Gly Thr Xaa
    275                 280                 285

Leu Xaa Xaa Xaa Arg Val Val Val Thr Asn Glu Asn Val Leu Gly Lys
    290                 295                 300

Xaa Ile Arg Asp Leu Xaa Xaa Lys Xaa Xaa Tyr Asp Val Val Ile Xaa
305                 310                 315                 320

Arg Leu Asn Arg Ala Gly Xaa Glu Leu Val Ala Ser Xaa Xaa Xaa Ser
                325                 330                 335

Leu Gln Phe Gly Asp Ile Leu Asn Leu Val Gly Arg Pro Xaa Xaa Ile
            340                 345                 350

Xaa Ala Val Xaa Xaa Xaa Xaa Gly Asn Ala Gln Gln Lys Leu Gln Gln
    355                 360                 365

Val Gln Met Leu Pro Val Phe Ile Gly Xaa Gly Leu Gly Val Leu Leu
370                 375                 380

Gly Ser Ile Pro Xaa Phe Xaa Pro Gly Phe Pro Xaa Ala Leu Xaa Leu
385                 390                 395                 400

Gly Leu Ala Gly Gly Pro Leu Xaa Xaa Ala Leu Ile Leu Gly Arg Ile
                405                 410                 415

Gly Ser Ile Gly Lys Leu Tyr Trp Phe Met Pro Pro Ser Ala Asn Leu
            420                 425                 430

Ala Leu Arg Glu Leu Gly Ile Val Leu Phe Leu Xaa Val Val Gly Leu
            435                 440                 445

Lys Ser Gly Gly Asp Phe Xaa Xaa Thr Leu Xaa Xaa Gly Xaa Gly Leu
450                 455                 460

Xaa Trp Ile Xaa Tyr Gly Xaa Xaa Ile Thr Xaa Xaa Pro Leu Xaa Thr
465                 470                 475                 480

Val Gly Xaa Leu Ala Arg Xaa Xaa Xaa Lys Met Asn Tyr Leu Thr Xaa
            485                 490                 495

Cys Gly Met Leu Ala Gly Ser Met Thr Asp Pro Pro Ala Leu Ala Phe
            500                 505                 510
```

```
                                            -continued

Ala Asn Xaa Leu His Xaa Thr Ser Gly Ala Ala Ala Leu Ser Tyr Ala
        515             520                 525

Thr Val Tyr Pro Leu Xaa Met Phe Leu Arg Ile Xaa Xaa Pro Gln Xaa
    530             535                 540

Leu Ala Val Xaa Phe Trp Xaa Xaa Xaa
545                 550
```